US011332546B2

(12) United States Patent
Ge et al.

(10) Patent No.: US 11,332,546 B2
(45) Date of Patent: May 17, 2022

(54) PROTEASE INHIBITORY ANTIBODIES AND METHODS OF USE THEREOF

(71) Applicant: The Regents of The University of California, Oakland, CA (US)

(72) Inventors: Xin Ge, Manvel, TX (US); Kibaek Lee, Houston, TX (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/880,747

(22) Filed: May 21, 2020

(65) Prior Publication Data
US 2020/0392251 A1   Dec. 17, 2020

Related U.S. Application Data

(60) Provisional application No. 62/850,914, filed on May 21, 2019.

(51) Int. Cl.
*C07K 16/40* (2006.01)

(52) U.S. Cl.
CPC .......... *C07K 16/40* (2013.01); *C07K 2317/55* (2013.01); *C07K 2317/565* (2013.01); *C07K 2317/76* (2013.01); *C07K 2317/92* (2013.01); *C07K 2317/94* (2013.01)

(58) Field of Classification Search
CPC ................ C07K 16/40; C07K 2317/55; C07K 2317/565; C07K 2317/76; C07K 2317/92; C07K 2317/94
See application file for complete search history.

(56) References Cited

U.S. PATENT DOCUMENTS

| | | | |
|---|---|---|---|
| 7,767,206 | B2 | 8/2010 | Tocker et al. |
| 10,975,166 | B2 | 4/2021 | Ge et al. |
| 2007/0217997 | A1 | 9/2007 | Devy et al. |
| 2007/0218069 | A1 | 9/2007 | Gordon et al. |
| 2008/0206239 | A1 | 8/2008 | Jones et al. |
| 2009/0311183 | A1* | 12/2009 | Devy ............. A61P 35/00 424/9.1 |
| 2011/0135573 | A1 | 6/2011 | Devy |
| 2015/0232549 | A1 | 8/2015 | Fuh et al. |
| 2018/0134808 | A1 | 5/2018 | Sagi et al. |
| 2019/0144540 | A1 | 5/2019 | Koide et al. |
| 2019/0185581 | A1 | 6/2019 | Ge et al. |
| 2021/0087296 | A1 | 3/2021 | Ge et al. |

FOREIGN PATENT DOCUMENTS

| | | |
|---|---|---|
| WO | 2013106485 A2 | 7/2013 |
| WO | 2013130905 A1 | 9/2013 |
| WO | 2015050959 A1 | 4/2015 |
| WO | 2018067198 A1 | 4/2018 |
| WO | 2020237092 A2 | 11/2020 |

OTHER PUBLICATIONS

Wu et al. "Humanization of a murine monoclonal antibody by simultaneous optimization of framework and CDR residues", J. Mol. Biol. (1999) 294, 151-162 (Year: 1999).*
Padlan et al. "Structure of an antibody-antigen complex: crystal structure of the HyHEL-10 Fab-lysozyme complex", PNAS 1989, 86: 5938-5942 (Year: 1989).*
Pascalis et al. "Grafting of "Abbreviated" Complementarity-Determining Regions Containing Specificity-Determining Residues Essential for Ligand Contact to Engineer a Less Immunogenic Humanized Monoclonal Antibody", The Journal of Immunology (2002) 169, 3076-3084 (Year: 2002).*
Casset et al. "A peptide mimetic of an anti-CD4 monoclonal antibody by rational design", BBRC 2003, 307:198-205 (Year: 2003).*
Vajdos et al. "Comprehensive functional maps of the antigen-binding site of an anti-ErbB2 antibody obtained with shotgun scanning mutagenesis", J. Mol. Biol. (2002) 320, 415-428 (Year: 2002).*
Chen et al. "Selection and analysis of an optimized anti-VEGF antibody: crystal structure of an affinity-matured Fab in complex with antigen", J. Mol. Bio. (1999) 293, 865-881 (Year: 1999).*
Lamminmaki et al. "Crystal structure of a recombinant anti-estradiol Fab fragment in complex with 17beta-estradiol", JBC 2001, 276:36687-36694 (Year: 2001).*
Rudikoff et al . "Single amino acid altering antigen-binding specificity", Proc Natl Acad Sci USA 1982 vol. 79 p. 1979 (Year: 1979).*
MacCallum et al. "Antibody-antigen Interactions: Contact Analysis and Binding Site Topography", J. Mol. Biol. (1996) 262, 732-745 (Year: 1996).*
Atwal, J , et al., "A therapeutic antibody targeting BACE1 inhibits amyloid-β production in vivo", Sci Transl Med 3 (84), 84ra43 (2011).
Botkjaer, K, et al., "Development of a specific affinity-matured exosite inhibitor to MT1-MMP that efficiently inhibits tumor cell invasion in vitro and metastasis in vivo", Oncotarget 7(13), 16773-16792 (2016).
Castro , et al., "Inhibition of Matrix Metalloproteinases (MMPs) as a Potential Strategy to Ameliorate Hypertension-Induced Cardiovascular Alterations", Curr Drug Targets 14(3), 335-343 (2013).
Cook , et al., "Defective Extracellular Matrix Reorganization by Chronic Wound Fibroblasts is Associated with Alterations in TIMP-1, TIMP-2, and MMP-2 Activity", J Invest Dermatol 115(2), 225-233 (2000).
David, T, et al., "Factor Xla-specific IgG and a reversal agent to probe factor XI function in thrombosis and hemostasis", Sci Transl Med 8, 353ra112 (2016).

(Continued)

*Primary Examiner* — Sharon X Wen
*Assistant Examiner* — Peter Johansen
(74) *Attorney, Agent, or Firm* — Viksnins Harris Padys Malen LLP

(57) ABSTRACT

Certain embodiments provide isolated anti-MMP-14 antibodies or fragments thereof, isolated anti-MMP-12 antibodies or fragments thereof, isolated anti-BACE-1 antibodies or fragments thereof, isolated anti-Alp2 antibodies or fragments thereof, and isolated anti-cathepsin B antibodies or fragments thereof, as well as methods of use thereof.

18 Claims, 17 Drawing Sheets

Specification includes a Sequence Listing.

(56) References Cited

OTHER PUBLICATIONS

De Strooper, B , "Proteases and proteolysis in Alzheimer disease: a multifactorial view on the disease process", Physiol Rev 90, 465-494 (2010).
Decock, J , et al., "Matrix metalloproteinases: protective roles in cancer", Cell Mol Med 15(6), 1254-1265 (2011).
Deu, E , et al., "New tools for dissecting protease function: implications for inhibitor design, drug discovery and probe development", Nat Struct Mol Biol 19(1), 9-16 (2012).
Dev, et al., "Therapeutic potential of matrix metalloprotease inhibitors in neuropathic pain", Expert Opin Investig Drugs 19(4), 455-468 (2010).
Devy, L , et al., "Selective Inhibition of Matrix Metalloproteinase-14 Blocks Tumor Growth, Invasion, and Angiogenesis", Cancer Res 69(4), 1517-1526 (2009).
Drag, M , et al., "Emerging principles in protease-based drug discovery", Nat Rev Drug Discov 9(9), 690-701 (2010).
Elkington, P , et al., "The paradox of matrix metalloproteinases in infectious disease", Clin Exp Immunol 142(1), 12-20 (2005).
Gialeli , et al., "Roles of matrix metalloproteinases in cancer progression and their pharmacological targeting", FEBS J 278(1), 16-27 (2011).
Ji, R , et al., "MMP regulation of neuropathic pain", Trends Pharmacol Sci 30, 336-340 (2009).
Kenniston, J , et al., "Inhibition of plasma kallikrein by a highly specific active site blocking antibody", J Biol Chem 289, 23596-23608 (2014).
Kjaerup, R , et al., "Uncharacterized Protein", UniProt Accession A0A1AoL572, 1 page (May 10, 2017).
Lee, K , et al., "Generation of highly selective monoclonal antibodies inhibiting a recalcitrant protease using decoy designs", Biotechnology and Bioengineering 117(12), 3664-3676 (2020).
Lee, K , et al., "Reducing proteolytic liability of a MMP-14 inhibitory antibody by site-saturation mutagenesis", Protein Science 28, 643-653 (2019).
Liu, Y , et al., "Increased matrix metalloproteinase-9 predicts poor wound healing in diabetic foot ulcers", Diabetes Care 32(1), 117-119 (2009).
Lloyd, C , "Modelling the human immune response: performance of a 1011 human antibody repertoire against a broad panel of therapeutically relevant antigens", Protein Engineering, Design and Selection 22(3), 159-168 (2009).
Lopez, T , et al., "Functional selection of protease inhibitory antibodies", PNAS 116(33), 16314-16319 (2019).
Lopez, T , et al., "Identification of Highly Selective MMP-14 Inhibitory Fabs by Deep Sequencing", Biotechnol Bioeng 114(6), 1140-1150; and 7 pages of Supporting Information (2017).
Lopez, T , "Selection of Inhibitory Antibodies Using Next Generation High Throughput Sequencing", 251st ACS National Meeting and Exposition, San Diego, CA, presentation, 23 pages (Mar. 15, 2016).
Lopez-Otin, C , et al., "Emerging roles of proteases in tumour suppression", Nat Rev Cancer 7, 800-808 (2007).
MacCallum , et al., "Antibody-antigen Interactions: Contact Analysis and Binding Site Topography", J Mol Biol 262,732-745 (1996).
Nam, D , et al., "Active-site MMP-selective antibody inhibitors discovered from convex paratope synthetic libraries", Proc Natl Acad Sci 113(52), 14970-14975 (2016).
Nam, D , "Generation of Highly Selective Monoclonal Antibodies Inhibiting Tumorigenic Proteases", UC Riverside. ProQuest ID: Nam_ucr_0032D_12199. Merritt ID: ark:/13030/m5m06s16. Retrieved from https://escholarship.org/uc/item/0pd6m2b9, 148 pages, Jun. 2015.
Nam, D , et al., "Generation of Protease-Inhibiting Monoclonal Antibodies By Novel Paratope Design", American Institute of Chemical Engineers (AIChE) Annual Meeting, Salt Lake City, UT, presentation, 25 pages (Nov. 2015).

Overall, C , et al., "Towards third generation matrix metalloproteinase inhibitors for cancer therapy", Br J Cancer 94, 941-946 (2006).
Overall , et al., "Tumour microenvironment—opinion: validating matrix metalloproteinases as drug targets and anti-targets for cancer therapy", Nat Rev Cancer 6(3), 227-239 (2006).
Padlan , et al., "Structure of an antibody-antigen complex: Crystal structure of the HyHEL-10 Fab-lysozyme complex", PNAS 86,5938-5942 (1989).
Prassas, I , et al., "Unleashing the therapeutic potential of human kallikrein-related serine proteases", Nat Rev Drug Discov 14, 183-202 (2015).
Schneider, E , et al., "A reverse binding motif that contributes to specific protease inhibition by antibodies", J Mol Biol 415, 699-715 (2012).
Sharma, S , et al., "Antibody Directed Enzyme Prodrug Therapy (ADEPT): Trials and tribulations", Adv Drug Deliv Rev 118, 2-7 (2017).
Troeberg, L , et al., "Proteases involved in cartilage matrix degradation in osteoarthritis", Biochim Biophys Acta 1824, 133-145 (2012).
Turk, B , et al., "Protease signalling: the cutting edge", EMBO J 31, 1630-1643 (2012).
Turk, B , "Targeting proteases: successes, failures and future prospects", Nat Rev Drug Discov 5(9), 785-799 (2006).
Vajdos, F , et al., "Comprehensive Functional Maps of the Antigen-binding Site of an Anti-ErbB2 Antibody Obtained with Shotgun Scanning Mutagenesis", J Mol Biol 320, 415-428 (2002).
Vandenbroucke, R , et al., "Is there new hope for therapeutic matrix metalloproteinase inhibition?", Nat Rev Drug Discov 13, 904-927 (2014).
Vanlaere, I , et al., "Matrix Metalloproteinases as Drug Targets in Infections Caused by Gram-Negative Bacteria and in Septic Shock", Clin Microbiol Rev 22(2), 224-239 (2009).
Vassar, R , "BACE1 inhibitor drugs in clinical trials for Alzheimer's disease", Alzheimers Res Ther 6, 89, 1-14 (2014).
Wang, X , et al., "IgG Fc engineering to modulate antibody effector functions", Protein Cell 9, 63-73 (2018).
Wang, F , et al., "Reshaping Antibody Diversity", Cell 153(6), 1379-1393 (2013).
Wu, Y , et al., "Structural insight into distinct mechanisms of protease inhibition by antibodies", PNAS 104, 19784-19789 (2007).
Yu, Y , et al., "Therapeutic bispecific antibodies cross the blood-brain barrier in nonhuman primates", Sci Transl Med 6, (261) 261ra154 (2014).
Zucker , et al., "Selective matrix metalloproteinase (MMP) inhibitors in cancer therapy: ready for prime time?", Cancer Biol Ther 8(24), 2371-2373 (2009).
Asahi, M , et al., "Effects of Matrix Metalloproteinase-9 Gene Knock-Out on the Proteolysis of Blood-Brain Barrier and White Matter Components after Cerebral Ischemia", Journal of Neuroscience 21(19), 7724-7732 (2001).
Asahi, M , et al., "Role for Matrix Metalloproteinase 9 After Focal Cerebral Ischemia: Effects of Gene Knockout and Enzyme Inhibition With BB-94", Journal of Cerebral Blood Flow and Metabolism 20, 1681-1689 (2000).
Fujimura, M , et al., "Early appearance of activated matrix metalloproteinase-9 and blood-brain barrier disruption in mice after focal cerebral ischemia and reperfusion", Brain Research 842, 92-100 (1999).
Jiang, X , et al., "Matrix metalloproteinase inhibitor KB-R7785 attenuates brain damage resulting from permanent focal cerebral ischemia in mice", Neuroscience 305, 41-44 (2001).
Kawasaki, Y, et al., "Distinct roles of matrix metalloproteases in the early- and late-phase development of neuropathic pain", Nat Med. 14(3), 331-336 (2008) (NIH-PA Author Manuscript version, 12 pages).
Lopez, T, et al., "Epitope-specific affinity maturation improved stability of potent protease inhibitory antibodies", Biotechnol Bioeng. 115(11), 2673-2682 (2018).
Nam, D.H. et al., "Protease Inhibition Mechanism of Camelid-like Synthetic Human Antibodies", Biochemistry 59, 3802-3812 (2020).

(56) References Cited

OTHER PUBLICATIONS

Ramos-Fernandez, M , et al., "Matrix Metalloproteinase-9 as a Marker for Acute Ischemic Stroke: A Systematic Review", Journal of Stroke and Cerebrovascular Diseases 20(1), 47-54 (2011).
Romanic, A , et al., "Matrix Metalloproteinase Expression Increases After Cerebral Focal Ischemia in Rats Inhibition of Matrix Metalloproteinase-9 Reduces Infarct Size", Stroke 29, 1020-1030 (1998).
Svedin, P , et al., "Matrix Metalloproteinase-9 Gene Knock-out Protects the Immature Brain after Cerebral Hypoxia-Ischemia", Journal of Neuroscience 27(7), 1511-1518 (2007).

* cited by examiner

SEQUENCE LISTING

```
<160> NUMBER OF SEQ ID NOS: 153

<210> SEQ ID NO 1
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Ser
            20                  25                  30

Tyr Ile His Trp Val Arg Gln Ala Pro Gly Lys Gly Leu Glu Trp Val
        35                  40                  45

Ala Ser Ile Tyr Ser Ser Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Asp Ser Ala Val Tyr Ser Val Arg Arg Met Gly Ser Ser
            100                 105                 110

Gly Leu Ala Ala Tyr Ala Met Asp Tyr Trp Gly Gln Gly Thr Leu Val
```

```
                115                 120                 125
Thr Val Ser Ser Ala Ser
    130

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Asn Leu Tyr Ser Ser Tyr Ile His
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ile Tyr Ser Ser Tyr Ser Ser Thr Tyr Tyr Ala Asp Ser Val Lys
1               5                   10                  15

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Asp Ser Ala Val Tyr Ser Val Arg Arg Met Gly Ser Ser Gly Leu
1               5                   10                  15

Ala Ala Tyr Ala Met Asp Tyr
            20

<210> SEQ ID NO 5
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Ser Met His Trp Val Arg Gln Ala Pro Gly Lys Gly Leu Glu Trp Val
        35                  40                  45

Ala Tyr Ile Tyr Ser Ser Ser Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Asp Cys Cys Ser Cys Val Phe Ser Gln Ser Ala Gly Ile Thr
            100                 105                 110

Leu Ala Cys Val Tyr Val Met Asp Tyr Trp Gly Gln Gly Thr Leu Val
        115                 120                 125

Thr Val Ser Ser Ala Ser
        130

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Asn Ile Tyr Tyr Ser Ser Met His
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ile Tyr Ser Ser Ser Tyr Thr Tyr Tyr Ala Asp Ser Val Lys
1               5                   10                  15

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Cys Cys Ser Cys Val Phe Ser Gln Ser Ala Gly Ile Thr Leu Ala
1               5                   10                  15

Cys Val Tyr Val Met Asp Tyr
            20

<210> SEQ ID NO 9
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Tyr
            20                  25                  30

Tyr Met His Trp Val Arg Gln Ala Pro Gly Lys Gly Leu Glu Trp Val
        35                  40                  45

Ala Tyr Ile Tyr Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Leu Asp Phe Leu Met Arg Asp Ile Tyr Tyr Asp Leu Gly Gly
            100                 105                 110

Gly Ala Leu Gly Trp Leu Ile Lys Tyr Ala Met Asp Tyr Trp Gly Gln
        115                 120                 125

Gly Thr Leu Val Thr Val Ser Ser Ala Ser
    130                 135

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Asn Leu Tyr Tyr Tyr Tyr Met His
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Tyr Pro Tyr Ser Gly Ser Thr Tyr Tyr Ala Asp Ser Val Lys
1               5                   10                  15

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Asp Phe Leu Met Arg Asp Ile Tyr Tyr Asp Leu Gly Gly Gly Ala
1               5                   10                  15

Leu Gly Trp Leu Ile Lys Tyr Ala Met Asp Tyr
            20                  25

<210> SEQ ID NO 13
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Met His Trp Val Arg Gln Ala Pro Gly Lys Gly Leu Glu Trp Val
        35                  40                  45

Ala Ser Ile Tyr Pro Ser Tyr Gly Tyr Thr Tyr Tyr Ala Asp Ser Val
```

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Leu Phe Ala Cys Trp Arg Gln Ser Ile Leu Thr Pro Pro
            100                 105                 110

Leu Leu Ser Ala Met Met Met Gly Tyr Ala Met Asp Tyr Trp Gly Gln
        115                 120                 125

Gly Thr Leu Val Thr Val Ser Ser Ala Ser
    130                 135

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Phe Asn Ile Tyr Tyr Ser Tyr Met His
 1               5                  10

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ile Tyr Pro Ser Tyr Gly Tyr Thr Tyr Tyr Ala Asp Ser Val Lys
 1               5                  10                  15

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Leu Phe Ala Cys Trp Arg Gln Ser Ile Leu Thr Pro Pro Leu Leu
 1               5                  10                  15

Ser Ala Met Met Met Gly Tyr Ala Met Asp Tyr
             20                  25

<210> SEQ ID NO 17
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Ser Ser Ser
             20                  25                  30
```

```
Ser Met His Trp Val Arg Gln Ala Pro Gly Lys Gly Leu Glu Trp Val
            35                  40                  45

Ala Ser Ile Tyr Pro Tyr Tyr Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Val Thr Arg Phe Thr Asn Asp Ala Ser Val Gly Gln Val
            100                 105                 110

Trp Ala Gly Ala Tyr Gly Met Asp Tyr Trp Gly Gln Gly Thr Leu Val
            115                 120                 125

Thr Val Ser Ser Ala Ser
        130
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gly Phe Asn Ile Ser Ser Ser Ser Met His
 1               5                  10
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ser Ile Tyr Pro Tyr Tyr Gly Tyr Thr Tyr Tyr Ala Asp Ser Val Lys
 1               5                  10                  15
```

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gly Val Thr Arg Phe Thr Asn Asp Ala Ser Val Gly Gln Val Trp Ala
 1               5                  10                  15

Gly Ala Tyr Gly Met Asp Tyr
            20
```

<210> SEQ ID NO 21
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Asn Phe Ser Ser
        20                  25                  30

Ser Ile His Trp Val Arg Gln Ala Pro Gly Lys Gly Leu Glu Trp Val
        35                  40                  45

Ala Ser Ile Ser Ser Ser Tyr Gly Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Val Arg Met Leu Pro Val Arg Cys Ile Pro Arg Cys Ile
            100                 105                 110

Lys Thr Thr Leu Pro Leu Tyr Gly Met Asp Tyr Trp Gly Gln Gly Thr
        115                 120                 125

Leu Val Thr Val Ser Ser Ala Ser
    130                 135
```

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Gly Phe Asn Phe Ser Ser Ser Ser Ile His
1               5                   10
```

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Ser Ile Ser Ser Ser Tyr Gly Tyr Thr Tyr Tyr Ala Asp Ser Val Lys
1               5                   10                  15
```

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Val Val Arg Met Leu Pro Val Arg Cys Ile Pro Arg Cys Ile Lys Thr
1               5                   10                  15

Thr Leu Pro Leu Tyr Gly Met Asp Tyr
            20                  25
```

<210> SEQ ID NO 25
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Thr Tyr
            20                  25                  30

Leu Asn Trp Tyr Gln Gln Lys Pro Gly Lys Ala Pro Lys Leu Leu Ile
        35                  40                  45

Tyr Ala Thr Ser Asn Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Arg
                85                  90                  95

Phe Thr Phe Gly Pro Gly Thr Lys Leu Glu Ile Lys Arg
            100                 105

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ser Gln Ser Val Gly Thr Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Thr Ser Asn Leu Arg Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Ser Tyr Ser Ile Pro Arg Phe Thr
1               5                   10

<210> SEQ ID NO 29
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Pro Tyr Ser
            20                  25                  30

Ser Met His Trp Val Arg Gln Ala Pro Gly Lys Gly Leu Glu Trp Val
        35                  40                  45

Ala Ser Ile Ser Ser Tyr Ser Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ile Cys Gly His Arg Trp Arg Asp Phe Asp Met Trp Arg
            100                 105                 110

Ala Arg Thr Gly Val Asn Tyr Ala Met Asp Tyr Trp Gly Gln Gly Thr
        115                 120                 125

Leu Val Thr Val Ser Ser Ala Ser
    130                 135

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Phe Asn Ile Pro Tyr Ser Ser Met His
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ile Ser Ser Tyr Ser Ser Ser Thr Ser Tyr Ala Asp Ser Val Lys
1               5                   10                  15

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Ile Cys Gly His Arg Trp Arg Asp Phe Asp Met Trp Arg Ala Arg
1               5                   10                  15

Thr Gly Val Asn Tyr Ala Met Asp Tyr
            20                  25

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Pro Thr Ile Ser Ser Leu Gln Pro
65              70                  75                  80

Glu Asp Phe Ala Thr Tyr Tyr Cys Gln Gln Ala Ser Ala Ser Pro Tyr
                85                  90                  95

Ala Leu Ile Thr Phe Gly Gln Gly Thr Lys Val Glu Ile Lys Arg
            100                 105                 110

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ala Ser Gln Ser Val Ser Ser Ala Val Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ala Ser Ser Leu Tyr Ser
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Ala Ser Ala Ser Pro Tyr Ala Leu Ile Thr
1               5                   10

<210> SEQ ID NO 37
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser

```
            20                  25                  30
Ser Ile His Trp Val Arg Gln Ala Pro Gly Lys Gly Leu Glu Trp Val
        35                  40                  45

Ala Tyr Ile Ser Pro Ser Ser Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Tyr Tyr Val Ser Val Gly Ser Gly Ile Asp Tyr Trp Gly
            100                 105                 110

Gln Gly Thr Leu Val Thr Val Ser Ser Ala Ser
        115                 120

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Asn Ile Ser Tyr Ser Ser Ile His
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Ser Pro Ser Ser Ser Tyr Thr Ser Tyr Ala Asp Ser Val Lys
1               5                   10                  15

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Tyr Tyr Val Ser Val Gly Ser Gly Ile Asp Tyr
1               5                   10

<210> SEQ ID NO 41
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30
```

```
Tyr Met His Trp Val Arg Gln Ala Pro Gly Lys Gly Leu Glu Trp Val
         35                  40                  45

Ala Ser Ile Tyr Pro Tyr Tyr Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Trp His Gly Tyr Pro Pro Gly Tyr Ser Tyr Tyr Ser Ser Phe
             100                 105                 110

Ser Ser Ser Gly Phe Asp Tyr Trp Gly Gln Gly Thr Leu Val Thr Val
         115                 120                 125

Ser Ser Ala Ser
     130
```

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

```
Ser Ile Tyr Pro Tyr Tyr Gly Ser Thr Tyr Tyr Ala Asp Ser Val Lys
 1               5                   10                  15
```

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Trp His Gly Tyr Pro Pro Gly Tyr Ser Tyr Tyr Ser Ser Phe Ser Ser
 1               5                   10                  15

Ser Gly Phe Asp Tyr
             20
```

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Tyr Tyr Leu Ile
```

```
                        85                  90                  95
Thr Phe Gly Gln Gly Thr Lys Val Glu Ile Lys Arg
                100                 105

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Tyr Gly Tyr Tyr Leu Ile Thr
1               5

<210> SEQ ID NO 46
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Tyr Met His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Gly Tyr Tyr Ala Trp Phe Gly Ser His Pro Trp Ala
            100                 105                 110

Tyr Gly Ala Phe Asp Tyr Trp Gly Gln Gly Thr Leu Val Thr Val Ser
        115                 120                 125

Ser Ala Ser
    130

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Asn Ile Ser Ser Tyr Tyr Met His
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 48

Ser Ile Tyr Ser Ser Tyr Gly Tyr Thr Tyr Tyr Ala Asp Ser Val Lys
1               5                   10                  15

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Trp Gly Tyr Tyr Ala Trp Phe Gly Ser His Pro Trp Ala Tyr Gly
1               5                   10                  15

Ala Phe Asp Tyr
            20

<210> SEQ ID NO 50
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Ile His Trp Val Arg Gln Ala Pro Gly Lys Gly Leu Glu Trp Val
        35                  40                  45

Ala Tyr Ile Ser Ser Tyr Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ala Ser Gly Ile Asp Tyr Trp Gly Gln Gly Thr Leu Val
            100                 105                 110

Thr Val Ser Ser Ala Ser
        115

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Ile Ser Ser Tyr Ser Ser Thr Tyr Tyr Ala Asp Ser Val Lys
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ser Ala Ser Gly Ile Asp Tyr
1               5

<210> SEQ ID NO 53
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Met His Trp Val Arg Gln Ala Pro Gly Lys Gly Leu Glu Trp Val
        35                  40                  45

Ala Ser Ile Tyr Pro Ser Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Ser Ser Tyr Tyr Tyr Gly Met Asp Tyr Trp Gly Gln
            100                 105                 110

Gly Thr Leu Val Thr Val Ser Ser Ala Ser
        115                 120

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Asn Ile Ser Tyr Ser Ser Met His
1               5                   10

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ile Tyr Pro Ser Tyr Ser Tyr Thr Ser Tyr Ala Asp Ser Val Lys
1               5                   10                  15

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 56

Ser Ser Ser Ser Tyr Tyr Tyr Gly Met Asp Tyr
1               5                   10

<210> SEQ ID NO 57
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Ser Met His Trp Val Arg Gln Ala Pro Gly Lys Gly Leu Glu Trp Val
        35                  40                  45

Ala Tyr Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Asn Ser Ile Cys Val Leu Thr Gln Lys Glu Val Asp Thr
            100                 105                 110

Lys Phe Leu Val Gly Gln His Ser Tyr Val Met Asp Tyr Trp Gly Gln
        115                 120                 125

Gly Thr Leu Val Thr Val Ser Ser Ala Ser
    130                 135

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Phe Asn Ile Tyr Ser Ser Ser Met His
1               5                   10

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Ile Tyr Ser Ser Tyr Gly Tyr Thr Tyr Tyr Ala Asp Ser Val Lys
1               5                   10                  15

<210> SEQ ID NO 60
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Asp Asn Ser Ile Cys Val Leu Thr Gln Lys Glu Val Asp Thr Lys Phe
1               5                   10                  15

Leu Val Gly Gln His Ser Tyr Val Met Asp Tyr
            20                  25

<210> SEQ ID NO 61
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Ser Met His Trp Val Arg Gln Ala Pro Gly Lys Gly Leu Glu Trp Val
        35                  40                  45

Ala Ser Ile Ser Pro Tyr Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Arg Ser Ser Cys Pro Val Gly Trp Arg Asp Ser Arg Phe
            100                 105                 110

Gly Ala Asp Gly Tyr Gly Leu Glu Tyr Trp Gly Gln Gly Thr Leu Val
        115                 120                 125

Thr Val Ser Ser Ala Ser
    130

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Asn Ile Ser Tyr Tyr Ser Met His
1               5                   10

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ile Ser Pro Tyr Tyr Gly Ser Thr Tyr Tyr Ala Asp Ser Val Lys
1               5                   10                  15

<210> SEQ ID NO 64
<211> LENGTH: 23
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 64

Glu Arg Ser Ser Cys Pro Val Gly Trp Arg Asp Ser Arg Phe Gly Ala
1               5                   10                  15

Asp Gly Tyr Gly Leu Glu Tyr
            20

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Tyr Ile His Trp Val Arg Gln Ala Pro Gly Lys Gly Leu Glu Trp Val
        35                  40                  45

Ala Ser Ile Tyr Ser Tyr Ser Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Gly Asp Thr Ala Val Tyr Tyr Cys
                85                  90                  95

Ala Arg Phe Gly Ser Trp Ser Tyr Ala Ile Asp Tyr Trp Gly Gln Gly
            100                 105                 110

Thr Leu Val Thr Val Ser Ser Ala Ser
        115                 120

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Phe Asn Ile Ser Ser Tyr Tyr Ile His
1               5                   10

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Ile Tyr Ser Tyr Ser Ser Tyr Thr Tyr Tyr Ala Asp Ser Val Lys
1               5                   10                  15

<210> SEQ ID NO 68
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Gly Ser Trp Ser Tyr Ala Ile Asp Tyr
1               5                   10

<210> SEQ ID NO 69
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
                20                  25                  30

Ser Met His Trp Val Arg Gln Ala Pro Gly Lys Gly Leu Glu Trp Val
            35                  40                  45

Ala Ser Ile Tyr Pro Ser Tyr Ser Tyr Thr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Lys Thr Ser Asp Gln Tyr Leu Leu Val Gly Gly Ser Phe Phe
            100                 105                 110

Lys Leu Arg Asp Cys Cys Tyr Val Met Asp Tyr Trp Gly Gln Gly Thr
        115                 120                 125

Leu Val Thr Val Ser Ser Ala Ser
            130                 135

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Phe Asn Leu Ser Ser Ser Ser Met His
1               5                   10

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Ile Tyr Pro Ser Tyr Ser Tyr Thr Tyr Tyr Ala Asp Ser Val Lys
1               5                   10                  15

<210> SEQ ID NO 72
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Thr Ser Asp Gln Tyr Leu Leu Val Gly Ser Phe Phe Lys Leu
1               5                   10                  15

Arg Asp Cys Cys Tyr Val Met Asp Tyr
            20                  25

<210> SEQ ID NO 73
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Ile His Trp Val Arg Gln Ala Pro Gly Lys Gly Leu Glu Trp Val
        35                  40                  45

Ala Ser Ile Tyr Ser Tyr Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Pro Gly Pro Tyr Ala Val Cys Gly Asn Leu Phe
            100                 105                 110

Arg Ser Val Ser Tyr Gly Met Asp Tyr Trp Gly Gln Gly Thr Leu Val
        115                 120                 125

Thr Val Ser Ser Ala Ser
        130

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Asn Ile Tyr Tyr Ser Tyr Ile His
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Ile Tyr Ser Tyr Tyr Gly Tyr Thr Tyr Tyr Ala Asp Ser Val Lys
```

<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Arg Ser Pro Gly Pro Tyr Ala Val Cys Gly Asn Leu Phe Arg Ser
1               5                   10                  15

Val Ser Tyr Gly Met Asp Tyr
            20

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Tyr Met His Trp Val Arg Gln Ala Pro Gly Lys Gly Leu Glu Trp Val
        35                  40                  45

Ala Ser Ile Tyr Pro Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Ala Trp Ser Pro Gly Leu Asp Tyr Trp Gly Gln Gly
            100                 105                 110

Thr Leu Val Thr Val Ser Ser Ala Ser
        115                 120

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Asn Ile Ser Tyr Tyr Tyr Met His
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Ser Ile Tyr Pro Ser Ser Gly Ser Thr Tyr Tyr Ala Asp Ser Val Lys
1               5                   10                  15
```

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Gly Phe Ala Trp Ser Pro Gly Leu Asp Tyr
1               5                   10
```

<210> SEQ ID NO 81
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Tyr
            20                  25                  30

Ser Ile His Trp Val Arg Gln Ala Pro Gly Lys Gly Leu Glu Trp Val
        35                  40                  45

Ala Tyr Ile Tyr Ser Tyr Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Pro Gly Gly Tyr His Phe Trp Gly Trp Trp Ser
            100                 105                 110

Ser Pro Tyr Ala Phe Asp Tyr Trp Gly Gln Gly Thr Leu Val Thr Val
        115                 120                 125

Ser Ser Ala Ser
    130
```

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Gly Phe Asn Ile Tyr Tyr Tyr Ser Ile His
1               5                   10
```

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Tyr Ile Tyr Ser Tyr Tyr Gly Ser Thr Tyr Ala Asp Ser Val Lys
1               5                   10                  15

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Gly Tyr Pro Gly Gly Tyr His Phe Trp Gly Trp Trp Ser Ser Pro
1               5                   10                  15

Tyr Ala Phe Asp Tyr
            20

<210> SEQ ID NO 85
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Ser
                20                  25                  30

Tyr Ile His Trp Val Arg Gln Ala Pro Gly Lys Gly Leu Glu Trp Val
            35                  40                  45

Ala Ser Ile Tyr Pro Tyr Ser Ser Thr Ser Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Trp Ser Ala Met Asp Tyr Trp Gly Gln Gly
            100                 105                 110

Thr Leu Val Thr Val Ser Ser Ala Ser
        115                 120

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Ile Tyr Pro Tyr Ser Ser Ser Thr Ser Tyr Ala Asp Ser Val Lys
1               5                   10                  15

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 87

Gly Gly Gly Ser Trp Ser Ala Met Asp Tyr
1               5                   10

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Gly Tyr Ser
                85                  90                  95

Ser Leu Ile Thr Phe Gly Gln Gly Thr Lys Val Glu Ile Lys Arg
            100                 105                 110

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Tyr Ser Tyr Gly Tyr Ser Ser Leu Ile Thr
1               5                   10

<210> SEQ ID NO 90
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Gly Pro His Tyr Ala
                85                  90                  95
```

```
Pro Ile Thr Phe Gly Gln Gly Thr Lys Val Glu Ile Lys Arg
            100                 105                 110

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gln Trp Gly Pro His Tyr Ala Pro Ile Thr
1               5                   10

<210> SEQ ID NO 92
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Pro Tyr Pro
                85                  90                  95

Ile Thr Phe Gly Gln Gly Thr Lys Val Glu Ile Lys Arg
            100                 105

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Tyr Ser Gly Pro Tyr Pro Ile Thr
1               5                   10

<210> SEQ ID NO 94
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
```

```
                    20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Val Ala Tyr Val
                85                  90                  95

Trp Leu Ile Thr Phe Gly Gln Gly Thr Lys Val Glu Ile Lys Arg
                100                 105                 110

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Tyr Ser Val Ala Tyr Val Trp Leu Ile Thr
1               5                   10

<210> SEQ ID NO 96
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile
                85                  90                  95

Thr Phe Gly Gln Gly Thr Lys Val Glu Ile Lys Arg
            100                 105

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Ser Ser Tyr Ser Leu Ile Thr
1               5

<210> SEQ ID NO 98
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Phe Pro Phe Thr
                85                  90                  95

Phe Gly Gln Gly Thr Lys Val Glu Ile Lys Arg
            100                 105

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Gln Ser Ser Phe Pro Phe Thr
1               5

<210> SEQ ID NO 100
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Pro Thr Ile Ser Ser Leu Gln Pro
65                  70                  75                  80

Glu Asp Phe Ala Thr Tyr Tyr Cys Gln Gln Ser Tyr Phe Ser Tyr Pro
                85                  90                  95

Ile Thr Phe Gly Gln Gly Thr Lys Val Glu Ile Lys Arg
            100                 105

<210> SEQ ID NO 101
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Ser Tyr Phe Ser Tyr Pro Ile Thr
1               5                   10

<210> SEQ ID NO 102
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Ala Pro Phe
                85                  90                  95

Thr Phe Gly Gln Gly Thr Lys Val Glu Ile Lys Arg
            100                 105

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Gln Ser Gly Tyr Ala Pro Phe Thr
1               5

<210> SEQ ID NO 104
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Gly His Tyr His Ser
                 85                  90                  95

Leu Ile Thr Phe Gly Gln Gly Thr Lys Val Glu Ile Lys Arg
            100                 105                 110

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Ser Gly His Tyr His Ser Leu Ile Thr
 1               5                  10

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
             35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Ser His Leu Ile Thr
                 85                  90                  95

Phe Gly Gln Gly Thr Lys Val Glu Ile Lys Arg
            100                 105

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Ala Ser His Leu Ile Thr
 1               5

<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Ser Trp Gly
                85                  90                  95

Tyr Leu Ile Thr Phe Gly Gln Gly Thr Lys Val Glu Ile Lys Arg
                100                 105                 110

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Trp Ser Ser Trp Gly Tyr Leu Ile Thr
1               5                   10

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Leu Ile Thr
                85                  90                  95

Phe Gly Gln Gly Thr Lys Val Glu Ile Lys Arg
                100                 105

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln His Tyr Ser Leu Ile Thr
1               5

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Tyr Pro Phe Thr
                85                  90                  95

Phe Gly Gln Gly Thr Lys Val Glu Ile Lys Arg
            100                 105

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Thr Phe Tyr Pro Phe Thr
1               5

<210> SEQ ID NO 114
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Tyr Met His Trp Val Arg Gln Ala Pro Gly Lys Gly Leu Glu Trp Val
        35                  40                  45

Ala Ser Ile Ser Ser Tyr Tyr Gly Tyr Thr Ser Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

```
Ala Arg Ser Pro Ile Val Tyr Tyr Glu Leu Phe Met Phe Ile Asp Met
            100                 105                 110

Gly Ala Gln Gly Trp Lys Tyr Gly Met Asp Tyr Trp Gly Gln Gly Thr
        115                 120                 125

Leu Val Thr Val Ser Ser Ala Ser
    130                 135

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Asn Leu Tyr Tyr Ser Tyr Met His
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Ile Ser Ser Tyr Tyr Gly Tyr Thr Ser Tyr Ala Asp Ser Val Lys
1               5                   10                  15

<210> SEQ ID NO 117
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Pro Ile Val Tyr Tyr Glu Leu Phe Met Phe Ile Asp Met Gly Ala
1               5                   10                  15

Gln Gly Trp Lys Tyr Gly Met Asp Tyr
            20                  25

<210> SEQ ID NO 118
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Ser His Tyr Ala Ser
                85                  90                  95

Pro Pro Ile Thr Phe Gly Gln Gly Thr Lys Val Glu Ile Lys Arg
            100                 105                 110

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln Ser Ser His Tyr Ala Ser Pro Pro Ile Thr
1               5                   10

<210> SEQ ID NO 120
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Ser
            20                  25                  30

Tyr Met His Trp Val Arg Gln Ala Pro Gly Lys Gly Leu Glu Trp Val
        35                  40                  45

Ala Ser Ile Tyr Pro Ser Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Leu Glu Glu Ser Leu Pro Lys Arg Ala Arg Thr Ala Val
            100                 105                 110

Ser Lys Glu Leu Glu Ser Val Pro Tyr Val Met Asp Tyr Trp Gly Gln
        115                 120                 125

Gly Thr Leu Val Thr Val Ser Ser Ala Ser
    130                 135

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Phe Asn Leu Ser Tyr Ser Tyr Met His
1               5                   10

<210> SEQ ID NO 122
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 122

Ser Ile Tyr Pro Ser Tyr Gly Ser Thr Tyr Tyr Ala Asp Ser Val Lys
1               5                   10                  15

<210> SEQ ID NO 123
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Leu Glu Glu Ser Leu Pro Lys Arg Ala Arg Thr Ala Val Ser Lys
1               5                   10                  15

Glu Leu Glu Ser Val Pro Tyr Val Met Asp Tyr
            20                  25

<210> SEQ ID NO 124
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Tyr Gly Tyr Leu
                85                  90                  95

Phe Thr Phe Gly Gln Gly Thr Lys Val Glu Ile Lys Arg
            100                 105

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gln Ala Tyr Tyr Gly Tyr Leu Phe Thr
1               5                   10

<210> SEQ ID NO 126
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Tyr
            20                  25                  30

Ser Met His Trp Val Arg Gln Ala Pro Gly Lys Gly Leu Glu Trp Val
        35                  40                  45

Ala Tyr Ile Tyr Pro Tyr Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Leu Leu Ser Ile Gly Lys Leu Phe Val Gly Asp Gly Ser
            100                 105                 110

Ile Leu His Val Trp Leu Tyr Gly Met Asp Tyr Trp Gly Gln Gly Thr
        115                 120                 125

Leu Val Thr Val Ser Ser Ala Ser
    130                 135

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Phe Asn Leu Ser Tyr Tyr Ser Met His
1               5                   10

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Ile Tyr Pro Tyr Tyr Gly Ser Thr Tyr Tyr Ala Asp Ser Val Lys
1               5                   10                  15

<210> SEQ ID NO 129
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Phe Leu Leu Ser Ile Gly Lys Leu Phe Val Gly Asp Gly Ser Ile Leu
1               5                   10                  15

His Val Trp Leu Tyr Gly Met Asp Tyr
            20                  25

<210> SEQ ID NO 130
<211> LENGTH: 286
<212> TYPE: PRT

<213> ORGANISM: Unknown
<220> FEATURE:
<223> OTHER INFORMATION: Description of Unknown:
TEM-1 sequence

<400> SEQUENCE: 130

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 131
<211> LENGTH: 199
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 131

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp

```
                35                  40                  45
Leu Asn Ser Gly Lys Ile Leu Glu Ser Phe Arg Pro Glu Arg Phe
 50                  55                  60
Pro Met Met Ser Thr Phe Lys Val Leu Leu Cys Gly Ala Val Leu Ser
 65                  70                  75                  80
Arg Ile Asp Ala Gly Gln Glu Gln Leu Gly Arg Ile His Tyr Ser
                 85                  90                  95
Gln Asn Asp Leu Val Glu Tyr Ser Pro Val Thr Glu Lys His Leu Thr
                100                 105                 110
Asp Gly Met Thr Val Arg Glu Leu Cys Ser Ala Ala Ile Thr Met Ser
                115                 120                 125
Asp Asn Thr Ala Ala Asn Leu Leu Leu Thr Thr Ile Gly Gly Pro Lys
 130                 135                 140
Glu Leu Thr Ala Phe Leu His Asn Met Gly Asp His Val Thr Arg Leu
 145                 150                 155                 160
Asp Arg Trp Glu Pro Glu Leu Asn Glu Ala Ile Pro Asn Asp Glu Arg
                165                 170                 175
Asp Thr Thr Met Pro Val Ala Met Ala Thr Thr Leu Arg Lys Leu Leu
                180                 185                 190
Thr Gly Ser Arg Gly Ser Gly
         195

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Arg Gly Ser Gly
 1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gly Arg Ile Gly Phe Leu Arg Thr Ala
 1               5                  10

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Pro Leu Gly Leu Glu Glu Ala Lys
 1               5

<210> SEQ ID NO 135
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 135

Glu Ile Ser Glu Val Lys Met Asp Ala Glu Tyr
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Leu Arg Ser Ser Lys Gln
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Leu His Phe Ser Lys Gln
1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Leu Pro Leu Gly Ile
1               5

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Ser Gly Pro Leu Gly Leu Glu Glu Ala Lys Ser Gly Gly
1               5                   10

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 140

His His His His His His
1               5
```

```
<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Lys(DNP)

<400> SEQUENCE: 141

Ser Glu Val Asn Leu Asp Ala Glu Phe Lys
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(DNP)

<400> SEQUENCE: 142

Lys Leu Arg Ser Ser Lys Gln Lys
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-Aminobenzoic acid
<220> FEATURE:
<221> NAME/KEY: MOD_RES
<222> LOCATION: (7)..(7)
<223> OTHER INFORMATION: Lys(DNP)

<400> SEQUENCE: 143

Xaa Gly Ile Val Arg Ala Lys
1               5

<210> SEQ ID NO 144
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Phe Lys Trp Arg Arg Ser Ala Gly Thr Val Lys Phe Tyr Val His
1               5                   10                  15

Glu Ala Tyr Gly Met Asp Tyr
            20

<210> SEQ ID NO 145
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 145

Val Thr Ser Asp Arg Val Gly Val Gly Arg Glu Ala Leu Arg Ala His
1               5                   10                  15

Ala Thr Leu Gly Tyr Ala Met Asp Tyr
            20                  25

<210> SEQ ID NO 146
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Leu Leu Ser Ser Thr Ile Phe Gln Ser His Thr Pro Leu Pro Thr
1               5                   10                  15

Leu Glu Gln Arg Tyr Ala Met Asp Tyr
            20                  25

<210> SEQ ID NO 147
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Lys Leu Glu Asn Pro Tyr Trp Ile Asp Leu Lys Asp Leu Ser Gln
1               5                   10                  15

Pro Thr Arg Met Tyr Gly Met Asp Tyr
            20                  25

<210> SEQ ID NO 148
<211> LENGTH: 158
<212> TYPE: PRT
<213> ORGANISM: Homo sapiens

<400> SEQUENCE: 148

Gly Pro Val Trp Arg Lys His Tyr Ile Thr Tyr Arg Ile Asn Asn Tyr
1               5                   10                  15

Thr Pro Asp Met Asn Arg Glu Asp Val Asp Tyr Ala Ile Arg Lys Ala
            20                  25                  30

Phe Gln Val Trp Ser Asn Val Thr Pro Leu Lys Phe Ser Lys Ile Asn
        35                  40                  45

Thr Gly Met Ala Asp Ile Leu Val Val Phe Ala Arg Gly Ala His Gly
    50                  55                  60

Asp Phe His Ala Phe Asp Gly Lys Gly Gly Ile Leu Ala His Ala Phe
65                  70                  75                  80

Gly Pro Gly Ser Gly Ile Gly Gly Asp Ala His Phe Asp Glu Asp Glu
                85                  90                  95

Phe Trp Thr Thr His Ser Gly Gly Thr Asn Leu Phe Leu Thr Ala Val
            100                 105                 110

His Glu Ile Gly His Ser Leu Gly Leu Gly His Ser Ser Asp Pro Lys
        115                 120                 125
```

```
Ala Val Met Phe Pro Thr Tyr Lys Tyr Val Asp Ile Asn Thr Phe Arg
    130                 135                 140

Leu Ser Ala Asp Asp Ile Arg Gly Ile Gln Ser Leu Tyr Gly
145                 150                 155
```

<210> SEQ ID NO 149
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Gly Pro Val Trp Arg Lys His Tyr Ile Thr Tyr Arg Ile Gln Asn Tyr
1               5                   10                  15

Thr Pro Asp Met Asn Arg Glu Asp Val Asp Glu Ala Ile Arg Lys Ala
                20                  25                  30

Phe Gln Val Trp Ser Asn Val Thr Pro Leu Lys Phe Ser Lys Ile Asn
            35                  40                  45

Thr Gly Glu Ala Asp Ile Leu Ile Val Phe Ala Arg Gly Ala His Gly
        50                  55                  60

Asp Asn His Pro Phe Asp Gly Lys Gly Gly Ile Leu Ala His Ala Phe
65                  70                  75                  80

Pro Pro Gly Ser Gly Ile Gly Gly Asp Ala His Phe Asp Glu Asp Glu
                85                  90                  95

Phe Trp Thr Thr Asp Ser Gly Gly Thr Asn Leu Phe Leu Val Ala Val
            100                 105                 110

His Glu Phe Gly His Ser Leu Gly Leu Gly His Ser Ser Asp Pro Lys
        115                 120                 125

Ala Val Met Phe Pro Thr Tyr Lys Tyr Val Asp Thr Asn Thr Phe Arg
    130                 135                 140

Leu Ser Ala Asp Asp Ile Arg Gly Ile Gln Ser Leu Tyr Gly
145                 150                 155
```

<210> SEQ ID NO 150
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Gly Pro Val Trp Arg Lys His Asp Ile Thr Tyr Arg Ile Gln Asn Tyr
1               5                   10                  15

Thr Pro Asp Met His Arg Glu Asp Val Asp Lys Ala Ile Glu Lys Ala
                20                  25                  30

Phe Gln Val Trp Ser Asn Val Thr Pro Leu Lys Phe Ser Lys Ile Asn
            35                  40                  45

Thr Gly Glu Ala Asp Ile Leu Ile Val Phe Ala Arg Gly Glu His Gly
        50                  55                  60

Asp Asn His Pro Phe Asp Gly Lys Gly Gly Ile Leu Ala His Ala Phe
65                  70                  75                  80

Pro Pro Gly Ser Gly Ile Gly Gly Asp Ala His Phe Asp Glu Asp Glu
                85                  90                  95

Phe Trp Thr Thr Ser Ser Gly Gly Tyr Asn Leu Phe Leu Val Ala Val
            100                 105                 110
```

His Glu Phe Gly His Ser Leu Gly Leu Gly His Ser Ser Asp Pro Arg
            115                 120                 125

Ala Val Met Phe Pro Thr Tyr Lys Tyr Val Asp Thr Asn Thr Phe Arg
    130                 135                 140

Leu Ser Gln Asp Asp Ile Arg Gly Ile Gln Ser Leu Tyr Gly
145                 150                 155

<210> SEQ ID NO 151
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gly Pro Val Trp Asn Lys Asn Asp Ile Thr Tyr Arg Ile Gln Asn Tyr
1               5                   10                  15

Thr Pro Asp Met His Arg Asp Val Asp Lys Ala Ile Glu Lys Ala
            20                  25                  30

Phe Gln Val Trp Ser Asp Val Thr Pro Leu Thr Phe Thr Lys Ile Tyr
            35                  40                  45

Ser Gly Glu Ala Asp Ile Leu Ile Val Phe Ala Arg Gly Glu His Gly
    50                  55                  60

Asp Asn His Pro Phe Asp Gly Lys Gly Ile Leu Ala His Ala Phe
65                  70                  75                  80

Pro Pro Gly Ser Gly Ile Gly Gly Asp Ala His Phe Asp Glu Asp Glu
                85                  90                  95

Phe Trp Thr Thr Asp Ser Gly Gly Val Asn Leu Phe Leu Val Ala Val
                100                 105                 110

His Glu Phe Gly His Ser Leu Gly Leu Gly His Ser Asn Asp Pro Arg
            115                 120                 125

Ala Ile Met Tyr Pro Thr Tyr Lys Tyr Val Asp Thr Asn Thr Phe Arg
    130                 135                 140

Leu Ser Gln Asp Asp Ile Arg Gly Ile Gln Ser Leu Tyr Gly
145                 150                 155

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ser Gly Gly Pro Trp
1               5

<210> SEQ ID NO 153
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ser Gly Gly Pro Trp Glu Leu Leu Thr Leu Ala Ser Arg Gln Gln Leu
1               5                   10                  15

Ile Asp Trp Met Glu Ala Asp Lys Val Ala Gly Pro Leu Leu Arg Ser

-continued

```
            20                  25                  30
Ala Leu Pro Ala Gly Trp Phe Ile Ala Asp Lys Ser Gly Ala Gly Glu
            35                  40                  45

Arg Gly Ser Arg Gly Ile Ile Ala Ala Leu Gly Pro Asp Gly Lys Pro
            50                  55                  60

Ser Arg Ile Val Val Ile Tyr Thr Thr Gly Ser Gln Ala Thr Met Asp
65                  70                  75                  80

Glu Arg Asn Arg Gln Ile Ala Glu Ile Gly Ala Ser Leu Ile Lys His
            85                  90                  95

Trp
```

PROTEASE INHIBITORY ANTIBODIES AND METHODS OF USE THEREOF

RELATED APPLICATION

This application claims the benefit of priority of U.S. Provisional Application Ser. No. 62/850,914 filed on May 21, 2019, which application is incorporated by reference herein.

GOVERNMENT FUNDING

This invention was made with government support under GM115672 awarded by the National Institutes of Health and CBET-1453645 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Aug. 7, 2020, is named 12111_013US1_SL.txt and is 88,748 bytes in size.

BACKGROUND OF THE INVENTION

Accounting for ~1% of the human genome, extracellular proteases are important signaling molecules that exist in a delicate balance to maintain systematic homeostasis (Turk B, et al., *EMBO J.* 31, 1630-1643 (2012); Deu, et al., *Nat Struct Mol Biol.* 19, 9-16 (2012)). Dysregulation of proteolysis causes a variety of disorders ranging from cancer, inflammation, and osteoporosis to neuropathic pain and degenerative diseases (López-Otin C1, Matrisian L M. *Nat Rev Cancer.* 7, 800-808 (2007); Prassas, et al., *Nat Rev Drug Discov.* 14, 183-202 (2015); Troeberg et al., *Biochim Biophys Acta.* 1824, 133-145 (2012); Ji et al., *Trends Pharmacol Sci.* 30, 336-340 (2009); De Strooper B. *Physiol Rev.* 90, 465-494 (2010)). Conventional drug discovery strategies led to protease inhibitors currently on the market targeting a small fraction of therapeutically relevant proteases (Drag M, Salvesen G S. *Nat Rev Drug Discov.* 9, 690-701 (2010); Turk B. *Nat Rev Drug Discov.* 5, 785-799 (2006)). Small molecule inhibitors are often limited by lack of specificity and/or appropriate pharmacokinetic properties required for a successful protease inhibition therapy (Overall C M, Kleifeld O. *Br J Cancer.* 94, 941-946 (2006); Vandenbroucke R, Libert C. *Nat Rev Drug Discov.* 13, 904-927 (2014); Vassar R. *Alzheimers Res Ther.* 6, 89 (2014)). Conversely, biologics, e.g. monoclonal antibodies (mAbs) provide exquisite specificity capable of distinguishing between closely related protease family members (Wu, et al., *Proc Natl Acad Sci USA.* 104, 19784-19789 (2007); Devy et al., *Cancer Res.* 69, 1517-1526 (2009); Atwal, et al., *Sci Transl Med.* 3, 84ra43 (2011); Schneider et al., *J Mol Biol.* 415, 699-715 (2012); Kenniston et al., *J Biol Chem.* 289, 23596-608 (2014); David et al., *Sci Transl Med.* 8, 353ra112 (2016); Nam et al., *Proc Natl Acad Sci USA* 113, 14970-14975 (2016)). Their stability in serum, potential to cross blood-brain barrier, novel design as prodrugs, and improved effector functions offer significant advantages over the small-molecule approach (Yu et al., *Sci Transl Med.* 6, 261ra154 (2014); Sharma S K, Bagshawe K D. *Adv Drug Deliv Rev.* 118, 2-7 (2017); Wang et al., *Protein Cell.* 9, 63-73 (2018)). However, current mAb discovery technologies such as hybridoma, phage panning, and cell surface display coupled flow cytometry, all rely on affinity-based selection/screening. Consequently, valuable inhibitory clones tend to be lost during the process, and there is a high level of probability that very few, or even none, of the isolated binders are inhibitory. Furthermore, generated mAbs often exhibit suboptimal inhibition properties and are vulnerable to be cleaved by the protease target. Thus, new methods for the rapid and effective identification of protease inhibitory antibodies are needed. Additionally, there is a need for new protease inhibitory antibodies, in particular, antibodies that inhibit MMP-14, MMP-12, BACE-1, Alp2 and cathepsin B.

SUMMARY OF THE INVENTION

Certain embodiments provide an isolated anti-matrix metalloproteinase-14 (MMP-14) antibody or fragment thereof, comprising one or more complementarity determining regions (CDRs) selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQYSYGYSSLIT (SEQ ID NO:89), QQWGPHYAPIT (SEQ ID NO:91), QQYSGPYPIT (SEQ ID NO:93), QQYSVAYVWLIT (SEQ ID NO:95), QQSSYSLIT (SEQ ID NO:97), and QQSSFPFT (SEQ ID NO:99);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNLYSSYIH (SEQ ID NO:2), GFNIYYSSMH (SEQ ID NO:6), GFNLYYYYMH (SEQ ID NO:10), GFNIYYSYMH (SEQ ID NO:14), GFNISSSSMH (SEQ ID NO:18) and GFNFSSSSIH (SEQ ID NO:22);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SIYSSYSSTYYADSVK (SEQ ID NO:3), YIYSSSYTYYADSVK (SEQ ID NO:7), YIYPYSGSTYYADSVK (SEQ ID NO:11), SIYPSYGYTYYADSVK (SEQ ID NO:15), SIYPYYGYTYYADSVK (SEQ ID NO:19) and SISSYGYTYYADSVK (SEQ ID NO:23);

(f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SDSAVYSVRRMGSSGLAAYAMDY (SEQ ID NO:4), DCCSCVFSQSAGITLACVYVMDY (SEQ ID NO:8), LDFLMRDIYYDLGGGALGWLIKYAMDY (SEQ ID NO:12), QLFACWRQSILTPPLLSAMMMGYAMDY (SEQ ID NO:16), GVTRFTNDASVGQVWAGAYGMDY (SEQ ID NO:20) and VVRMLPVRCIPRCIKTTLPLYGMDY (SEQ ID NO:24).

Certain embodiments provide an isolated anti-BACE-1 antibody or fragment thereof, comprising one or more complementarity determining regions (CDRs) selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of RASQSVGTYLN (SEQ ID NO:26) and RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of ATSNLRS (SEQ ID NO:27) and SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQSYSIPRFT (SEQ ID NO:28), QQASASPYALIT (SEQ ID NO:36), QQSYFSYPIT (SEQ ID NO:101), QQYGYYLIT (SEQ ID NO:45), QQSGYAPFT (SEQ ID NO:103), QQSSYSLIT (SEQ ID NO:97), and QQSGHYHSLIT (SEQ ID NO:105);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNIPYSSMH (SEQ ID NO:30), GFNISYSSIH (SEQ ID NO:38), GFNIYYSYMH (SEQ ID NO:14), GFNISSYYMH (SEQ ID NO:47), GFNISYSSMH (SEQ ID NO:54), GFNIYSSSMH (SEQ ID NO:58) and GFNISYYSMH (SEQ ID NO:62);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SISSYSSSTSYADSVK (SEQ ID NO:31), YISPSSSYTSYADSVK (SEQ ID NO:39), SIYPYYGSTYYADSVK (SEQ ID NO:42), SIYSSYGYTYYADSVK (SEQ ID NO:48), YISSYSSSTYYADSVK (SEQ ID NO:51), SIYPSYSYTSYADSVK (SEQ ID NO:55), YIYSSYGYTYYADSVK (SEQ ID NO:59) and SISPYYGSTYYADSVK (SEQ ID NO:63); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of YICGHRWRDFDMWRARTGVNYAMDY (SEQ ID NO:32), HYYVSVGSGIDY (SEQ ID NO:40), WHGYPPGYSYYSSFSSSGFDY (SEQ ID NO:43) YWGYYAWFGSHPWAYGAFDY (SEQ ID NO:49), SASGIDY (SEQ ID NO:52), SSSSYYYGMDY (SEQ ID NO:56), DNSICVLTQKEVDTKFLVGQHSYVMDY (SEQ ID NO:60) and ERSSCPVGWRDSRFGADGYGLEY (SEQ ID NO:64).

Certain embodiments provide an isolated anti-Alp2 antibody or fragment thereof, comprising one or more complementarity determining regions (CDRs) selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of QQASHLIT (SEQ ID NO:107);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNISSYYIH (SEQ ID NO:66), GFNLSSSSMH (SEQ ID NO:70) and GFNIYYSYIH (SEQ ID NO:74);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SIYSYSSYTYYADSVK (SEQ ID NO:67), SIYPSYSYTYYADSVK (SEQ ID NO:71) and SIYSYYGYTYYADSVK (SEQ ID NO:75);

(f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of FGSWSYAIDY (SEQ ID NO:68), KTSDQYLLVGGSFFKLRDCCYVMDY (SEQ ID NO:72) and GRSPGPYAVCGNLFRSVSYGMDY (SEQ ID NO:76).

Certain embodiments provide an isolated anti-cathepsin B antibody or fragment thereof, comprising one or more complementarity determining regions (CDRs) selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQWSSSWGYLIT (SEQ ID NO:109); and QQHYSLIT (SEQ ID NO:111);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNISYYYMH (SEQ ID NO:78), GFNIYYYSIH (SEQ ID NO:82) and GFNLYSSYIH (SEQ ID NO:2);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SIYPSSGSTYYADSVK (SEQ ID NO:79), YIYSYYGSTYYADSVK (SEQ ID NO:83) and SIYPYSSSTSYADSVK (SEQ ID NO:86); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFAWSPGLDY (SEQ ID NO:80), YGYPG- GYHFWGWWSSPYAFDY (SEQ ID NO:84) and GGGSWSAMDY (SEQ ID NO:87).

Certain embodiments provide an isolated anti-MMP-12 antibody or fragment thereof, comprising one or more complementarity determining regions (CDRs) selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQTFYPFT (SEQ ID NO:113); QQSSHYASPPIT (SEQ ID NO:119), and QQAYYGYLFT (SEQ ID NO:125);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one GFNLYYSYMH (SEQ ID NO:115); GFNLSYSYMH (SEQ ID NO:121), and GFNLSYYSMH (SEQ ID NO:127);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SISSYYGYTSYADSVK (SEQ ID NO:116), SIYPSYGSTYYADSVK (SEQ ID NO:122), and YIYPYYGSTYYADSVK (SEQ ID NO:128); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one SPIVYYELFMFIDMGAQGWKYGMDY (SEQ ID NO:117), DLEESLPKRARTAVSKELESVPYVMDY (SEQ ID NO:123), and FLLSIGKLFVGDGSILHVWLYGMDY (SEQ ID NO:129).

Certain embodiments provide a composition comprising an antibody, or fragment thereof, as described herein and a carrier.

Certain embodiments provide an isolated polynucleotide comprising a nucleotide sequence encoding the isolated antibody, or fragment thereof, as described herein.

Certain embodiments provide a vector comprising the polynucleotide described herein.

Certain embodiments provide a cell comprising a polynucleotide or a vector as described herein.

Certain embodiments provide a method of detecting the presence of a target protease in a cell, the method comprising contacting the cell with an isolated antibody as described herein, or fragment thereof, and detecting whether a complex is formed between the antibody and the target protease, wherein the target protease is selected from the group consisting of MMP-14, MMP-12, BACE-1, Alp2 and cathepsin B.

Certain embodiments provide a method of inhibiting the activity of a target protease, comprising contacting the target protease with an isolated antibody, or fragment thereof, as described herein, wherein the target protease is selected from the group consisting of MMP-14, MMP-12, BACE-1, Alp2 and cathepsin B.

Certain embodiments provide a method for treating a disease or disorder in a mammal, comprising administering an effective amount of an isolated antibody, or fragment thereof, as described herein, to the mammal.

Certain embodiments provide an isolated antibody, or fragment thereof, as described herein for the prophylactic or therapeutic treatment of a disease or disorder.

Certain embodiments provide the use of an isolated antibody, or fragment thereof, as described herein to prepare a medicament for the treatment of a disease or disorder in a mammal.

Certain embodiments provide an isolated antibody, or fragment thereof, as described herein for use in medical therapy.

Certain embodiments provide a kit comprising an isolated antibody, or fragment thereof, as described herein, packaging material, and instructions for administering the antibody, or a fragment thereof, to a mammal to treat a disease or disorder (e.g., cancer, Alzheimer's disease, aspergillosis, an inflammatory, or a neurological condition). In certain embodiments, the kit further comprises at least one other therapeutic agent.

Certain embodiments provide a method of isolating an antibody or a fragment thereof from an antibody library, wherein the antibody or fragment thereof is capable of inhibiting a target protease, the method comprising: periplasmically co-expressing in a bacterial cell: 1) an antibody, or fragment thereof, from the library; 2) the target protease or an enzymatic domain thereof (e.g., extracellular or catalytic domain); and 3) a modified β-lactamase that comprises a peptide sequence that is capable of being cleaved by the target protease; wherein the bacterial cell is cultured in the presence of a β-lactam antibiotic.

The invention also provides processes and intermediates disclosed herein that are useful for preparing antibodies, or fragments thereof, and compositions described herein.

BRIEF DESCRIPTION OF THE FIGURES

(FIG. 1A) Scheme showing that three recombinant proteins are simultaneously co-expressed in the periplasmic space of *E. coli*—a clone from the Fab library, the protease of interest, and the modified β-lactamase TEM-1 with a cleavable peptide insertion. The protease extracellular/catalytic domain under a lac promoter and TEM-1 under its native promoter are cloned into a low copy number (p15A ori) plasmid of chloramphenicol resistance (CmR). The antibody Fab library under a phoA promoter is cloned into a medium copy number (pBR322 ori) plasmid carrying kanamycin resistance (KanR). If the Fab has no inhibition, the protease will cleave TEM-1 leading to cell death in the presence of ampicillin. An inhibitory Fab blocks proteolytic activity which allows TEM-1 to remain intact, resulting in cell growth on ampicillin plates. (FIG. 1B) Selection windows for BACE1 inhibitors. TEM-1 was modified by inserting the protease specific cleavage peptide sequences (shown in parentheses (SEQ ID NOs: 135 and 135, respectively, in order of appearance)) between Gly196 and Glu197 of TEM-1 (FIG. 6). Survival curves of *E. coli* cells transformed with modified TEM-1 were measured (solid), and compared to those for cells also co-expressing the associated proteases (dashed). Survival curve of wt TEM-1 is shown. The experiments were repeated three times.

(FIG. 4A) Fab A4A1 blocked Alp2 from hydrolyzing FITC-conjugated type I collagen. (FIG. 4B) Inhibition of $A\beta_{40}$ formation by IgG B2B2 in cellular assays. HEK293F cell cultures expressing $APP_{571-696}$ were incubated with IgG for 72 hours. Generated $A\beta_{40}$ was measured by ELISA.

(FIG. 13A) Structure of modified D4 shown in standard orientation (left) and 180° rotation around y-axis (right). Accepted mutations are shown and rejected mutations (remain as the wild type) are underlined in FIG. 13A and with a "+" in FIG. 13B. The three His residues coordinating the catalytic zinc, the catalytic Glu and the conserved Met-turn are shown with a "*" in FIG. 13B. (FIG. 13B) Amino acid sequences of cdMMP-12 wild type, and mutants D1, D4 and D7. In modified designs, F171, G186, T210 and I220 are remained as the wild type. Figure discloses SEQ ID NOS 148-151, respectively in order of appearance.

(FIG. 14A) Conceptual scheme showing $E.$ $coli$ periplasmic co-expression of MMP-12, an antibody Fab library, and a modified β-lactamase TEM-1 carrying a cleavable peptide insert. When Fab is inhibitory, it blocks activity of cdMMP-12 from cleaving modified TEM-1 and thus leading cellular resistance to ampicillin. In contrast, non-inhibitory Fabs result in cleavage of modified TEM-1 and cell death in the presence of ampicillin. (FIG. 14B) Survival curves of $E.$ $coli$ cells carrying modified TEM-1 with (squares) or without (triangles) co-expression of D4. Results of wt TEM-1 is shown for comparison (circles). TEM-1 was modified by inserting a cleavage peptide sequence (PLGLEEAK (SEQ ID NO:134)) between Gly196 and Glu197. Cells were grown on 2×YT agar plates.

(FIG. 17A) 6 µM Fab LG4, LH6, or LH11 with 350 nM cdMMP-12 wt. (FIG. 17B) 0.1-1 µM Fab LH11 with 200 nM cdMMP-12 wt. Assays were conducted in 50 mM HEPES, 150 mM NaCl pH 7.5 at 37° C. for 2 h with 200 nM fibronectin. Western blotting was developed with anti-fibronectin-HRP. Relative quantities were analyzed by densitometric analysis. 2 µM GM6001 was used as control.

(FIG. 18A) Lineweaver-Burk plots of 10 nM D4 with 0.3-2 µM FRET peptide in the presence of 31-500 nM tested Fabs. (FIG. 18B) Proteolytic stability of 2 µM Fabs after incubation with 2 µM cdMMP-12 wt or mutant D4 for 4 h at 50 mM HEPES, 150 mM NaCl (pH 7.5) at 37° C.

DETAILED DESCRIPTION

Figures 1A, 1B:
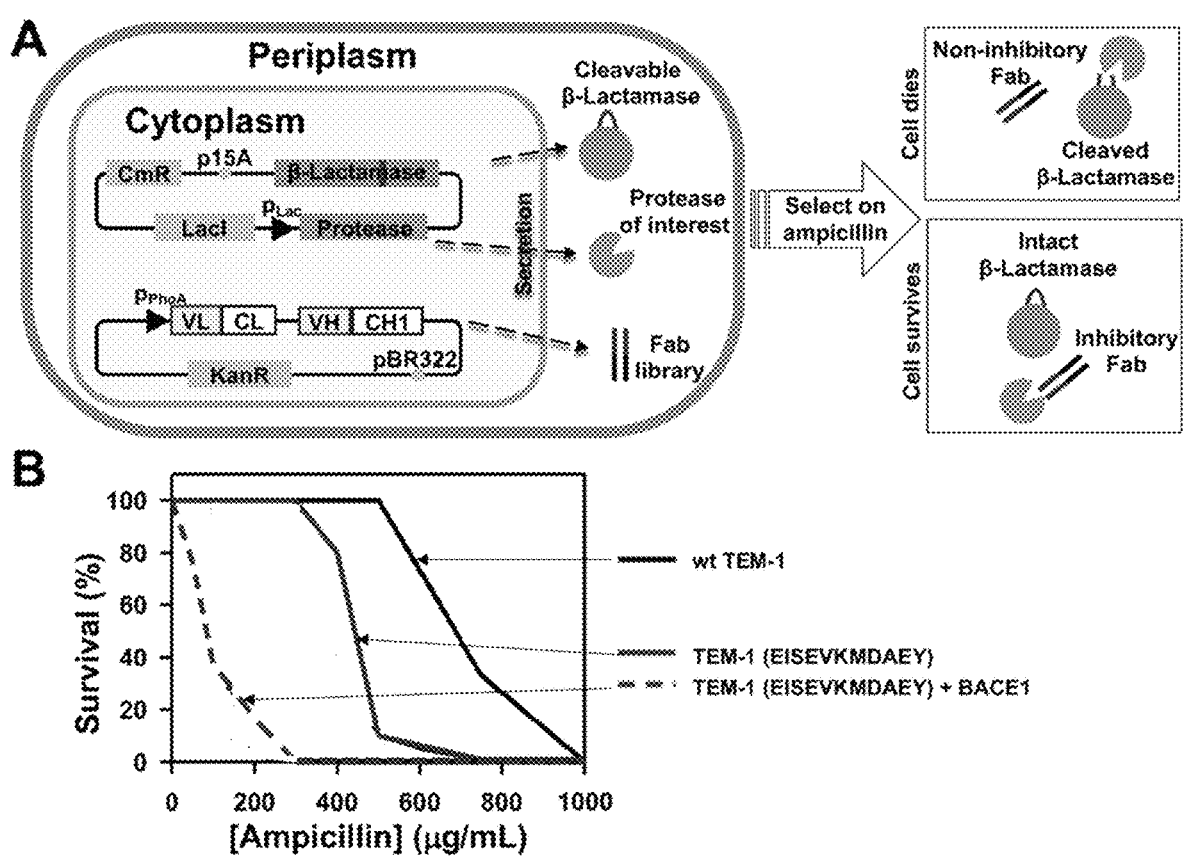
FIGS. 1A-1B. Functional selection for protease inhibitory antibodies.

Proteases represent one of the largest families of pharmaceutical targets. To inhibit pathogenic proteases with desired selectivity, monoclonal antibodies (mAbs) hold a great promise as research tools and therapeutic agents. However, identification of mAbs with inhibitory functions is challenging because current antibody discovery methods rely on binding rather than inhibition. This study developed a highly efficient selection method for protease inhibitory mAbs by co-expressing three recombinant proteins in the periplasmic space of *Escherichia coli*—an antibody clone, a protease of interest, and a β-lactamase modified by insertion of a protease cleavable peptide sequence. During functional selection, inhibitory antibodies prevent the protease from cleaving the modified β-lactamase thereby allowing the cell to survive in the presence of ampicillin. Using this method to select from synthetic human antibody libraries, we isolated panels of mAbs inhibiting four targets, representing main protease classes: matrix metalloproteinases (MMP-14, a predominant target in metastasis), beta-secretase 1 (BACE1, an aspartic protease involved in Alzheimer's disease), cathepsin B (a cysteine protease involved in cancer), and Alp2 (a serine protease involved in aspergillosis) (see, Example 1). Notably, a large percentage of the identified binders were inhibitory. Certain isolated mAb inhibitors exhibited nanomolar potency, exclusive selectivity, excellent proteolytic stability, and desired biological functions. For example, anti-Alp2 Fab A4A1 had a binding affinity of 11 nM and inhibition potency of 13 nM and anti-BACE1 IgG B2B2 reduced amyloid beta ($A\beta_{40}$) production by 80% in cellular assays. As described in Example 2, a similar method was used to identify anti-MMP-12 antibodies.

Anti-MMP-14 Antibodies or Fragments Thereof

Accordingly, certain embodiments provide antibodies and antigen-binding portions of antibodies that specifically bind to MMP-14 (i.e., an anti-MMP-14 antibody, or fragment thereof). Human matrix metalloproteinase (MMP)-14 (Gene ID=4323), is a membrane-bound zinc endopeptidase. MMP-14 is recognized as an important cancer target, playing a role in tumor growth and invasion.

In some embodiments, an anti-MMP-14 antibody, or fragment thereof, comprises: (1) one or more complementarity determining region (CDR) sequences; (2) a heavy chain variable region sequence; and/or (3) a light chain variable region sequence, as described herein (e.g., as described in Table 8 below).

In certain embodiments, an isolated anti-MMP-14 antibody or fragment thereof, comprises one or more CDRs selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQYSYGYSSLIT (SEQ ID NO:89), QQWGPHYAPIT (SEQ ID NO:91), QQYSGPYPIT (SEQ ID NO:93), QQYSVAYVWLIT (SEQ ID NO:95), QQSSYSLIT (SEQ ID NO:97), and QQSSFPFT (SEQ ID NO:99);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNLYSSYIH (SEQ ID NO:2), GFNIYYSSMH (SEQ ID NO:6), GFNLYYYYMH (SEQ ID NO:10), GFNIYYSYMH (SEQ ID NO:14), GFNISSSSMH (SEQ ID NO:18) and GFNFSSSSIH (SEQ ID NO:22);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SIYSSYSSTYYADSVK (SEQ ID NO:3), YIYSSSSYTYYADSVK (SEQ ID NO:7), YIYPYSGSTYYADSVK (SEQ ID NO:11), SIYPSYGYTYYADSVK (SEQ ID NO:15), SIYPYYGYTYYADSVK (SEQ ID NO:19) and SISSSYGYTYYADSVK (SEQ ID NO:23); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SDSAVYSVRRMGSSGLAAYAMDY (SEQ ID NO:4), DCCSCVFSQSAGITLACVYVMDY (SEQ ID NO:8), LDFLMRDIYYDLGGGALGWLIKYAMDY (SEQ ID NO:12), QLFACWRQSILTPPLLSAMMMGYAMDY (SEQ ID NO:16), GVTRFTNDASVGQVWAGAYGMDY (SEQ ID NO:20) and VVRMLPVRCIPRCIKTTLPLYGMDY (SEQ ID NO:24).

In some embodiments, an anti-MMP-14 antibody, or fragment thereof, comprises two, three, four, five or six CDRs as described above (e.g., each CDR is selected from one of (a)-(f); or from one of (d)-(f)).

In certain embodiments, the anti-MMP-14 antibody, or fragment thereof, as described herein comprises one or more CDRs selected from the group consisting of:

(a) a light chain CDR1 comprising the amino acid sequence of any one of SEQ ID NO:34;

(b) a light chain CDR2 comprising the amino acid sequence of any one of SEQ ID NO:35; and (c) a light chain CDR3 comprising the amino acid sequence of any one of SEQ ID NOs:89, 91, 93, 95, 97, and 99;

(d) a heavy chain CDR1 comprising the amino acid sequence of any one of SEQ ID NOs:2, 6, 10, 14, 18 and 22;

(e) a heavy chain CDR2 comprising the amino acid sequence of any one of SEQ ID NOs:3, 7, 11, 15, 19, and 23; and (f) a heavy chain CDR3 comprising the amino acid sequence of any one of SEQ ID NOs:4, 8, 12, 16, 20 and 24.

In some embodiments, an anti-MMP-14 antibody, or fragment thereof, comprises two, three, four, five or six CDRs as described above (e.g., each CDR is selected from one of (a)-(f); or from one of (d)-(f)).

In some embodiments, an anti-MMP-14 antibody, or a fragment thereof, comprises a light chain sequence, or a fragment thereof, and/or a heavy chain sequence, or a fragment thereof, derived from any of the following antibodies described herein: 2B4, 2B12, 1A5, 2B10, 2D9 and 2A6. The amino acid sequences of the light chain variable region (VL) and heavy chain variable region (VH) of these anti-MMP-14 antibody clones are set forth in Table 8 below.

In certain embodiments, an anti-MMP-14 antibody, or a fragment thereof, comprises a VL as in any of the embodiments provided herein, and/or a VH as in any of the embodiments provided herein.

In certain embodiments, an anti-MMP-14 antibody described herein, or fragment thereof, comprises a light chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

(a)
(SEQ ID NO: 88)
DIQMTQSPSSLSASVGDRVTITCRASQSVSSAVAWYQQKPGKAPKLLIYS
ASSLYSGVPSRFSGSRSGTDFTLTISSLQPEDFATYYCQQYSYGYSSLIT
FGQGTKVEIKR;

(b)
(SEQ ID NO: 90)
DIQMTQSPSSLSASVGDRVTITCRASQSVSSAVAWYQQKPGKAPKLLIYS
ASSLYSGVPSRFSGSRSGTDFTLTISSLQPEDFATYYCQQWGPHYAPITF
GQGTKVEIKR;

(c)
(SEQ ID NO: 92)
DIQMTQSPSSLSASVGDRVTITCRASQSVSSAVAWYQQKPGKAPKLLIYS
ASSLYSGVPSRFSGSRSGTDFTLTISSLQPEDFATYYCQQYSGPYPITFG
QGTKVEIKR;

(d)
(SEQ ID NO: 94)
DIQMTQSPSSLSASVGDRVTITCRASQSVSSAVAWYQQKPGKAPKLLIYS
ASSLYSGVPSRFSGSRSGTDFTLTISSLQPEDFATYYCQQYSVAYVWLIT
FGQGTKVEIKR;

(e)
(SEQ ID NO: 96)
DIQMTQSPSSLSASVGDRVTITCRASQSVSSAVAWYQQKPGKAPKLLIYS
ASSLYSGVPSRFSGSRSGTDFTLTISSLQPEDFATYYCQQSSYSLITFGQ
GTKVEIKR;
and (f)
(SEQ ID NO: 98)
DIQMTQSPSSLSASVGDRVTITCRASQSVSSAVAWYQQKPGKAPKLLIYS
ASSLYSGVPSRFSGSRSGTDFTLTISSLQPEDFATYYCQQSSFPFTFGQG
TKVEIKR.

In some embodiments, an anti-MMP-14 antibody, or fragment thereof, comprises a light chain variable region comprising the amino acid sequence of any one of SEQ ID NOs:88, 90, 92, 94, 96 and 98. In some embodiments, an anti-MMP-14 antibody, or fragment thereof, comprises a light chain variable region consisting of the amino acid sequence of any one of SEQ ID NOs:88, 90, 92, 94, 96 and 98.

In certain embodiments, an isolated anti-MMP-14 antibody described herein, or fragment thereof, comprises a heavy chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

(a)
(SEQ ID NO: 1)
EVQLVESGGGLVQPGGSLRLSCAASGFNLYSSYIHWVRQAPGKGLE

WVASIYSSYSSTYYADSVKGRFTISADTSKNTAYLQMNSLRAEDTAVYYC

ARSDSAVYSVRRMGSSGLAAYAMDYWGQGTLVTVSSAS;

(b)
(SEQ ID NO: 5)
EVQLVESGGGLVQPGGSLRLSCAASGFNIYYSSMHWVRQAPGKGLE

WVAYIYSSSSYTYYADSVKGRFTISADTSKNTAYLQMNSLRAEDTAVYYC

ARDCCSCVFSQSAGITLACVYVMDYWGQGTLVTVSSAS;

(c)
(SEQ ID NO: 9)
EVQLVESGGGLVQPGGSLRLSCAASGFNLYYYYMEIWVRQAPGKGL

EWVAYIYPYSGSTYYADSVKGRFTISADTSKNTAYLQMNSLRAEDTAVYY

CARLDFLMRDIYYDLGGGALGWLIKYAMDYWGQGTLVTVSSAS;

(d)
(SEQ ID NO: 13)
EVQLVESGGGLVQPGGSLRLSCAASGFNIYYSYMEIWVRQAPGKGL

EWVASIYPSYGYTYYADSVKGRFTISADTSKNTAYLQMNSLRAEDTAVYY

CARQLFACWRQSILTPPLLSAMMMGYAMDYWGQGTLVTVSSAS;

(e)
(SEQ ID NO: 17)
EVQLVESGGGLVQPGGSLRLSCAASGFNISSSSMEIWVRQAPGKGL

EWVASIYPYYGYTYYADSVKGRFTISADTSKNTAYLQMNSLRAEDTAVYY

CARGVTRFTNDASVGQVWAGAYGMDYWGQGTLVTVSSAS;
and (SEQ ID NO: 21)
(f) EVQLVESGGGLVQPGGSLRLSCAASGFNFSSSSIHWVRQAPGKGLE

WVASISSSYGYTYYADSVKGRFTISADTSKNTAYLQMNSLRAEDTAVYYC

ARVVRMLPVRCIPRCIKTTLPLYGMDYWGQGTLVTVSSAS.

In some embodiments, an anti-MMP-14 antibody, or fragment thereof, comprises a heavy chain variable region comprising the amino acid sequence of any one of SEQ ID NOs:1, 5, 9, 13, 17 and 21. In some embodiments, an anti-MMP-14 antibody, or fragment thereof, comprises a heavy chain variable region consisting of the amino acid sequence of any one of SEQ ID NOs: 1, 5, 9, 13, 17 and 21.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:88, 90, 92, 94, 96 and 98 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:1, 5, 9, 13, 17 and 21.

In some embodiments, an anti-MMP-14 antibody, or fragment thereof, comprises a light chain variable region consisting of an amino acid sequence of SEQ ID NOs:88, 90, 92, 94, 96 and 98 and further comprises a heavy chain variable region consisting of an amino acid sequence of SEQ ID NOs:1, 5, 9, 13, 17 and 21.

Clone 2B4 In some embodiments, an anti-MMP-14 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:89. In some embodiments, an anti-MMP-14 antibody, or fragment thereof, comprises a heavy chain CDR1 comprising the amino acid sequence of SEQ ID NO:2, a heavy chain CDR2 comprising the amino acid sequence of SEQ ID NO:3, and a heavy chain CDR3 comprising the amino acid sequence of SEQ ID NO:4. In some embodiments, an anti-MMP-14 antibody, or fragment thereof, comprises a light chain CDR1-3 and a heavy chain CDR1-3 comprising the amino acid sequences of SEQ ID NOs:34, 35, 89, 2, 3 and 4, respectively. In some embodiments, an anti-MMP-14 antibody, or fragment thereof, comprises a light chain CDR1-3 and a heavy chain CDR1-3 consisting of the amino acid sequences of SEQ ID NOs:34, 35, 89, 2, 3 and 4, respectively.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:88. In some embodiments, an anti-MMP-14 antibody, or fragment thereof, comprises a light chain variable region comprising the amino acid sequence of SEQ ID NO:88. In some embodiments, an anti-MMP-14 antibody, or fragment thereof, comprises a light chain variable region consisting of the amino acid sequence of SEQ ID NO:88.

In some embodiments, an anti-MMP-14 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:1. In some embodiments, an anti-MMP-14 antibody, or fragment thereof, comprises a heavy chain variable region comprising the amino acid sequence of SEQ ID NO:1. In some embodiments, an anti-MMP-14 antibody, or fragment thereof, comprises a heavy chain variable region consisting of the amino acid sequence of SEQ ID NO:1.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:88 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:1. In some embodiments, an anti-MMP-14 antibody, or fragment thereof, comprises a light chain variable region comprising the amino acid sequence of SEQ ID NO:88 and further comprises a heavy chain variable region comprising the amino acid sequence of SEQ ID NO:1. In some embodiments, an anti-MMP-14 antibody, or fragment thereof, comprises a light chain variable region consisting of the amino acid sequence of SEQ ID NO:88 and further comprises a heavy chain variable region consisting of the amino acid sequence of SEQ ID NO:1.

Clone 2B12

In some embodiments, an anti-MMP-14 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:91. In some embodiments, an anti-MMP-14 antibody, or fragment thereof, comprises a heavy chain CDR1 comprising the amino acid sequence of SEQ ID NO:6, a heavy chain CDR2 comprising the amino acid sequence of SEQ ID NO:7, and a heavy chain CDR3 comprising the amino acid sequence of SEQ ID NO:8. In some embodiments, an anti-MMP-14 antibody, or fragment thereof, comprises a light chain CDR1-3 and a heavy chain CDR1-3 comprising the amino acid sequences of SEQ ID NOs:34, 35, 91, 6, 7, and 8, respectively. In some embodiments, an anti-MMP-14 antibody, or fragment thereof, comprises a light chain CDR1-3 and a heavy chain CDR1-3 consisting of the amino acid sequences of SEQ ID NOs:34, 35, 91, 6, 7, and 8, respectively.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:90. In some embodiments, an anti-MMP-14 antibody, or fragment thereof, comprises a light chain variable region comprising the amino acid sequence of SEQ ID NO:90. In some embodiments, an anti-MMP-14 antibody, or fragment thereof, comprises a light chain variable region consisting of the amino acid sequence of SEQ ID NO:90.

In some embodiments, an anti-MMP-14 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:5. In some embodiments, an anti-MMP-14 antibody, or fragment thereof, comprises a heavy chain variable region comprising the amino acid sequence of SEQ ID NO:5. In some embodiments, an anti-MMP-14 antibody, or fragment thereof, comprises a heavy chain variable region consisting of the amino acid sequence of SEQ ID NO:5.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:90 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:5. In some embodiments, an anti-MMP-14 antibody, or fragment thereof, comprises a light chain variable region comprising the amino acid sequence of SEQ ID NO:90 and further comprises a heavy chain variable region comprising the amino acid sequence of SEQ ID NO:5. In some embodiments, an anti-MMP-14 antibody, or fragment thereof, comprises a light chain variable region consisting of the amino acid sequence of SEQ ID NO:90 and further comprises a heavy chain variable region consisting of the amino acid sequence of SEQ ID NO:5.

Clone 1A5

In some embodiments, an anti-MMP-14 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:93. In some embodiments, an anti-MMP-14 antibody, or fragment thereof, comprises a heavy chain CDR1 comprising the amino acid sequence of SEQ ID NO:10, a heavy chain CDR2 comprising the amino acid sequence of SEQ ID NO:11, and a heavy chain CDR3 comprising the amino acid sequence of SEQ ID NO:12. In some embodiments, an anti-MMP-14 antibody, or fragment thereof, comprises a light chain CDR1-3 and a heavy chain CDR1-3 comprising the amino acid sequences of SEQ ID NOs:34, 35, 93, 10, 11, and 12, respectively. In some embodiments, an anti-MMP-14 antibody, or fragment thereof, comprises a light chain CDR1-3 and a heavy chain CDR1-3 consisting of the amino acid sequences of SEQ ID NOs:34, 35, 93, 10, 11, and 12, respectively.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:92. In some embodiments, an anti-MMP-14 antibody, or fragment thereof, comprises a light chain variable region comprising the amino acid sequence of SEQ ID NO:92. In some embodiments, an anti-MMP-14 antibody, or fragment thereof, comprises a light chain variable region consisting of the amino acid sequence of SEQ ID NO:92.

In some embodiments, an anti-MMP-14 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:9. In some embodiments, an anti-MMP-14 antibody, or fragment thereof, comprises a heavy chain variable region comprising the amino acid sequence of SEQ ID NO:9. In some embodiments, an anti-MMP-14 antibody, or fragment thereof, comprises a heavy chain variable region consisting of the amino acid sequence of SEQ ID NO:9.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:92 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:9. In some embodiments, an anti-MMP-14 antibody, or fragment thereof, comprises a light chain variable region comprising the amino acid sequence of SEQ ID NO:92 and further comprises a heavy chain variable region comprising the amino acid sequence of SEQ ID NO:9. In some embodiments, an anti-MMP-14 antibody, or fragment thereof, comprises a light chain variable region consisting of the amino acid sequence of SEQ ID NO:92 and further comprises a heavy chain variable region consisting of the amino acid sequence of SEQ ID NO:9.

Clone 2B10

In some embodiments, an anti-MMP-14 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:95. In some embodiments, an anti-MMP-14 antibody, or fragment thereof, comprises a heavy chain CDR1 comprising the amino acid sequence of SEQ ID NO:14, a heavy chain CDR2 comprising the amino acid sequence of SEQ ID NO:15, and a heavy chain CDR3 comprising the amino acid sequence of SEQ ID NO:16. In some embodiments, an anti-MMP-14 antibody, or fragment thereof, comprises a light chain CDR1-3 and a heavy chain CDR1-3 comprising the amino acid sequences of SEQ ID NOs:34, 35, 95, 14, 15, and 16, respectively. In some embodiments, an anti-MMP-14 antibody, or fragment thereof, comprises a light chain CDR1-3 and a heavy chain CDR1-3 consisting of the amino acid sequences of SEQ ID NOs:34, 35, 95, 14, 15, and 16, respectively.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:94. In some embodiments, an anti-MMP-14 antibody, or fragment thereof, comprises a light chain variable region comprising the amino acid sequence of SEQ ID NO:94. In some embodiments, an anti-MMP-14 antibody, or fragment thereof, comprises a light chain variable region consisting of the amino acid sequence of SEQ ID NO:94.

In some embodiments, an anti-MMP-14 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:13. In some embodiments, an anti-MMP-14 antibody, or fragment thereof, comprises a heavy chain variable region comprising the amino acid sequence of SEQ ID NO:13. In some embodiments, an anti-MMP-14 antibody, or fragment thereof, comprises a heavy chain variable region consisting of the amino acid sequence of SEQ ID NO:13.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:94 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:13. In some embodiments, an anti-MMP-14 antibody, or fragment thereof, comprises a light chain variable region comprising the amino acid sequence of SEQ ID NO:94 and further comprises a heavy chain variable region comprising the amino acid sequence of SEQ ID NO:13. In some embodiments, an anti-MMP-14 antibody, or fragment thereof, comprises a light chain variable region consisting of the amino acid sequence of SEQ ID NO:94 and further comprises a heavy chain variable region consisting of the amino acid sequence of SEQ ID NO:13.

Clone 2D9

In some embodiments, an anti-MMP-14 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:97. In some embodiments, an anti-MMP-14 antibody, or fragment thereof, comprises a heavy chain CDR1 comprising the amino acid sequence of SEQ ID NO:18, a heavy chain CDR2 comprising the amino acid sequence of SEQ ID NO:19, and a heavy chain CDR3 comprising the amino acid sequence of SEQ ID NO:20. In some embodiments, an anti-MMP-14 antibody, or fragment thereof, comprises a light chain CDR1-3 and a heavy chain CDR1-3 comprising the amino acid sequences of SEQ ID NOs:34, 35, 97, 18, 19, and 20, respectively. In some embodiments, an anti-MMP-14 antibody, or fragment thereof, comprises a light chain CDR1-3 and a heavy chain CDR1-3 consisting of the amino acid sequences of SEQ ID NOs:34, 35, 97, 18, 19, and 20, respectively.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:96. In some embodiments, an anti-MMP-14 antibody, or fragment thereof, comprises a light chain variable region comprising the amino acid sequence of SEQ ID NO:96. In some embodiments, an anti-MMP-14 antibody, or fragment thereof, comprises a light chain variable region consisting of the amino acid sequence of SEQ ID NO:96.

In some embodiments, an anti-MMP-14 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:17. In some embodiments, an anti-MMP-14 antibody, or fragment thereof, comprises a heavy chain variable region comprising the amino acid sequence of SEQ ID NO:17. In some embodiments, an anti-MMP-14 antibody, or fragment thereof, comprises a heavy chain variable region consisting of the amino acid sequence of SEQ ID NO:17.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:96 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:17. In some embodiments, an anti-MMP-14 antibody, or fragment thereof, comprises a light chain variable region comprising the amino acid sequence of SEQ ID NO:96 and further comprises a heavy chain variable region comprising the amino acid sequence of SEQ ID NO:17. In some embodiments, an anti-MMP-14 antibody, or fragment thereof, comprises a light chain variable region consisting of the amino acid sequence of SEQ ID NO:96 and further comprises a heavy chain variable region consisting of the amino acid sequence of SEQ ID NO:17.

Clone 2A6

In some embodiments, an anti-MMP-14 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:99. In some embodiments, an anti-MMP-14 antibody, or fragment thereof, comprises a heavy chain CDR1 comprising the amino acid sequence of SEQ ID NO:22, a heavy chain CDR2 comprising the amino acid sequence of SEQ ID NO:23, and a heavy chain CDR3 comprising the amino acid sequence of SEQ ID NO:24. In some embodiments, an anti-MMP-14 antibody, or fragment thereof, comprises a light chain CDR1-3 and a heavy chain CDR1-3 comprising the amino acid sequences of SEQ ID NOs:34, 35, 99, 22, 23 and 24, respectively. In some embodiments, an anti-MMP-14 antibody, or fragment thereof, comprises a light chain CDR1-3 and a heavy chain CDR1-3 consisting of the amino acid sequences of SEQ ID NOs:34, 35, 99, 22, 23 and 24, respectively.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:98. In some embodiments, an anti-MMP-14 antibody, or fragment thereof, comprises a light chain variable region comprising the amino acid sequence of SEQ ID NO:98. In some embodiments, an anti-MMP-14 antibody, or fragment thereof, comprises a light chain variable region consisting of the amino acid sequence of SEQ ID NO:98.

In some embodiments, an anti-MMP-14 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:21. In some embodiments, an anti-MMP-14 antibody, or fragment thereof, comprises a heavy chain variable region comprising the amino acid sequence of SEQ ID NO:21. In some embodiments, an anti-MMP-14 antibody, or fragment thereof, comprises a heavy chain variable region consisting of the amino acid sequence of SEQ ID NO:21.

In some embodiments, an anti-MMP-14 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:98 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:21. In some embodiments, an anti-MMP-14 antibody, or fragment thereof, comprises a light chain variable region comprising the amino acid sequence of SEQ ID NO:98 and further comprises a heavy chain variable region comprising the amino acid sequence of SEQ ID NO:21. In some embodiments, an anti-MMP-14 antibody, or fragment thereof, comprises a light chain variable region consisting of the amino acid sequence of SEQ ID NO:98 and further comprises a heavy chain variable region consisting of the amino acid sequence of SEQ ID NO:21.

Anti-BACE-1 Antibodies or Fragments Thereof

Certain embodiments also provide antibodies and antigen-binding portions of antibodies that specifically bind to BACE-1 (i.e., an anti-BACE-1 antibody, or fragment thereof). BACE1 (β-secretase 1, Gene ID=23621) is a transmembrane aspartic protease that catalyzes the first step in the formation of amyloid β peptide from amyloid precursor protein. Amyloid β peptides are the main constituent of amyloid beta plaques, which accumulate in the brains of human Alzheimer's disease patients.

In some embodiments, an anti-BACE-1 antibody, or fragment thereof, comprises: (1) one or more complementarity determining region (CDR) sequences; (2) a heavy chain variable region sequence; and/or (3) a light chain variable region sequence (e.g., as described herein, such as in Table 8 below).

In certain embodiments, an isolated anti-BACE-1 antibody or fragment thereof, comprises one or more CDRs selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of RASQSVGTYLN (SEQ ID NO:26) and RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of ATSNLRS (SEQ ID NO:27) and SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQSYSIPRFT (SEQ ID NO:28), QQASASPYALIT (SEQ ID NO:36), QQSYFSYPIT (SEQ ID NO:101), QQYGYYLIT (SEQ ID NO:45), QQSGYAPFT (SEQ ID NO:103), QQSSYSLIT (SEQ ID NO:97), and QQSGHYHSLIT (SEQ ID NO:105);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNIPYSSMH (SEQ ID NO:30), GFNISYSSIH (SEQ ID NO:38), GFNIYYSYMH (SEQ ID NO:14), GFNISSYYMH (SEQ ID NO:47), GFNISYSSMH (SEQ ID NO:54), GFNIYSSSMH (SEQ ID NO:58) and GFNISYYSMH (SEQ ID NO:62);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SISSYSSSTSYADSVK (SEQ ID NO:31), YISPSSSYTSYADSVK (SEQ ID NO:39), SIYPYYGSTYYADSVK (SEQ ID NO:42), SIYSSYGYTYYADSVK (SEQ ID NO:48), YISSYSSSTYYADSVK (SEQ ID NO:51), SIYPSYSYTSYADSVK (SEQ ID NO:55), YIYSSYGYTYYADSVK (SEQ ID NO:59) and SISPYYGSTYYADSVK (SEQ ID NO:63); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of YICGHRWRDFDMWRARTGVNYAMDY (SEQ ID NO:32), HYYVSVGSGIDY (SEQ ID NO:40), WHGYPPGYSYYSSFSSSGFDY (SEQ ID NO:43) YWGYYAWFGSHPWAYGAFDY (SEQ ID NO:49), SASGIDY (SEQ ID NO:52), SSSSYYYGMDY (SEQ ID NO:56), DNSICVLTQKEVDTKFLVGQHSYVMDY (SEQ ID NO:60) and ERSSCPVGWRDSRFGADGYGLEY (SEQ ID NO:64).

In some embodiments, an anti-BACE-1 antibody, or fragment thereof, comprises two, three, four, five or six CDRs as described above (e.g., each CDR is selected from one of (a)-(f)).

In certain embodiments, the anti-BACE-1 antibody, or fragment thereof, as described herein comprises one or more CDRs selected from the group consisting of:

(a) a light chain CDR1 comprising the amino acid sequence of any one of SEQ ID NOs:26 and 34;

(b) a light chain CDR2 comprising the amino acid sequence of any one of SEQ ID NOs:27 and 35;

(c) a light chain CDR3 comprising the amino acid sequence of any one of SEQ ID NOs:28, 36, 101, 45, 103, 97 and 105;

(d) a heavy chain CDR1 comprising the amino acid sequence of any one of SEQ ID NOs:30, 38, 14, 47, 54, 58 and 62;

(e) a heavy chain CDR2 comprising the amino acid sequence of any one of SEQ ID NOs:31, 39, 42, 48, 51, 55, 59 and 63; and (f) a heavy chain CDR3 comprising the amino acid sequence of any one of SEQ ID NOs:32, 40, 43, 49, 52, 56, 60 and 64.

In some embodiments, an anti-BACE-1 antibody, or fragment thereof, comprises two, three, four, five or six CDRs as described above (e.g., each CDR is selected from one of (a)-(f)).

In certain embodiments, an isolated anti-BACE-1 antibody or fragment thereof, comprises one or more CDRs selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of RASQSVGTYLN (SEQ ID NO:26) and RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of ATSNLRS (SEQ ID NO:27) and SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQSYSIPRFT (SEQ ID NO:28), QQASASPYALIT (SEQ ID NO:36) and QQYGYYLIT (SEQ ID NO:45);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNIPYSSMH (SEQ ID NO:30), GFNISYSSIH (SEQ ID NO:38), GFNIYYSYMH (SEQ ID NO:14), GFNISSYYMH (SEQ ID NO:47), GFNISYSSMH (SEQ ID NO:54), GFNIYSSSMH (SEQ ID NO:58) and GFNISYYSMH (SEQ ID NO:62);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SISSYSSSTSYADSVK (SEQ ID NO:31), YISPSSSYTSYADSVK (SEQ ID NO:39), SIYPYYGSTYYADSVK (SEQ ID NO:42), SIYSSYGYTYYADSVK (SEQ ID NO:48), YISSYSSSTYYADSVK (SEQ ID NO:51), SIYPSYSYTSYADSVK (SEQ ID NO:55), YIYSSYGYTYYADSVK (SEQ ID NO:59) and SISPYYGSTYYADSVK (SEQ ID NO:63); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of YICGHRWRDFDMWRARTGVNYAMDY (SEQ ID NO:32), HYYVSVGSGIDY (SEQ ID NO:40), WHGYPPGYSYYSSFSSSGFDY (SEQ ID NO:43) YWGYYAWFGSHPWAYGAFDY (SEQ ID NO:49), SASGIDY (SEQ ID NO:52), SSSSYYYGMDY (SEQ ID NO:56), DNSICVLTQKEVDTKFLVGQHSYVMDY (SEQ ID NO:60) and ERSSCPVGWRDSRFGADGYGLEY (SEQ ID NO:64).

In some embodiments, an anti-BACE-1 antibody, or fragment thereof, comprises two, three, four, five or six CDRs as described above (e.g., each CDR is selected from one of (a)-(f)).

In certain embodiments, the anti-BACE-1 antibody, or fragment thereof, as described herein comprises one or more CDRs selected from the group consisting of:

(a) a light chain CDR1 comprising the amino acid sequence of any one of SEQ ID NOs:26 and 34;

(b) a light chain CDR2 comprising the amino acid sequence of any one of SEQ ID NOs:27 and 35;

(c) a light chain CDR3 comprising the amino acid sequence of any one of SEQ ID NOs:28, 36 and 45;

(d) a heavy chain CDR1 comprising the amino acid sequence of any one of SEQ ID NOs:30, 38, 14, 47, 54, 58 and 62;

(e) a heavy chain CDR2 comprising the amino acid sequence of any one of SEQ ID NOs:31, 39, 42, 48, 51, 55, 59 and 63; and (f) a heavy chain CDR3 comprising the amino acid sequence of any one of SEQ ID NOs:32, 40, 43, 49, 52, 56, 60 and 64.

In some embodiments, an anti-BACE-1 antibody, or fragment thereof, comprises two, three, four, five or six CDRs as described above (e.g., each CDR is selected from one of (a)-(f)).

In some embodiments, an anti-BACE-1 antibody, or a fragment thereof, comprises a light chain sequence, or a fragment thereof, and/or a heavy chain sequence, or a fragment thereof, derived from any of the following antibodies described herein: B3B12, B1A4, B2B5, B2B2, B2B3, B2B9, B2B6 and B1B3. The amino acid sequences of the light chain variable region (VL) and heavy chain variable region (VH) of these anti-BACE-1 antibody clones are set forth in Table 8 below.

In certain embodiments, an anti-BACE-1 antibody, or a fragment thereof, comprises a VL as in any of the embodiments provided herein, and/or a VH as in any of the embodiments provided herein.

In certain embodiments, an anti-BACE-1 antibody described herein, or fragment thereof, comprises a light chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

```
                                       (SEQ ID NO: 25)
(a) DIQMTQSPSSLSASVGDRVTITCRASQSVGTYLNWYQQKPGKAPKL

LIYATSNLRSGVPSRFSGSGSGTDFTLTISSLQPEDFATYYCQQSYSIPR

FTFGPGTKLEIKR;

(SEQ ID NO: 33)
(b) DIQMTQSPSSLSASVGDRVTITCRASQSVSSAVAWYQQKPGKAPKL

LIYSASSLYSGVPSRFSGSRSGTDFTPTISSLQPEDFATYYCQQASASPY

ALITFGQGTKVEIKR;

(SEQ ID NO: 100)
(c) DIQMTQSPSSLSASVGDRVTITCRASQSVSSAVAWYQQKPGKAPKL

LIYSASSLYSGVPSRFSGSRSGTDFTPTISSLQPEDFATYYCQQSYFSYP

ITFGQGTKVEIKR;

(SEQ ID NO: 44)
(d) DIQMTQSPSSLSASVGDRVTITCRASQSVSSAVAWYQQKPGKAPKL

LIYSASSLYSGVPSRFSGSRSGTDFTLTISSLQPEDFATYYCQQYGYYLI

TFGQGTKVEIKR;

(SEQ ID NO: 102)
(e) DIQMTQSPSSLSASVGDRVTITCRASQSVSSAVAWYQQKPGKAPKL

LIYSASSLYSGVPSRFSGSRSGTDFTLTISSLQPEDFATYYCQQSGYAPF

TFGQGTKVEIKR;

(SEQ ID NO: 96)
(f) DIQMTQSPSSLSASVGDRVTITCRASQSVSSAVAWYQQKPGKAPKL

LIYSASSLYSGVPSRFSGSRSGTDFTLTISSLQPEDFATYYCQQSSYSLI

TFGQGTKVEIKR;
and
                                       (SEQ ID NO: 104)
(g) DIQMTQSPSSLSASVGDRVTITCRASQSVSSAVAWYQQKPGKAPKL

LIYSASSLYSGVPSRFSGSRSGTDFTLTISSLQPEDFATYYCQQSGHYHS

LITFGQGTKVEIKR.
```

In some embodiments, an anti-BACE-1 antibody, or fragment thereof, comprises a light chain variable region comprising the amino acid sequence of any one of SEQ ID NOs:25, 33, 100, 44, 102, 96, and 104. In some embodiments, an anti-BACE-1 antibody, or fragment thereof, comprises a light chain variable region consisting of the amino acid sequence of any one of SEQ ID NOs:25, 33, 100, 44, 102, 96, and 104. In some embodiments, an anti-BACE-1 antibody, or fragment thereof, comprises a light chain variable region comprising the amino acid sequence of any one of SEQ ID NOs:25, 33, and 44. In some embodiments, an anti-BACE-1 antibody, or fragment thereof, comprises a light chain variable region consisting of the amino acid sequence of any one of SEQ ID NOs:25, 33, and 44.

In certain embodiments, an isolated anti-BACE-1 antibody described herein, or fragment thereof, comprises a heavy chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

```
                                       (SEQ ID NO: 29)
(a) EVQLVESGGGLVQPGGSLRLSCAASGFNIPYSSMEIWVRQAPGKGL

EWVASISSYSSSTSYADSVKGRFTISADTSKNTAYLQMNSLRAEDTAVYY

CARYICGHRWRDFDMWRARTGVNYAMDYWGQGTLVTVSSAS;

(SEQ ID NO: 37)
(b) EVQLVESGGGLVQPGGSLRLSCAASGFNISYSSIHWVRQAPGKGLE

WVAYISPSSSYTSYADSVKGRFTISADTSKNTAYLQMNSLRAEDTAVYYC

ARHYYVSVGSGIDYWGQGTLVTVSSAS;

(SEQ ID NO: 41)
(c) EVQLVESGGGLVQPGGSLRLSCAASGFNIYYSYMHWVRQAPGKGLE

WVASIYPYYGSTYYADSVKGRFTISADTSKNTAYLQMNSLRAEDTAVYYC

ARWHGYPPGYSYYSSFSSSGFDYWGQGTLVTVSSAS;
```

-continued (d) (SEQ ID NO: 46)
EVQLVESGGGLVQPGGSLRLSCAASGFNISSYYMHWVRQAPGKGLE

WVASIYSSYGYTYYADSVKGRFTISADTSKNTAYLQMNSLRAEDTAVYYC

ARYWGYYAWFGSHPWAYGAFDYWGQGTLVTVSSAS;

(e) (SEQ ID NO: 50)
EVQLVESGGGLVQPGGSLRLSCAASGFNISYSSIHWVRQAPGKGLE

WVAYISSYSSSTYYADSVKGRFTISADTSKNTAYLQMNSLRAEDTAVYYC

ARSASGIDYWGQGTLVTVSSAS;

(f) (SEQ ID NO: 53)
EVQLVESGGGLVQPGGSLRLSCAASGFNISYSSMHWVRQAPGKGLE

WVASIYPSYSYTSYADSVKGRFTISADTSKNTAYLQMNSLRAEDTAVYYC

ARSSSSYYYGMDYWGQGTLVTVSSAS;

(g) (SEQ ID NO: 57)
EVQLVESGGGLVQPGGSLRLSCAASGFNIYSSSMHWVRQAPGKGLE

WVAYIYSSYGYTYYADSVKGRFTISADTSKNTAYLQMNSLRAEDTAVYYC

ARDNSICVLTQKEVDTKFLVGQHSYVMDYWGQGTLVTVSSAS;
and (h) (SEQ ID NO: 61)
EVQLVESGGGLVQPGGSLRLSCAASGFNISYYSMHWVRQAPGKGLE

WVASISPYYGSTYYADSVKGRFTISADTSKNTAYLQMNSLRAEDTAVYYC

ARERSSCPVGWRDSRFGADGYGLEYWGQGTLVTVSSAS.

In some embodiments, an anti-BACE-1 antibody, or fragment thereof, comprises a heavy chain variable region comprising the amino acid sequence of any one of SEQ ID NOs:29, 37, 41, 46, 50, 53, 57 and 61. In some embodiments, an anti-BACE-1 antibody, or fragment thereof, comprises a heavy chain variable region consisting of the amino acid sequence of any one of SEQ ID NOs:29, 37, 41, 46, 50, 53, 57 and 61.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:25, 33, 100, 44, 102, 96, and 104 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:29, 37, 41, 46, 50, 53, 57 and 61.

In some embodiments, an anti-BACE-1 antibody, or fragment thereof, comprises a light chain variable region consisting of an amino acid sequence of SEQ ID NOs:25, 33, 100, 44, 102, 96, and 104 and further comprises a heavy chain variable region consisting of an amino acid sequence of SEQ ID NOs:29, 37, 41, 46, 50, 53, 57 and 61.

Clone B3B12

In some embodiments, an anti-BACE-1 antibody, or fragment thereof, comprises a light chain CDR1 comprising the amino acid sequence of SEQ ID NO:26, a light chain CDR2 comprising the amino acid sequence of SEQ ID NO:27, and a light chain CDR3 comprising the amino acid sequence of SEQ ID NO:28. In some embodiments, an anti-BACE-1 antibody, or fragment thereof, comprises a heavy chain CDR1 comprising the amino acid sequence of SEQ ID NO:30, a heavy chain CDR2 comprising the amino acid sequence of SEQ ID NO:31, and a heavy chain CDR3 comprising the amino acid sequence of SEQ ID NO:32. In some embodiments, an anti-BACE-1 antibody, or fragment thereof, comprises a light chain CDR1-3 and a heavy chain CDR1-3 comprising the amino acid sequences of SEQ ID NOs:26, 27, 28, 30, 31 and 32, respectively. In some embodiments, an anti-BACE-1 antibody, or fragment thereof, comprises a light chain CDR1-3 and a heavy chain CDR1-3 consisting of the amino acid sequences of SEQ ID NOs:26, 27, 28, 30, 31 and 32, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:25. In some embodiments, an anti-BACE-1 antibody, or fragment thereof, comprises a light chain variable region comprising the amino acid sequence of SEQ ID NO:25. In some embodiments, an anti-BACE-1 antibody, or fragment thereof, comprises a light chain variable region consisting of the amino acid sequence of SEQ ID NO:25.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:29. In some embodiments, an anti-BACE-1 antibody, or fragment thereof, comprises a heavy chain variable region comprising the amino acid sequence of SEQ ID NO:29. In some embodiments, an anti-BACE-1 antibody, or fragment thereof, comprises a heavy chain variable region consisting of the amino acid sequence of SEQ ID NO:29.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:25 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:29. In some embodiments, an anti-BACE-1 antibody, or fragment thereof, comprises a light chain variable region comprising the amino acid sequence of SEQ ID NO:25 and further comprises a heavy chain variable region comprising the amino acid sequence of SEQ ID NO:29. In some embodiments, an anti-BACE-1 antibody, or fragment thereof, comprises a light chain variable region consisting of the amino acid sequence of SEQ ID NO:25 and further comprises a heavy chain variable region consisting of the amino acid sequence of SEQ ID NO:29.

Clone B1A4

In some embodiments, an anti-BACE-1 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:36. In some embodiments, an anti-BACE-1 antibody, or fragment thereof, comprises a heavy chain CDR1 comprising the amino acid sequence of SEQ ID NO:38, a heavy chain CDR2 comprising the amino acid sequence of SEQ ID NO:39, and a heavy chain CDR3 comprising the amino acid sequence of SEQ ID NO:40. In some embodiments, an anti-BACE-1 antibody, or fragment thereof, comprises a light chain CDR1-3 and a heavy chain CDR1-3 comprising the amino acid sequences of SEQ ID NOs:34, 35, 36, 38, 39 and 40, respectively. In some embodiments, an anti-BACE-1 antibody, or fragment thereof, comprises a light chain CDR1-3 and a heavy chain CDR1-3 consisting of the amino acid sequences of SEQ ID NOs:34, 35, 36, 38, 39 and 40, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:33. In some embodiments, an anti-BACE-1 antibody, or fragment thereof, comprises a light chain variable region comprising the amino acid sequence of SEQ ID NO:33. In some embodiments, an anti-BACE-1 antibody, or fragment thereof, comprises a light chain variable region consisting of the amino acid sequence of SEQ ID NO:33.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:37. In some embodiments, an anti-BACE-1 antibody, or fragment thereof, comprises a heavy chain variable region comprising the amino acid sequence of SEQ ID NO:37. In some embodiments, an anti-BACE-1 antibody, or fragment thereof, comprises a heavy chain variable region consisting of the amino acid sequence of SEQ ID NO:37.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:33 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:37. In some embodiments, an anti-BACE-1 antibody, or fragment thereof, comprises a light chain variable region comprising the amino acid sequence of SEQ ID NO:33 and further comprises a heavy chain variable region comprising the amino acid sequence of SEQ ID NO:37. In some embodiments, an anti-BACE-1 antibody, or fragment thereof, comprises a light chain variable region consisting of the amino acid sequence of SEQ ID NO:33 and further comprises a heavy chain variable region consisting of the amino acid sequence of SEQ ID NO:37.

Clone B2B5

In some embodiments, an anti-BACE-1 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:101. In some embodiments, an anti-BACE-1 antibody, or fragment thereof, comprises a heavy chain CDR1 comprising the amino acid sequence of SEQ ID NO:14, a heavy chain CDR2 comprising the amino acid sequence of SEQ ID NO:42, and a heavy chain CDR3 comprising the amino acid sequence of SEQ ID NO:43. In some embodiments, an anti-BACE-1 antibody, or fragment thereof, comprises a light chain CDR1-3 and a heavy chain CDR1-3 comprising the amino acid sequences of SEQ ID NOs:34, 35, 101, 14, 42, and 43, respectively. In some embodiments, an anti-BACE-1 antibody, or fragment thereof, comprises a light chain CDR1-3 and a heavy chain CDR1-3 consisting of the amino acid sequences of SEQ ID NOs:34, 35, 101, 14, 42, and 43, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:100. In some embodiments, an anti-BACE-1 antibody, or fragment thereof, comprises a light chain variable region comprising the amino acid sequence of SEQ ID NO:100. In some embodiments, an anti-BACE-1 antibody, or fragment thereof, comprises a light chain variable region consisting of the amino acid sequence of SEQ ID NO:100.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:41. In some embodiments, an anti-BACE-1 antibody, or fragment thereof, comprises a heavy chain variable region comprising the amino acid sequence of SEQ ID NO:41. In some embodiments, an anti-BACE-1 antibody, or fragment thereof, comprises a heavy chain variable region consisting of the amino acid sequence of SEQ ID NO:41.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:100 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:41. In some embodiments, an anti-BACE-1 antibody, or fragment thereof, comprises a light chain variable region comprising the amino acid sequence of SEQ ID NO:100 and further comprises a heavy chain variable region comprising the amino acid sequence of SEQ ID NO:41. In some embodiments, an anti-BACE-1 antibody, or fragment thereof, comprises a light chain variable region consisting of the amino acid sequence of SEQ ID NO:100 and further comprises a heavy chain variable region consisting of the amino acid sequence of SEQ ID NO:41.

Clone B2B2

In some embodiments, an anti-BACE-1 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:45. In some embodiments, an anti-BACE-1 antibody, or fragment thereof, comprises a heavy chain CDR1 comprising the amino acid sequence of SEQ ID NO:47, a heavy chain CDR2 comprising the amino acid sequence of SEQ ID NO:48, and a heavy chain CDR3 comprising the amino acid sequence of SEQ ID NO:49. In some embodiments, an anti-BACE-1 antibody, or fragment thereof, comprises a light chain CDR1-3 and a heavy chain CDR1-3 comprising the amino acid sequences of SEQ ID NOs:34, 35, 45, 47, 48 and 49, respectively. In some embodiments, an anti-BACE-1 antibody, or fragment thereof, comprises a light chain CDR1-3 and a heavy chain CDR1-3 consisting of the amino acid sequences of SEQ ID NOs:34, 35, 45, 47, 48 and 49, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:44. In some embodiments, an anti-BACE-1 antibody, or fragment thereof, comprises a light chain variable region comprising the amino acid sequence of SEQ ID NO:44. In some embodiments, an anti-BACE-1 antibody, or fragment thereof, comprises a light chain variable region consisting of the amino acid sequence of SEQ ID NO:44.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:46. In some embodiments, an anti-BACE-1 antibody, or fragment thereof, comprises a heavy chain variable region comprising the amino acid sequence of SEQ ID NO:46. In some embodiments, an anti-BACE-1 antibody, or fragment thereof, comprises a heavy chain variable region consisting of the amino acid sequence of SEQ ID NO:46.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:44 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:46. In some embodiments, an anti-BACE-1 antibody, or fragment thereof, comprises a light chain variable region comprising the amino acid sequence of SEQ ID NO:44 and further comprises a heavy chain variable region comprising the amino acid sequence of SEQ ID NO:46. In some embodiments, an anti-BACE-1 antibody, or fragment thereof, comprises a light chain variable region consisting of the amino acid sequence of SEQ ID NO:44 and further comprises a heavy chain variable region consisting of the amino acid sequence of SEQ ID NO:46.

Clone B2B3

In some embodiments, an anti-BACE-1 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:103. In some embodiments, an anti-BACE-1 antibody, or fragment thereof, comprises a heavy chain CDR1 comprising the amino acid sequence of SEQ ID NO:38, a heavy chain CDR2 comprising the amino acid sequence of SEQ ID NO:51, and a heavy chain CDR3 comprising the amino acid sequence of SEQ ID NO:52. In some embodiments, an anti-BACE-1 antibody, or fragment thereof, comprises a light chain CDR1-3 and a heavy chain CDR1-3 comprising the amino acid sequences of SEQ ID NOs:34, 35, 103, 38, 51, and 52, respectively. In some embodiments, an anti-BACE-1 antibody, or fragment thereof, comprises a light chain CDR1-3 and a heavy chain CDR1-3 consisting of the amino acid sequences of SEQ ID NOs:34, 35, 103, 38, 51, and 52, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:102. In some embodiments, an anti-BACE-1 antibody, or fragment thereof, comprises a light chain variable region comprising the amino acid sequence of SEQ ID NO:102. In some embodiments, an anti-BACE-1 antibody, or fragment thereof, comprises a light chain variable region consisting of the amino acid sequence of SEQ ID NO:102.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:50. In some embodiments, an anti-BACE-1 antibody, or fragment thereof, comprises a heavy chain variable region comprising the amino acid sequence of SEQ ID NO:50. In some embodiments, an anti-BACE-1 antibody, or fragment thereof, comprises a heavy chain variable region consisting of the amino acid sequence of SEQ ID NO:50.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:102 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:50. In some embodiments, an anti-BACE-1 antibody, or fragment thereof, comprises a light chain variable region comprising the amino acid sequence of SEQ ID NO:102 and further comprises a heavy chain variable region comprising the amino acid sequence of SEQ ID NO:50. In some embodiments, an anti-BACE-1 antibody, or fragment thereof, comprises a light chain variable region consisting of the amino acid sequence of SEQ ID NO:102 and further comprises a heavy chain variable region consisting of the amino acid sequence of SEQ ID NO:50.

Clone B2B9

In some embodiments, an anti-BACE-1 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:97. In some embodiments, an anti-BACE-1 antibody, or fragment thereof, comprises a heavy chain CDR1 comprising the amino acid sequence of SEQ ID NO:54, a heavy chain CDR2 comprising the amino acid sequence of SEQ ID NO:55, and a heavy chain CDR3 comprising the amino acid sequence of SEQ ID NO:56. In some embodiments, an anti-BACE-1 antibody, or fragment thereof, comprises a light chain CDR1-3 and a heavy chain CDR1-3 comprising the amino acid sequences of SEQ ID NOs:34, 35, 97, 54, 55, and 56, respectively. In some embodiments, an anti-BACE-1 antibody, or fragment thereof, comprises a light chain CDR1-3 and a heavy chain CDR1-3 consisting of the amino acid sequences of SEQ ID NOs:34, 35, 97, 54, 55, and 56, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:96. In some embodiments, an anti-BACE-1 antibody, or fragment thereof, comprises a light chain variable region comprising the amino acid sequence of SEQ ID NO:96. In some embodiments, an anti-BACE-1 antibody, or fragment thereof, comprises a light chain variable region consisting of the amino acid sequence of SEQ ID NO:96.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:53. In some embodiments, an anti-BACE-1 antibody, or fragment thereof, comprises a heavy chain variable region comprising the amino acid sequence of SEQ ID NO:53. In some embodiments, an anti-BACE-1 antibody, or fragment thereof, comprises a heavy chain variable region consisting of the amino acid sequence of SEQ ID NO:53.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:96 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:53. In some embodiments, an anti-BACE-1 antibody, or fragment thereof, comprises a light chain variable region comprising the amino acid sequence of SEQ ID NO:96 and further comprises a heavy chain variable region comprising the amino acid sequence of SEQ ID NO:53. In some embodiments, an anti-BACE-1 antibody, or fragment thereof, comprises a light chain variable region consisting of the amino acid sequence of SEQ ID NO:96 and further comprises a heavy chain variable region consisting of the amino acid sequence of SEQ ID NO:53.

Clone B2B6

In some embodiments, an anti-BACE-1 antibody, or fragment thereof, comprises a heavy chain CDR1 comprising the amino acid sequence of SEQ ID NO:58, a heavy chain CDR2 comprising the amino acid sequence of SEQ ID NO:59, and a heavy chain CDR3 comprising the amino acid sequence of SEQ ID NO:60. In some embodiments, an anti-BACE-1 antibody, or fragment thereof, comprises a heavy chain CDR1-3 consisting of the amino acid sequences of SEQ ID NOs:58, 59 and 60, respectively.

In certain embodiments, anti-BACE-1 antibody, or fragment thereof, comprises a light chain variable region, or a portion thereof.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:57. In some embodiments, an anti-BACE-1 antibody, or fragment thereof, comprises a heavy chain variable region comprising the amino acid sequence of SEQ ID NO:57. In some embodiments, an anti-BACE-1 antibody, or fragment thereof, comprises a heavy chain variable region consisting of the amino acid sequence of SEQ ID NO:57.

Clone B1B3

In some embodiments, an anti-BACE-1 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:105. In some embodiments, an anti-BACE-1 antibody, or fragment thereof, comprises a heavy chain CDR1 comprising the amino acid sequence of SEQ ID NO:62, a heavy chain CDR2 comprising the amino acid sequence of SEQ ID NO:63, and a heavy chain CDR3 comprising the amino acid sequence of SEQ ID NO:64. In some embodiments, an anti-BACE-1 antibody, or fragment thereof, comprises a light chain CDR1-3 and a heavy chain CDR1-3 comprising the amino acid sequences of SEQ ID NOs:34, 35, 105, 62, 63, and 64, respectively. In some embodiments, an anti-BACE-1 antibody, or fragment thereof, comprises a light chain CDR1-3 and a heavy chain CDR1-3 consisting of the amino acid sequences of SEQ ID NOs:34, 35, 105, 62, 63, and 64, respectively.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:104. In some embodiments, an anti-BACE-1 antibody, or fragment thereof, comprises a light chain variable region comprising the amino acid sequence of SEQ ID NO:104. In some embodiments, an anti-BACE-1 antibody, or fragment thereof, comprises a light chain variable region consisting of the amino acid sequence of SEQ ID NO:105.

In some embodiments, an anti-BACE-1 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:61. In some embodiments, an anti-BACE-1 antibody, or fragment thereof, comprises a heavy chain variable region comprising the amino acid sequence of SEQ ID NO:61. In some embodiments, an anti-BACE-1 antibody, or fragment thereof, comprises a heavy chain variable region consisting of the amino acid sequence of SEQ ID NO:61.

In some embodiments, an anti-BACE-1 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:104 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:61. In some embodiments, an anti-BACE-1 antibody, or fragment thereof, comprises a light chain variable region comprising the amino acid sequence of SEQ ID NO:104 and further comprises a heavy chain variable region comprising the amino acid sequence of SEQ ID NO:61. In some embodiments, an anti-BACE-1 antibody, or fragment thereof, comprises a light chain variable region consisting of the amino acid sequence of SEQ ID NO:104 and further comprises a heavy chain variable region consisting of the amino acid sequence of SEQ ID NO:61.

Anti-Alp2 Antibodies or Fragments Thereof

Certain embodiments provide antibodies and antigen-binding portions of antibodies that specifically bind to Alp2 (i.e., an anti-Alp2 antibody, or fragment thereof). Autophagic serine protease Alp2 (Gene ID=3510885) is a highly expressed conserved cell wall protein of Aspergillusfumigatus, a pathogenic fungal specie that causes Aspergillosis in individuals with an immunodeficiency.

In some embodiments, an anti-Alp2 antibody, or fragment thereof, comprises: (1) one or more complementarity determining region (CDR) sequences; (2) a heavy chain variable region sequence; and/or (3) a light chain variable region sequence, as described herein (e.g., as described in Table 8 below).

In certain embodiments, an isolated anti-Alp2 antibody or fragment thereof, comprises one or more CDRs selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of QQASHLIT (SEQ ID NO:107);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNISSYYIH (SEQ ID NO:66), GFNLSSSSMH (SEQ ID NO:70) and GFNIYYSYIH (SEQ ID NO:74);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SIYSYSSYTYYADSVK (SEQ ID NO:67), SIYPSYSYTYYADSVK (SEQ ID NO:71) and SIYSYYGYTYYADSVK (SEQ ID NO:75);

(f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of FGSWSYAIDY (SEQ ID NO:68), KTSDQYLLVGGSFFKLRDCCYVMDY (SEQ ID NO:72) and GRSPGPYAVCGNLFRSVSYGMDY (SEQ ID NO:76).

In some embodiments, an anti-Alp2 antibody, or fragment thereof, comprises two, three, four, five or six CDRs as described above (e.g., each CDR is selected from one of (a)-(f); or from one of (d)-(f)).

In certain embodiments, the anti-Alp2 antibody, or fragment thereof, as described herein comprises one or more CDRs selected from the group consisting of:

(a) a light chain CDR1 comprising the amino acid sequence of SEQ ID NO:34;

(b) a light chain CDR2 comprising the amino acid sequence of SEQ ID NO:35; and (c) a heavy chain CDR3 comprising the amino acid sequence of SEQ ID NO:107;

(d) a heavy chain CDR1 comprising the amino acid sequence of any one of SEQ ID NOs:66, 70 and 74;

(e) a heavy chain CDR2 comprising the amino acid sequence of any one of SEQ ID NOs:67, 71 and 75; and (f) a heavy chain CDR3 comprising the amino acid sequence of any one of SEQ ID NOs:68, 72 and 76.

In some embodiments, an anti-Alp2 antibody, or fragment thereof, comprises two, three, four, five or six CDRs as described above (e.g., each CDR is selected from one of (a)-(f); or from one of (d)-(f)).

In some embodiments, an anti-Alp2 antibody, or a fragment thereof, comprises a light chain sequence, or a fragment thereof, and/or a heavy chain sequence, or a fragment thereof, derived from any of the following antibodies described herein: A4A1, A4A2 and A4A7. The amino acid sequences of the light chain variable region (VL) and heavy chain variable region (VH) of these anti-Alp2 antibody clones are set forth in Table 8 below.

In certain embodiments, an anti-Alp2 antibody, or a fragment thereof, comprises a VL as described in any of the embodiments provided herein, and/or a VH as described in any of the embodiments provided herein.

In certain embodiments, an isolated anti-Alp2 antibody described herein, or fragment thereof, comprises a light chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to:

```
                                      (SEQ ID NO: 106)
DIQMTQSPSSLSASVGDRVTITCRASQSVSSAVAWYQQKPGKAPKLLIYS

ASSLYSGVPSRFSGSRSGTDFTLTISSLQPEDFATYYCQQASHLITFGQG

TKVEIKR.
```

In some embodiments, an anti-Alp2 antibody, or fragment thereof, comprises a light chain variable region comprising the amino acid sequence of SEQ ID NO:106. In some embodiments, an anti-Alp2 antibody, or fragment thereof, comprises a light chain variable region consisting of the amino acid sequence of SEQ ID NO:106.

In certain embodiments, an isolated anti-Alp2 antibody described herein, or fragment thereof, comprises a heavy chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

```
                                       (SEQ ID NO: 65)
(a) EVQLVESGGGLVQPGGSLRLSCAASGFNISSYYIEWVRQAPGKGLE

WVASIYSYSSYTYYADSVKGRFTISADTSKNTAYLQMNSLRAGDTAVYYC

ARFGSWSYAIDYWGQGTLVTVSSAS;

(SEQ ID NO: 69)
(b) EVQLVESGGGLVQPGGSLRLSCAASGFNLSSSSMEIWVRQAPGKGL

EWVASIYPSYSYTYYADSVKGRFTISADTSKNTAYLQMNSLRAEDTAVYY

CARKTSDQYLLVGGSFFKLRDCCYVMDYWGQGTLVTVSSAS;
and (SEQ ID NO: 73)
(c) EVQLVESGGGLVQPGGSLRLSCAASGFNIYYSYIEWVRQAPGKGLE

WVASIYSYYGYTYYADSVKGRFTISADTSKNTAYLQMNSLRAEDTAVYYC

ARGRSPGPYAVCGNLFRSVSYGMDYWGQGTLVTVSSAS.
```

In some embodiments, an anti-Alp2 antibody, or fragment thereof, comprises a heavy chain variable region comprising the amino acid sequence of any one of SEQ ID NOs:65, 69 and 73. In some embodiments, an anti-Alp2 antibody, or fragment thereof, comprises a heavy chain variable region consisting of the amino acid sequence of any one of SEQ ID NOs:65, 69 and 73.

In some embodiments, an anti-Alp2 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:106 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:65, 69 and 73.

In some embodiments, an anti-Alp2 antibody, or fragment thereof, comprises a light chain variable region consisting of an amino acid sequence of SEQ ID NO:106 and further comprises a heavy chain variable region consisting of an amino acid sequence of SEQ ID NOs:65, 69 and 73.

Clone A4A1

In some embodiments, an anti-Alp2 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:107. In some embodiments, an anti-Alp2 antibody, or fragment thereof, comprises a heavy chain CDR1 comprising the amino acid sequence of SEQ ID NO:66, a heavy chain CDR2 comprising the amino acid sequence of SEQ ID NO:67, and a heavy chain CDR3 comprising the amino acid sequence of SEQ ID NO:68. In some embodiments, an anti-Alp2 antibody, or fragment thereof, comprises a light chain CDR1-3 and a heavy chain CDR1-3 comprising the amino acid sequences of SEQ ID NOs:34, 35, 107, 66, 67, and 68, respectively. In some embodiments, an anti-Alp2 antibody, or fragment thereof, comprises a light chain CDR1-3 and a heavy chain CDR1-3 consisting of the amino acid sequences of SEQ ID NOs:34, 35, 107, 66, 67, and 68, respectively.

In some embodiments, an anti-Alp2 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:106. In some embodiments, an anti-Alp2 antibody, or fragment thereof, comprises a light chain variable region comprising the amino acid sequence of SEQ ID NO:106. In some embodiments, an anti-Alp2 antibody, or fragment thereof, comprises a light chain variable region consisting of the amino acid sequence of SEQ ID NO:106.

In some embodiments, an anti-Alp2 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:65. In some embodiments, an anti-Alp2 antibody, or fragment thereof, comprises a heavy chain variable region comprising the amino acid sequence of SEQ ID NO:65. In some embodiments, an anti-Alp2 antibody, or fragment thereof, comprises a heavy chain variable region consisting of the amino acid sequence of SEQ ID NO:65.

In some embodiments, an anti-Alp2 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:106 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:65. In some embodiments, an anti-Alp2 antibody, or fragment thereof, comprises a light chain variable region comprising the amino acid sequence of SEQ ID NO:106 and further comprises a heavy chain variable region comprising the amino acid sequence of SEQ ID NO:65. In some embodiments, an anti-Alp2 antibody, or fragment thereof, comprises a light chain variable region consisting of the amino acid sequence of SEQ ID NO:106 and further comprises a heavy chain variable region consisting of the amino acid sequence of SEQ ID NO:65.

Clone A4A2

In some embodiments, an anti-Alp2 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:107. In some embodiments, an anti-Alp2 antibody, or fragment thereof, comprises a heavy chain CDR1 comprising the amino acid sequence of SEQ ID NO:70, a heavy chain CDR2 comprising the amino acid sequence of SEQ ID NO:71, and a heavy chain CDR3 comprising the amino acid sequence of SEQ ID NO:72. In some embodiments, an anti-Alp2 antibody, or fragment thereof, comprises a light chain CDR1-3 and a heavy chain CDR1-3 comprising the amino acid sequences of SEQ ID NOs:34, 35, 107, 70, 71, and 72, respectively. In some embodiments, an anti-Alp2 antibody, or fragment thereof, comprises a light chain CDR1-3 and a heavy chain CDR1-3 consisting of the amino acid sequences of SEQ ID NOs:34, 35, 107, 70, 71, and 72, respectively.

In some embodiments, an anti-Alp2 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:106. In some embodiments, an anti-Alp2 antibody, or fragment thereof, comprises a light chain variable region comprising the amino acid sequence of SEQ ID NO:106. In some embodiments, an anti-Alp2 antibody, or fragment thereof, comprises a light chain variable region consisting of the amino acid sequence of SEQ ID NO:106.

In some embodiments, an anti-Alp2 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:69. In some embodiments, an anti-Alp2 antibody, or fragment thereof, comprises a heavy chain variable region comprising the amino acid sequence of SEQ ID NO:69. In some embodiments, an anti-Alp2 antibody, or fragment thereof, comprises a heavy chain variable region consisting of the amino acid sequence of SEQ ID NO:69.

In some embodiments, an anti-Alp2 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:106 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:69. In some embodiments, an anti-Alp2 antibody, or fragment thereof, comprises a light chain variable region comprising the amino acid sequence of SEQ ID NO:106 and further comprises a heavy chain variable region comprising the amino acid sequence of SEQ ID NO:69. In some embodiments, an anti-Alp2 antibody, or fragment thereof, comprises a light chain variable region consisting of the amino acid sequence of SEQ ID NO:106 and further comprises a heavy chain variable region consisting of the amino acid sequence of SEQ ID NO:69.

Clone A4A7

In some embodiments, an anti-Alp2 antibody, or fragment thereof, comprises a heavy chain CDR1 comprising the amino acid sequence of SEQ ID NO:74, a heavy chain CDR2 comprising the amino acid sequence of SEQ ID NO:75, and a heavy chain CDR3 comprising the amino acid sequence of SEQ ID NO:76. In some embodiments, an anti-Alp2 antibody, or fragment thereof, comprises a heavy chain CDR1-3 consisting of the amino acid sequences of SEQ ID NOs:74, 75 and 76, respectively.

In certain embodiments, anti-Alp2 antibody, or fragment thereof, comprises a light chain variable region, or a portion thereof.

In some embodiments, an anti-Alp2 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:73. In some embodiments, an anti-Alp2 antibody, or fragment thereof, comprises a heavy chain variable region comprising the amino acid sequence of SEQ ID NO:73. In some embodiments, an anti-Alp2 antibody, or fragment thereof, comprises a heavy chain variable region consisting of the amino acid sequence of SEQ ID NO:73.

Anti-Cathepsin B Antibodies or Fragments Thereof

Certain embodiments provide antibodies and antigen-binding portions of antibodies that specifically bind to cathepsin B (i.e., an anti-cathepsin B antibody, or fragment thereof). Cathepsin B (Gene ID=1508) is a lysosomal cysteine protease, overexpression of which is associated with esophageal adenocarcinoma and other tumors.

In some embodiments, an anti-cathepsin B antibody, or fragment thereof, comprises: (1) one or more complementarity determining region (CDR) sequences; (2) a heavy chain variable region sequence; and/or (3) a light chain variable region sequence, as described herein (e.g., as described in Table 8 below).

In certain embodiments, an isolated anti-cathepsin B antibody or fragment thereof, comprises one or more CDRs selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVS-SAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQWSSSWGYLIT (SEQ ID NO:109); and QQHYSLIT (SEQ ID NO:111);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFNISYYYMH (SEQ ID NO:78), GFNIYYYSIH (SEQ ID NO:82) and GFNLYSSYIH (SEQ ID NO:2);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SIYPSSGSTYYADSVK (SEQ ID NO:79), YIYSYYG-STYYADSVK (SEQ ID NO:83) and SIYPYSSSTSY-ADSVK (SEQ ID NO:86); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of GFAWSPGLDY (SEQ ID NO:80), YGYPG-GYHFWGWWSSPYAFDY (SEQ ID NO:84) and GGGSWSAMDY (SEQ ID NO:87).

In some embodiments, an anti-cathepsin B antibody, or fragment thereof, comprises two, three, four, five or six CDRs as described above (e.g., each CDR is selected from one of (a)-(f); or from one of (d)-(f)).

In certain embodiments, the anti-cathepsin B antibody, or fragment thereof, as described herein comprises one or more CDRs selected from the group consisting of:

(a) a light chain CDR1 comprising the amino acid sequence of SEQ ID NO:34;

(b) a light chain CDR2 comprising the amino acid sequence of SEQ ID NO:35;

(c) a light chain CDR3 comprising the amino acid sequence of any one of SEQ ID NOs:109 and 111;

(d) a heavy chain CDR1 comprising the amino acid sequence of any one of SEQ ID NOs:78, 82 and 2;

(e) a heavy chain CDR2 comprising the amino acid sequence of any one of SEQ ID NOs:79, 83 and 86; and (f) a heavy chain CDR3 comprising the amino acid sequence of any one of SEQ ID NOs:80, 84 and 87.

In some embodiments, an anti-cathepsin B antibody, or fragment thereof, comprises two, three, four, five, or six CDRs as described above (e.g., each CDR is selected from one of (a)-(f); or from one of (d)-(f)).

In some embodiments, an anti-cathepsin B antibody, or a fragment thereof, comprises a light chain sequence, or a fragment thereof, and/or a heavy chain sequence, or a fragment thereof, derived from any of the following antibodies described herein: CBA3, CBA2 and CBA1. The amino acid sequences of the light chain variable region (VL) and heavy chain variable region (VH) of these anti-cathepsin B antibody clones are set forth in Table 8 below.

In certain embodiments, an anti-cathepsin B antibody, or a fragment thereof, comprises a VL as in any of the embodiments provided herein, and/or a VH as described in any of the embodiments provided herein.

In certain embodiments, an isolated anti-cathepsin B antibody described herein, or fragment thereof, comprises a light chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

(a) DIQMTQSPSSLSASVGDRVTITCRASQSVSSAVAWYQQKPGKAPKL (SEQ ID NO: 108)

LIYSASSLYSGVPSRFSGSRSGTDFTLTISSLQPEDFATYYCQQWSSSWG

YLITFGQGTKVEIKR;
and (b) DIQMTQSPSSLSASVGDRVTITCRASQSVSSAVAWYQQKPGKAPKL (SEQ ID NO: 110)

LIYSASSLYSGVPSRFSGSRSGTDFTLTISSLQPEDFATYYCQQHYSLIT

FGQGTKVEIKR.

In some embodiments, an anti-cathepsin B antibody, or fragment thereof, comprises a light chain variable region comprising the amino acid sequence of any one of SEQ ID NOs:108, and 110. In some embodiments, an anti-cathepsin B antibody, or fragment thereof, comprises a light chain variable region consisting of the amino acid sequence of any one of SEQ ID NOs: 108 and 110.

In certain embodiments, an isolated anti-cathepsin B antibody described herein, or fragment thereof, comprises a heavy chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

(a) EVQLVESGGGLVQPGGSLRLSCAASGFNISYYYMHWVRQAPGKGLE (SEQ ID NO: 77)

WVASIYPSSGSTYYADSVKGRFTISADTSKNTAYLQMNSLRAEDTAVYYC

ARGFAWSPGLDYWGQGTLVTVSSAS;

(b) EVQLVESGGGLVQPGGSLRLSCAASGFNIYYYSIHWVRQAPGKGLE (SEQ ID NO: 81)

WVAYIYSYYGSTYYADSVKGRFTISADTSKNTAYLQMNSLRAEDTAVYYC

ARYGYPGGYHFWGWWSSPYAFDYWGQGTLVTVSSAS;
and (c) EVQLVESGGGLVQPGGSLRLSCAASGFNLYSSYIHWVRQAPGKGLE (SEQ ID NO: 85)

WVASIYPYSSSTSYADSVKGRFTISADTSKNTAYLQMNSLRAEDTAVYYC

ARGGGSWSAMDYWGQGTLVTVSSAS.

In some embodiments, an anti-cathepsin B antibody, or fragment thereof, comprises a heavy chain variable region comprising the amino acid sequence of any one of SEQ ID NOs:77, 81 and 85. In some embodiments, an anti-cathepsin B antibody, or fragment thereof, comprises a heavy chain variable region consisting of the amino acid sequence of any one of SEQ ID NOs: 77, 81 and 85.

In some embodiments, an anti-cathepsin B antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:108 and 110 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:77, 81, and 85.

In some embodiments, an anti-cathepsin B antibody, or fragment thereof, comprises a light chain variable region consisting of an amino acid sequence of SEQ ID NOs:108 and 110 and further comprises a heavy chain variable region consisting of an amino acid sequence of SEQ ID NOs:77, 81 and 85.

Clone CBA3

In some embodiments, an anti-cathepsin B antibody, or fragment thereof, comprises a heavy chain CDR1 comprising the amino acid sequence of SEQ ID NO:78, a heavy chain CDR2 comprising the amino acid sequence of SEQ ID NO:79, and a heavy chain CDR3 comprising the amino acid sequence of SEQ ID NO:80. In some embodiments, an anti-cathepsin B antibody, or fragment thereof, comprises a heavy chain CDR1-3 consisting of the amino acid sequences of SEQ ID NOs:78, 79 and 80, respectively.

In certain embodiments, anti-cathepsin B antibody, or fragment thereof, comprises a light chain variable region, or a portion thereof.

In some embodiments, an anti-cathepsin B antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:77. In some embodiments, an anti-cathepsin B antibody, or fragment thereof, comprises a heavy chain variable region comprising the amino acid sequence of SEQ ID NO:77. In some embodiments, an anti-cathepsin B antibody, or fragment thereof, comprises a heavy chain variable region consisting of the amino acid sequence of SEQ ID NO:77.

Clone CBA2

In some embodiments, an anti-cathepsin B antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:109. In some embodiments, an anti-cathepsin B antibody, or fragment thereof, comprises a heavy chain CDR1 comprising the amino acid sequence of SEQ ID NO:82, a heavy chain CDR2 comprising the amino acid sequence of SEQ ID NO:83, and a heavy chain CDR3 comprising the amino acid sequence of SEQ ID NO:84. In some embodiments, an anti-cathepsin B antibody, or fragment thereof, comprises a light chain CDR1-3 and a heavy chain CDR1-3 comprising the amino acid sequences of SEQ ID NOs:34, 35, 109, 82, 83, and 84, respectively. In some embodiments, an anti-cathepsin B antibody, or fragment thereof, comprises a light chain CDR1-3 and a heavy chain CDR1-3 consisting of the amino acid sequences of SEQ ID NOs:34, 35, 109, 82, 83, and 84, respectively.

In some embodiments, an anti-cathepsin B antibody, or fragment thereof, comprises a light chain variable region comprising an amino acid sequence that has at least about 80% (e.g., 81%, 82%, 83%, 84%, 85%, 86%, 87%, 88%, 89%, 90%, 910%, 92%, 93%, 94%, 95%, 96%, 97%, 98%, 99% or 100%) sequence identity to SEQ ID NO:108. In some embodiments, an anti-cathepsin B antibody, or fragment thereof, comprises a light chain variable region comprising the amino acid sequence of SEQ ID NO:108. In some embodiments, an anti-cathepsin B antibody, or fragment thereof, comprises a light chain variable region consisting of the amino acid sequence of SEQ ID NO:108.

In some embodiments, an anti-cathepsin B antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:81. In some embodiments, an anti-cathepsin B antibody, or fragment thereof, comprises a heavy chain variable region comprising the amino acid sequence of SEQ ID NO:81. In some embodiments, an anti-cathepsin B antibody, or fragment thereof, comprises a heavy chain variable region consisting of the amino acid sequence of SEQ ID NO:81.

In some embodiments, an anti-cathepsin B antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:108 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:81. In some embodiments, an anti-cathepsin B antibody, or fragment thereof, comprises a light chain variable region comprising the amino acid sequence of SEQ ID NO:108 and further comprises a heavy chain variable region comprising the amino acid sequence of SEQ ID NO:81. In some embodiments, an anti-cathepsin B antibody, or fragment thereof, comprises a light chain variable region consisting of the amino acid sequence of SEQ ID NO:108 and further comprises a heavy chain variable region consisting of the amino acid sequence of SEQ ID NO:81.

Clone CBA1

In some embodiments, an anti-cathepsin B antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:111. In some embodiments, an anti-cathepsin B antibody, or fragment thereof, comprises a heavy chain CDR1 comprising the amino acid sequence of SEQ ID NO:2, a heavy chain CDR2 comprising the amino acid sequence of SEQ ID NO:86, and a heavy chain CDR3 comprising the amino acid sequence of SEQ ID NO:87. In some embodiments, an anti-cathepsin B antibody, or fragment thereof, comprises a light chain CDR1-3 and a heavy chain CDR1-3 comprising the amino acid sequences of SEQ ID NOs:34, 35, 111, 2, 86, and 87, respectively. In some embodiments, an anti-cathepsin B antibody, or fragment thereof, comprises a light chain CDR1-3 and a heavy chain CDR1-3 consisting of the amino acid sequences of SEQ ID NOs:34, 35, 111, 2, 86, and 87, respectively.

In some embodiments, an anti-cathepsin B antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:110. In some embodiments, an anti-cathepsin B antibody, or fragment thereof, comprises a light chain variable region comprising the amino acid sequence of SEQ ID NO:110. In some embodiments, an anti-cathepsin B antibody, or fragment thereof, comprises a light chain variable region consisting of the amino acid sequence of SEQ ID NO:110.

In some embodiments, an anti-cathepsin B antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:85. In some embodiments, an anti-cathepsin B antibody, or fragment thereof, comprises a heavy chain variable region comprising the amino acid sequence of SEQ ID NO:85. In some embodiments, an anti-cathepsin B antibody, or fragment thereof, comprises a heavy chain variable region consisting of the amino acid sequence of SEQ ID NO:85.

In some embodiments, an anti-cathepsin B antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:110 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:85. In some embodiments, an anti-cathepsin B antibody, or fragment thereof, comprises a light chain variable region comprising the amino acid sequence of SEQ ID NO:110 and further comprises a heavy chain variable region comprising the amino acid sequence of SEQ ID NO:85. In some embodiments, an anti-cathepsin B antibody, or fragment thereof, comprises a light chain variable region consisting of the amino acid sequence of SEQ ID NO:110 and further comprises a heavy chain variable region consisting of the amino acid sequence of SEQ ID NO:85.

Anti-MMP-12 Antibodies or Fragments Thereof

Certain embodiments also provide antibodies and antigen-binding portions of antibodies that specifically bind to MMP-12 (i.e., an anti-MMP-12 antibody, or fragment thereof). Human matrix metalloproteinase (MMP)-12 (Gene ID=4321), is a macrophage elastase. MMP-12 is secreted by macrophages at sites of inflammation (Lagente, et al., (2009). *Expert Opin Ther Targets,* 13(3), 287-295), and the abnormal expression of MMP-12 leads to tissue damage that contributes to coronary artery and cerebral vascular disease (Liu, et al., (2015). *Sci Rep,* 5, 17189), metastatic cancer (Shipley, et al., (1996). *Proc Natl Acad Sci USA,* 93(9), 3942-3946), and a variety of other diseases such as pulmonary disease (Molet, et al., (2005). *Inflamm Res,* 54(1), 31-36), psoriatic disease (Mezentsev, et al., (2014). *Gene,* 540(1), 1-10), and inflammatory and rheumatoid arthritis (Liu, et al., (2004). *Arthritis Rheum,* 50(10), 3112-3117).

In some embodiments, an anti-MMP-12 antibody, or fragment thereof, comprises: (1) one or more complementarity determining region (CDR) sequences; (2) a heavy chain variable region sequence; and/or (3) a light chain variable region sequence (e.g., as described herein, such as in Table 8 below).

In certain embodiments, an isolated anti-MMP-12 antibody or fragment thereof, comprises one or more CDRs selected from the group consisting of:

(a) a light chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of RASQSVSSAVA (SEQ ID NO:34);

(b) a light chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SASSLYS (SEQ ID NO:35);

(c) a light chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of QQTFYPFT (SEQ ID NO:113); QQSSHYASPPIT (SEQ ID NO:119), and QQAYYGYLFT (SEQ ID NO:125);

(d) a heavy chain CDR1 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one GFNLYYSYMH (SEQ ID NO:115); GFNLSYSYMH (SEQ ID NO:121), and GFNLSYYSMH (SEQ ID NO:127);

(e) a heavy chain CDR2 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SISSYYGYTSYADSVK (SEQ ID NO:116), SIYPSYGSTYYADSVK (SEQ ID NO:122), and YIYPYYGSTYYADSVK (SEQ ID NO:128); and (f) a heavy chain CDR3 having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one SPIVYYELFMFIDMGAQGWKYGMDY (SEQ ID NO:117), DLEESLPKRARTAVSKELESVPYVMDY (SEQ ID NO:123), and FLLSIGKLFVGDGSILHVWLYGMDY (SEQ ID NO:129).

In some embodiments, an anti-MMP-12 antibody, or fragment thereof, comprises two, three, four, five or six CDRs as described above (e.g., each CDR is selected from one of (a)-(f)).

In certain embodiments, the anti-MMP-12 antibody, or fragment thereof, as described herein comprises one or more CDRs selected from the group consisting of:

(a) a light chain CDR1 comprising the amino acid sequence of SEQ ID NO:34;

(b) a light chain CDR2 comprising the amino acid sequence of SEQ ID NO:35;

(c) a light chain CDR3 comprising the amino acid sequence of any one of SEQ ID NOs:113, 119, and 125;

(d) a heavy chain CDR1 comprising the amino acid sequence of any one of SEQ ID NOs:115, 121, and 127;

(e) a heavy chain CDR2 comprising the amino acid sequence of any one of SEQ ID NOs:116, 122 and 128; and (f) a heavy chain CDR3 comprising the amino acid sequence of any one of SEQ ID NOs:117, 123, and 129.

In some embodiments, an anti-MMP-12 antibody, or fragment thereof, comprises two, three, four, five or six CDRs as described above (e.g., each CDR is selected from one of (a)-(f)).

In some embodiments, an anti-MMP-12 antibody, or a fragment thereof, comprises a light chain sequence, or a fragment thereof, and/or a heavy chain sequence, or a fragment thereof, derived from any of the following antibodies described herein: LG4, LH6 and LH11.

The amino acid sequences of the light chain variable region (VL) and heavy chain variable region (VH) of these anti-MMP-12 antibody clones are set forth in Table 8 below.

In certain embodiments, an anti-MMP-12 antibody, or fragment thereof, comprises a VL as in any of the embodiments provided herein, and/or a VH as in any of the embodiments provided herein.

In certain embodiments, an anti-MMP-12 antibody described herein, or fragment thereof, comprises a light chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

(SEQ ID NO: 112)
(a) DIQMTQSPSSLSASVGDRVTITCRASQSVSSAVAWYQQKPGKAPKL

LIYSASSLYSGVPSRFSGSRSGTDFTLTISSLQPEDFATYYCQQTFYPFT

FGQGTKVEIKR;

(SEQ ID NO: 118)
(b) DIQMTQSPSSLSASVGDRVTITCRASQSVSSAVAWYQQKPGKAPKL

LIYSASSLYSGVPSRFSGSRSGTDFTLTISSLQPEDFATYYCQQSSHYAS

PPITFGQGTKVEIKR;
and (SEQ ID NO: 124)
(c) DIQMTQSPSSLSASVGDRVTITCRASQSVSSAVAWYQQKPGKAPKL

LIYSASSLYSGVPSRFSGSRSGTDFTLTISSLQPEDFATYYCQQAYYGYL

FTFGQGTKVEIKR.

In some embodiments, an anti-MMP-12 antibody, or fragment thereof, comprises a light chain variable region comprising the amino acid sequence of any one of SEQ ID NOs:112, 118 and 124. In some embodiments, an anti-MMP-12 antibody, or fragment thereof, comprises a light chain variable region consisting of the amino acid sequence of any one of SEQ ID NOs: 112, 118 and 124.

In certain embodiments, an isolated anti-MMP-12 antibody described herein, or fragment thereof, comprises a heavy chain variable region comprising an amino acid sequence that has at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of:

(SEQ ID NO: 114)
(a) EVQLVESGGGLVQPGGSLRLSCAASGFNLYYSYMHWVRQAPGKGLE

WVASISSYYGYTSYADSVKGRFTISADTSKNTAYLQMNSLRAEDTAVYYC

ARSPIVYYELFMFIDMGAQGWKYGMDYWGQGTLVTVSSAS;

(SEQ ID NO: 120)
(b) EVQLVESGGGLVQPGGSLRLSCAASGFNLSYSYMHWVRQAPGKGLE

WVASIYPSYGSTYYADSVKGRFTISADTSKNTAYLQMNSLRAEDTAVYYC

ARDLEESLPKRARTAVSKELESVPYVMDYWGQGTLVTVSSAS;
and (SEQ ID NO: 126)
(c) EVQLVESGGGLVQPGGSLRLSCAASGFNLSYYSMHWVRQAPGKGLE

WVAYIYPYYGSTYYADSVKGRFTISADTSKNTAYLQMNSLRAEDTAVYYC

ARFLLSIGKLFVGDGSILHVWLYGMDYWGQGTLVTVSSAS.

In some embodiments, an anti-MMP-12 antibody, or fragment thereof, comprises a heavy chain variable region comprising the amino acid sequence of any one of SEQ ID NOs:114, 120, and 126. In some embodiments, an anti-MMP-12 antibody, or fragment thereof, comprises a heavy chain variable region consisting of the amino acid sequence of any one of SEQ ID NOs:114, 120, and 126.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:112, 118 and 124 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to any one of SEQ ID NOs:114, 120, and 126.

In some embodiments, an anti-MMP-12 antibody, or fragment thereof, comprises a light chain variable region consisting of an amino acid sequence of SEQ ID NOs:112, 118 and 124 and further comprises a heavy chain variable region consisting of an amino acid sequence of SEQ ID NOs: 114, 120, and 126.

Clone LG4

In some embodiments, an anti-MMP-12 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:113. In some embodiments, an anti-MMP-12 antibody, or fragment thereof, comprises a heavy chain CDR1 comprising the amino acid sequence of SEQ ID NO:115, a heavy chain CDR2 comprising the amino acid sequence of SEQ ID NO:116, and a heavy chain CDR3 comprising the amino acid sequence of SEQ ID NO:117. In some embodiments, an anti-MMP-12 antibody, or fragment thereof, comprises a light chain CDR1-3 and a heavy chain CDR1-3 comprising the amino acid sequences of SEQ ID NOs:34, 35, 113, 115, 116, and 117, respectively. In some embodiments, an anti-MMP-12 antibody, or fragment thereof, comprises a light chain CDR1-3 and a heavy chain CDR1-3 consisting of the amino acid sequences of SEQ ID NOs:34, 35, 113, 115, 116, and 117, respectively.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:112. In some embodiments, an anti-MMP-12 antibody, or fragment thereof, comprises a light chain variable region comprising the amino acid sequence of SEQ ID NO:112. In some embodiments, an anti-MMP-12 antibody, or fragment thereof, comprises a light chain variable region consisting of the amino acid sequence of SEQ ID NO:112.

In some embodiments, an anti-MMP-12 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:114. In some embodiments, an anti-MMP-12 antibody, or fragment thereof, comprises a heavy chain variable region comprising the amino acid sequence of SEQ ID NO:114. In some embodiments, an anti-MMP-12 antibody, or fragment thereof, comprises a heavy chain variable region consisting of the amino acid sequence of SEQ ID NO:114.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:112 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:114. In some embodiments, an anti-MMP-12 antibody, or fragment thereof, comprises a light chain variable region comprising the amino acid sequence of SEQ ID NO:112 and further comprises a heavy chain variable region comprising the amino acid sequence of SEQ ID NO:114. In some embodiments, an anti-MMP-12 antibody, or fragment thereof, comprises a light chain variable region consisting of the amino acid sequence of SEQ ID NO:112 and further comprises a heavy chain variable region consisting of the amino acid sequence of SEQ ID NO:114.

Clone LH6

In some embodiments, an anti-MMP-12 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:119. In some embodiments, an anti-MMP-12 antibody, or fragment thereof, comprises a heavy chain CDR1 comprising the amino acid sequence of SEQ ID NO:121, a heavy chain CDR2 comprising the amino acid sequence of SEQ ID NO:122, and a heavy chain CDR3 comprising the amino acid sequence of SEQ ID NO:123. In some embodiments, an anti-MMP-12 antibody, or fragment thereof, comprises a light chain CDR1-3 and a heavy chain CDR1-3 comprising the amino acid sequences of SEQ ID NOs:34, 35, 119, 121, 122, and 123, respectively. In some embodiments, an anti-MMP-12 antibody, or fragment thereof, comprises a light chain CDR1-3 and a heavy chain CDR1-3 consisting of the amino acid sequences of SEQ ID NOs:34, 35, 119, 121, 122, and 123, respectively.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:118. In some embodiments, an anti-MMP-12 antibody, or fragment thereof, comprises a light chain variable region comprising the amino acid sequence of SEQ ID NO:118. In some embodiments, an anti-MMP-12 antibody, or fragment thereof, comprises a light chain variable region consisting of the amino acid sequence of SEQ ID NO:118.

In some embodiments, an anti-MMP-12 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:120. In some embodiments, an anti-MMP-12 antibody, or fragment thereof, comprises a heavy chain variable region comprising the amino acid sequence of SEQ ID NO:120. In some embodiments, an anti-MMP-12 antibody, or fragment thereof, comprises a heavy chain variable region consisting of the amino acid sequence of SEQ ID NO:120.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:118 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:120. In some embodiments, an anti-MMP-12 antibody, or fragment thereof, comprises a light chain variable region comprising the amino acid sequence of SEQ ID NO:118 and further comprises a heavy chain variable region comprising the amino acid sequence of SEQ ID NO:120. In some embodiments, an anti-MMP-12 antibody, or fragment thereof, comprises a light chain variable region consisting of the amino acid sequence of SEQ ID NO:118 and further comprises a heavy chain variable region consisting of the amino acid sequence of SEQ ID NO:120.

Clone LH11

In some embodiments, an anti-MMP-12 antibody, or fragment thereof, comprises a light chain CDR1 comprising the amino acid sequence of SEQ ID NO:34, a light chain CDR2 comprising the amino acid sequence of SEQ ID NO:35, and a light chain CDR3 comprising the amino acid sequence of SEQ ID NO:125. In some embodiments, an anti-MMP-12 antibody, or fragment thereof, comprises a heavy chain CDR1 comprising the amino acid sequence of SEQ ID NO:127, a heavy chain CDR2 comprising the amino acid sequence of SEQ ID NO:128, and a heavy chain CDR3 comprising the amino acid sequence of SEQ ID NO:129. In some embodiments, an anti-MMP-12 antibody, or fragment thereof, comprises a light chain CDR1-3 and a heavy chain CDR1-3 comprising the amino acid sequences of SEQ ID NOs:34, 35, 125, 127, 128, and 129, respectively. In some embodiments, an anti-MMP-12 antibody, or fragment thereof, comprises a light chain CDR1-3 and a heavy chain CDR1-3 consisting of the amino acid sequences of SEQ ID NOs:34, 35, 125, 127, 128, and 129, respectively.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:124. In some embodiments, an anti-MMP-12 antibody, or fragment thereof, comprises a light chain variable region comprising the amino acid sequence of SEQ ID NO:124. In some embodiments, an anti-MMP-12 antibody, or fragment thereof, comprises a light chain variable region consisting of the amino acid sequence of SEQ ID NO:124.

In some embodiments, an anti-MMP-12 antibody, or fragment thereof, comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:126. In some embodiments, an anti-MMP-12 antibody, or fragment thereof, comprises a heavy chain variable region comprising the amino acid sequence of SEQ ID NO:126. In some embodiments, an anti-MMP-12 antibody, or fragment thereof, comprises a heavy chain variable region consisting of the amino acid sequence of SEQ ID NO:126.

In some embodiments, an anti-MMP-12 antibody, or fragment thereof, comprises a light chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:124 and further comprises a heavy chain variable region comprising an amino acid sequence that has at least about 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:126. In some embodiments, an anti-MMP-12 antibody, or fragment thereof, comprises a light chain variable region comprising the amino acid sequence of SEQ ID NO:124 and further comprises a heavy chain variable region comprising the amino acid sequence of SEQ ID NO:126. In some embodiments, an anti-MMP-12 antibody, or fragment thereof, comprises a light chain variable region consisting of the amino acid sequence of SEQ ID NO:124 and further comprises a heavy chain variable region consisting of the amino acid sequence of SEQ ID NO:126.

Certain Embodiments of Additional Antibody Attributes

In certain embodiments, an isolated anti-MMP-14 antibody, an isolated anti-MMP-12 antibody, an isolated anti-BACE-1 antibody, an isolated anti-Alp2 antibody and/or an isolated anti-cathepsin B antibody described herein, or fragment thereof, further comprises at least one heavy chain constant region and/or at least one light chain constant region. Thus, in certain embodiments, the light chain variable region is linked (e.g., through a linker or a direct bond, such as a peptide bond) to a light chain constant region. In certain embodiments, the heavy chain variable region is linked to at least one heavy chain constant region (e.g., 1, 2, or 3). In certain embodiments, the heavy and light chains are linked via one or more disulfide bonds.

In certain embodiments, the antibody or fragment thereof is a recombinant antibody or fragment thereof. In certain embodiments, the antibody or fragment thereof is a chimeric antibody or fragment thereof. In certain embodiments, the antibody or fragment thereof is humanized.

In certain embodiments, an antibody of the invention is a monoclonal antibody or a fragment thereof. In some embodiments, the monoclonal antibody, or fragment thereof, recognizes an epitope within human MMP-14. In some embodiments, the monoclonal antibody, or fragment thereof, recognizes an epitope within human MMP-12. In some embodiments, the monoclonal antibody, or fragment thereof, recognizes an epitope within human BACE-1. In some embodiments, the monoclonal antibody, or fragment thereof, recognizes an epitope within human Alp2. In some embodiments, the monoclonal antibody, or fragment thereof, recognizes an epitope within human cathepsin B.

In certain embodiments, antibody, or fragment thereof, is a fragment. In certain embodiments, the fragment comprises an antigen-binding domain or a variable region. For example, in certain embodiments, the fragment is a fragment antigen-binding (Fab), F(ab')2, Fv, single-chain Fv (scFv), CDR (e.g., CDR-H3), diabody (diabodies), linear antibody or a multispecific antibody prepared from an antibody fragment. In certain embodiments, the fragment is a Fab fragment (e.g., a Fab comprising a human antibody scaffold). In other embodiments, the fragment is a CDR-H3.

In another embodiment, the antibody is a substantially full length antibody, e.g., an IgG antibody, or other antibody class or isotype as described herein.

In certain embodiments, an isolated antibody described herein, or fragment thereof, is an inhibitor of a target protease (e.g., MMP-14, MMP-12, BACE-1, Alp2 or cathepsin B).

The term "inhibitor of a target protease" as used herein refers to an antibody or fragment thereof that is capable of inhibiting the function of the protease (e.g., inhibits enzymatic activity, e.g., inhibits protease cleavage activity). For example, in certain embodiments, the antibody, or fragment thereof, detectably inhibits the biological activity of the protease as measured, e.g., using an assay described herein. In certain embodiments, the antibody, or fragment thereof, inhibits the biological activity of the protease by at least about 5%, at least about 10%, at least about 20%, at least about 30%, at least about 40%, at least about 50%, at least about 60%, at least about 70%, at least about 80%, or at least about 90%. In certain embodiments, the antibody or fragment thereof is a selective inhibitor of the target protease. For example, an antibody of the invention may be at least 5, at least 10, at least 50, at least 100, at least 500, or at least 1,000 fold selective for the target protease over another protease in a selected assay (e.g., an assay described in the Examples herein).

In certain embodiments, an isolated antibody described herein, or fragment thereof, further comprises a detectable label.

Certain embodiments of the invention provide an antibody or fragment thereof as described herein.

Certain embodiments of the invention provide a method as described herein for making an antibody of the invention or fragment thereof.

Certain embodiments of the invention provide a method as described herein for isolating an antibody of the invention or fragment thereof from an antibody library.

Certain embodiments of the invention provide an antibody or fragment thereof isolated by a method as described herein.

Certain embodiments provide a composition comprising an antibody as described herein, or fragment thereof, and a carrier. In certain embodiments, the composition is a pharmaceutical composition comprising a pharmaceutically acceptable carrier.

Certain embodiments provide a kit comprising an isolated antibody as described herein, or fragment thereof, packaging material, and instructions for administering the antibody, or a fragment thereof, to a mammal to treat a disease or disorder. In certain embodiments, the kit further comprises at least one other therapeutic agent.

As used herein, the term "antibody" includes a single-chain variable fragment (scFv or "nanobody"), humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

A scFv is a fusion protein of the variable region of the heavy (VH) and light chains (VL) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the VH to the carboxy-terminus of the VL, or the linker may link the carboxy-terminus of the VH to the amino-terminus of the VL. Divalent (also called bivalent) scFvs can be generated by linking two scFvs. For example, a divalent scFv can be made by generating a single peptide containing two VH and two VL regions. Alternatively, two peptides, each containing a single VH and a single VL region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are typically produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention may comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., *Proc. Natl. Acad. Sci. USA* 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more specifically at least 75%, even more specifically at least 80%, still more specifically at least 85%, yet more specifically at least 90%, and most specifically at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs.

Specific techniques for such analyses are known in the art (see the website of the National Center for Biotechnology Information (NCBI), Basic Local Alignment Search Tool (BLAST); www.ncbi.nlm.nih.gov).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/ Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies which comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid sidechain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and specifically within 35%, and still more specifically within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, may be obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., *Cancer Res.* (1993) 53, 851-856).

As described herein, an antibody of the invention or a fragment thereof may comprise a synthetic CDR-H3. Additionally, an antibody of the invention may also be a recombinant antibody (e.g., a humanized or chimeric antibody) or a fragment thereof. Accordingly, such an antibody of the invention or fragment thereof would not be a product of nature. Additionally, an antibody of the invention or a fragment thereof may comprise markedly different characteristics (e.g., structural, functional and/or other properties) as compared to naturally occurring antibody.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')2, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer (VH-VL dimer) wherein the variable regions of each of the heavy chain and light chain are strongly connected by a noncovalent bond. The three CDRs of each of the variable regions interact with each other to form an antigen-binding site on the surface of the VH-VL dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a specific antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as *E. coli*, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region (VL) and a heavy chain variable region (VH) in an identical chain are connected via a short linker, for example, a linker of about five residues, so that they cannot bind together. Because the linker between the two is too short, the VL and VH in the same polypeptide chain cannot form a single chain V region fragment, but instead form a dimer. Thus, a diabody has two antigen-binding domains. When the VL and VH regions against the two types of antigens (a and b) are combined to form VLa-VHb and VLb-VHa via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, such as a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133, 988).

Nucleic Acids, Expression Cassettes, Vectors and Cells

Certain embodiments of the invention provide an isolated nucleic acid encoding an antibody or fragment thereof as described herein. In certain embodiments, the nucleic acid further comprises a promoter.

Certain embodiments of the invention provide an expression cassette comprising a nucleic acid as described herein and a promoter.

Certain embodiments of the invention provide a vector (e.g., a phagemid or plasmid) comprising a nucleic acid or an expression cassette as described herein.

Certain embodiments of the invention provide a cell (e.g., a bacterial cell) comprising a nucleic acid, expression cassette or vector as described herein.

Certain embodiments of the invention provide a phage particle comprising a vector as described herein.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucl. Acids Res., 19:508 (1991); Ohtsuka et al., JBC, 260:2605 (1985); Rossolini et al., Mol. Cell. Probes, 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more specifically at least 150 nucleotides, and still more specifically at least 400 nucleotides. If not employed for expressing, a "portion" or "fragment" means at least 9, specifically 12, more specifically 15, even more specifically at least 20, consecutive nucleotides, e.g., probes and primers (oligonucleotides), corresponding to the nucleotide sequence of the nucleic acid molecules of the invention.

The terms "protein," "peptide" and "polypeptide" are used interchangeably herein.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, culture medium may represent less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, CABIOS, 4:11 (1988); the local homology algorithm of Smith et al., Adv. Appl. Math., 2:482 (1981); the homology alignment algorithm of Needleman and Wunsch, JMB, 48:443 (1970); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990), modified as in Karlin and Altschul, Proc. Natl. Acad. Sci. USA, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994). The ALIGN program is based on the algorithm of Myers and Miller, supra. The BLAST programs of Altschul et al., JMB, 215: 403 (1990); Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more specifically less than about 0.01, and most specifically less than about 0.001.

To obtain gapped alignments for comparison purposes, Gapped BLAST (in BLAST 2.0) can be utilized as described in Altschul et al., Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

Methods of Use

Certain embodiments provide a method of detecting the presence of a target protease in a cell, the method comprising contacting the cell with an isolated antibody, or fragment thereof, as described herein and detecting whether a complex is formed between the antibody and the target protease, wherein the target protease is selected from the group consisting of MMP-14, MMP-12, BACE-1, Alp2 and cathepsin B. In certain embodiments, the target protease is selected from the group consisting of MMP-14, BACE-1, Alp2 and cathepsin B. In certain embodiments, the target protease is MMP-14. In certain embodiments, the target protease is MMP-12. In certain embodiments, the target protease is BACE-1. In certain embodiments, the target protease is Alp2. In certain embodiments, the target protease is cathepsin B.

In certain embodiments, the cell is contacted in vitro. In certain embodiments, the cell is contacted in vivo.

Certain embodiments provide a method of inhibiting the activity of a target protease (e.g., MMP-14, MMP-12, BACE-1, Alp2 or cathepsin B) (e.g., the protease cleavage activity), comprising contacting the target protease with an isolated antibody, or fragment thereof, as described herein. In certain embodiments, the target protease is contacted in vitro. In certain embodiments, the target protease is contacted in vivo. Methods for measuring the activity of a target protease are known in the art. For example, in certain embodiments, an assay described herein may be used. In certain embodiments, an antibody of the invention or a fragment thereof inhibits the enzymatic activity of the protease by at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 99% or at least about 100% as compared to a control.

Certain embodiments also provide a method for treating a disease or disorder in a mammal, comprising administering an effective amount of an isolated antibody, or fragment thereof, as described herein to the mammal.

In certain embodiments, the method further comprises administering at least one additional therapeutic agent to the mammal.

Certain embodiments provide an isolated antibody, or fragment thereof, as described herein for the prophylactic or therapeutic treatment of a disease or disorder.

Certain embodiments provide the use of an isolated antibody, or fragment thereof, as described herein to prepare a medicament for the treatment of a disease or disorder in a mammal.

In certain embodiments, the disease or disorder is cancer and the antibody is an anti-MMP-14 antibody as described herein, or a fragment thereof.

In certain embodiments, the disease or disorder is cancer and the antibody is an anti-cathepsin B antibody as described herein, or a fragment thereof.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and melanoma.

In certain embodiments, the disease or disorder is Alzheimer's disease and the antibody is an anti-BACE-1 antibody as described herein, or a fragment thereof.

In certain embodiments, the disease or disorder is aspergillosis and the antibody is an anti-Alp2 antibody as described herein, or a fragment thereof.

In certain embodiments, the disease or disorder is inflammation or an inflammatory associated disease and the antibody is an anti-MMP-12 antibody as described herein, or a fragment thereof. In certain embodiments, the disease or disorder is a neurological disease and the antibody is an anti-MMP-12 antibody as described herein, or a fragment thereof. In certain embodiments, the disease or disorder is coronary artery or cerebral vascular disease; cancer (e.g., metastatic cancer); pulmonary disease; a psoriatic disease; inflammatory arthritis; or rheumatoid arthritis; and the antibody is an anti-MMP-12 antibody as described herein, or a fragment thereof.

Certain embodiments provide an isolated antibody, or fragment thereof, as described herein for use in medical therapy.

Administration

For in vivo use, an antibody of the invention, or fragment thereof, is generally incorporated into a pharmaceutical composition prior to administration. Within such compositions, one or more antibodies of the invention may be present as active ingredient(s) (i.e., are present at levels sufficient to provide a statistically significant effect on the symptoms of a relevant disease, as measured using a representative assay). A pharmaceutical composition comprises one or more such antibodies in combination with any pharmaceutically acceptable carrier(s) known to those skilled in the art to be suitable for the particular mode of administration. In addition, other pharmaceutically active ingredients (including other therapeutic agents) may, but need not, be present within the composition.

The term "therapeutically effective amount," in reference to treating a disease state/condition, refers to an amount of an antibody or fragment thereof either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In certain embodiments, the present antibodies (i.e., antibody of the present invention or a fragment thereof) may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the antibody may be combined with one or more excipients and used in the form of ingestible tablets, buccal tablets, troches, capsules, elixirs, suspensions, syrups, wafers, and the like. Such compositions and preparations should contain at least 0.1% of an antibody of the present invention. The percentage of the compositions and preparations may, of course, be varied and may conveniently be between about 2 to about 60% of the weight of a given unit dosage form. The amount of antibody in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the antibody, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the antibody may be incorporated into sustained-release preparations and devices.

The antibody may also be administered intravenously or intraperitoneally by infusion or injection. Solutions of the antibody may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the antibody that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the antibody in the required amount in the appropriate solvent with various of the other ingredients enumerated above, as required, followed by filter sterilization. In the case of sterile powders for the preparation of sterile injectable solutions, the methods of preparation are vacuum drying and the freeze drying techniques, which yield a powder of the antibody plus any additional desired ingredient present in the previously sterile-filtered solutions.

For topical administration, the present antibodies may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present antibodies can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the antibodies of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the antibodies of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of an antibody of the present invention required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations.

Antibodies of the invention can also be administered in combination with other therapeutic agents and/or treatments, such as other agents or treatments that are useful to treat a disease or disorder described herein. Additionally, one or more antibodies of the invention, or fragments thereof, may be administered (e.g., a combination of antibodies, or fragments thereof, may be administered). Accordingly, one embodiment the invention also provides a composition comprising an antibody of the invention, or a fragment thereof, at least one other therapeutic agent, and a pharmaceutically acceptable diluent or carrier. The invention also provides a kit comprising an antibody of the invention, or a fragment thereof, at least one other therapeutic agent, packaging material, and instructions for administering an antibody of the invention, or a fragment thereof, and the other therapeutic agent or agents to an animal to treat a disease or disorder described herein.

As used herein, the term "therapeutic agent" refers to any agent or material that has a beneficial effect on the mammalian recipient.

Screening Methods

Current antibody discovery methods typically rely on the capability of antibody to bind to a target protein rather than the capability of the antibody to modulate the function of the target protein. Therefore, the identification of antibodies having inhibitory capabilities can be challenging using traditional techniques. As described herein, an alternative method for identifying and selecting antibodies having inhibitory functions has been developed.

Accordingly, certain embodiments of the invention provide a method of isolating an antibody or a fragment thereof from an antibody library, wherein the antibody or fragment thereof is capable of inhibiting a target protease, the method comprising: periplasmically co-expressing in a bacterial cell: 1) an antibody, or fragment thereof, from the library; 2) the target protease or an enzymatic domain thereof (e.g., extracellular or catalytic domain, or a mutant thereof); and 3) a modified β-lactamase that comprises a peptide sequence that is capable of being cleaved by the target protease; wherein the bacterial cell is cultured in the presence of a β-lactam antibiotic. In such a method, an antibody or fragment thereof, that is capable of inhibiting the target protease will block the enzymatic activity of the target protease and prevent the cleavage of the β-lactamase, resulting in cell growth in the presence of a β-lactam antibiotic. Alternatively, if an antibody or fragment thereof is not capable of inhibiting the target protease, the β-lactamase will be cleaved, leading to cell death in the presence of a β-lactam antibiotic.

In certain embodiments, such a method is repeated 2 or more times.

In certain embodiments, the method further comprises transfecting one or more plasmids comprising a nucleic acid encoding the antibody, or fragment thereof, a nucleic acid encoding the target protease, or domain thereof, and a nucleic acid encoding the modified β-lactamase into the bacterial cell. In certain embodiments, nucleic acids encoding the antibody, the target protease and the modified β-lactamase are present in a single plasmid. In certain embodiments, a bacterial cell is transfected with two plasmids, wherein the first plasmid comprises two different nucleic acids selected from the group consisting of a nucleic acid encoding the antibody, a nucleic acid encoding the target protease and a nucleic acid encoding the modified β-lactamase, and wherein the second plasmid comprises a nucleic acid not present in the first plasmid selected from the group consisting of a nucleic acid encoding the antibody, a nucleic acid encoding the target protease and a nucleic acid encoding the modified β-lactamase. In certain embodiments, a bacterial cell is transfected with two plasmids, wherein the first plasmid comprises a nucleic acid encoding the target protease and a nucleic acid encoding the modified β-lactamase, and wherein the second plasmid comprises a nucleic acid encoding the antibody. In certain embodiments, a bacterial cell is transfected with a plasmid comprising a nucleic acid encoding the antibody, a plasmid comprising a nucleic acid encoding the target protease and a plasmid comprising a nucleic acid encoding the modified β-lactamase.

In certain embodiments, the bacterial cell is an *Escherichia coli* cell.

In certain embodiments, the bacterial cell is cultured for a time sufficient for cell growth or cell death to occur.

In certain embodiments, the modified β-lactamase is a modified TEM-1 (see, e.g., SEQ ID NOs:131 and 153). In certain embodiments, the cleavable peptide sequence is inserted between Gly196 and Glu197 of TEM-1 (see, e.g., SEQ ID NO:130). In certain embodiments, the modified β-lactamase is described herein. In certain embodiments, the cleavable peptide sequence is a sequence described herein (e.g., any one of SEQ ID NOs:133-138). In certain embodiments, a linker group is operably linked to the N' and/or C' terminus of the cleavable peptide sequence. In certain embodiments, the linker group is glycine/serine rich (e.g., SRGSGXSGGPW SEQ ID NOs:132 and 152, wherein "X" is the cleavable peptide sequence; see, SEQ ID NOs:131 and 153).

In certain embodiments, the bacterial cell is cultured in the presence of ampicillin.

In certain embodiments, the target protease is a matrix metalloproteinase (MMP). In certain embodiments, the MMP is a human MMP. In certain embodiments, the MMP is a MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-21, MMP-23A, MMP-23B, MMP-24, MMP-25, MMP-26, MMP-27 or MMP-28. In certain embodiments, the MMP is MMP-2. In certain embodiments, the MMP is MMP-9. In certain embodiments, the MMP is MMP-12. In certain embodiments, the MMP is MMP-14. In certain embodiments, the protease is BACE-1. In certain embodiments, the protease is Alp2. In certain embodiments, the protease is cathepsin B.

Certain embodiments of the invention provide an antibody, or fragment thereof, isolated by a method described herein.

Certain embodiments also provide a target protease inhibition polypeptide sensor comprising a β-lactamase TEM-1 amino acid sequence and a peptide sequence that is capable of being cleaved by a target protease, wherein the intact target protease inhibition polypeptide sensor is capable of hydrolyzing a β-lactam antibiotic. In certain embodiments, the cleavable peptide sequence is inserted between Gly196 and Glu197 of TEM-1 (see, e.g., SEQ ID NOs:130-131 and 153). In certain embodiments, the cleavable peptide sequence is a sequence described herein (e.g., any one of SEQ ID NOs:133-138). In certain embodiments, a linker group is operably linked to the N' and/or C' terminus of the cleavable peptide sequence. In certain embodiments, the linker group is glycine/serine rich (e.g., SRGSGXSGGPW (SEQ ID NOs:132 and 152), wherein "X" is the cleavable peptide sequence). In certain embodiments, the target protease inhibition polypeptide sensor is a modified β-lactamase as described herein. For example, in certain embodiments, the target protease inhibition polypeptide sensor comprises SEQ ID NOs:131 and 153, wherein "X" is any one of SEQ ID NOs:133-138.

Certain embodiments of the invention provide an isolated nucleic acid encoding a target protease inhibition polypeptide sensor as described herein. In certain embodiments, the nucleic acid further comprises a promoter.

Certain embodiments of the invention provide an expression cassette comprising a nucleic acid as described herein and a promoter.

Certain embodiments of the invention provide a vector (e.g., a plasmid) comprising a nucleic acid or an expression cassette as described herein.

Certain embodiments of the invention provide a cell comprising a nucleic acid, expression cassette or vector as described herein.

The invention will now be illustrated by the following non-limiting Examples.

Example 1. Functional Selection of Protease Inhibitory Antibodies

Proteases precisely control a wide variety of physiological processes and thus are important drug targets. Compared to small molecule inhibitors, monoclonal antibodies (mAbs) are attractive as they provide needed specificity. However, finding inhibitory mAbs is often the bottleneck largely due to lack of a function-based selection method. We overcame this obstacle and successfully isolated mAbs that inhibited four therapeutic targets. Our mAb inhibitors are highly selective and deliver desired biochemical and biological functions including reduction of amyloid beta formation in vitro. The technique described here can be readily applied to many biomedically important proteases for biologic inhibitor discovery and engineering.

Results
Design of Functional Selection for Protease Inhibitory mAbs.

To select mAbs that inhibit proteases, three recombinant proteins—a clone from an antibody library, the protease of interest, and the protease substrate acting as an in vivo sensor—were produced in the same location. We hypothesize that E. coli periplasmic co-expression is ideal for this task because the oxidative environment and associated molecular chaperons facilitate disulfide formation needed to produce antibody fragments and many human proteases in their active form. In addition, large combinatorial libraries have been routinely constructed in E. coli thanks to its high transformation efficiency. The crucial aspect of this method is a cellular protease inhibition sensor—our design is to engineer β-lactamase TEM-1, a periplasmic hydrolase of β-lactam antibiotics, by inserting a protease specific cleavable peptide sequence. When the modified TEM-1 is cleaved by the protease of interest, it will lose its β-lactam hydrolytic activity, and thus the cell cannot grow in the presence of ampicillin. Conversely, when proteolytic activity of the target is blocked by a co-expressed antibody, TEM-1 will be spared to confer ampicillin resistance to the host cell. Therefore, this live or die selection can identify antibody clones that specifically inhibit the activity of the targeted protease (FIG. 1A).

Figure 5:
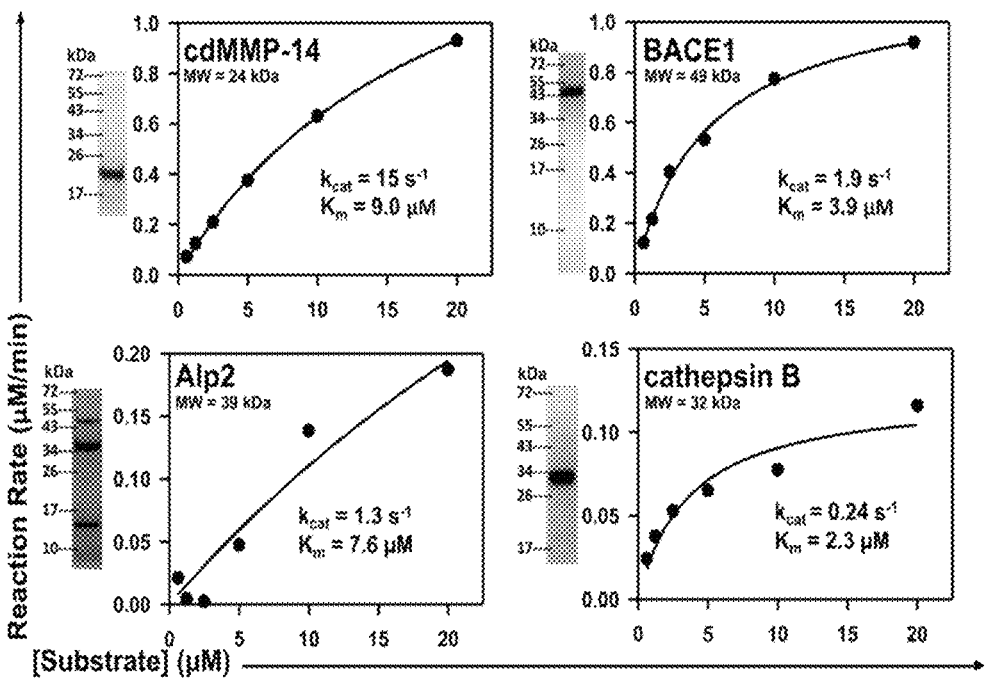
FIG. 5. Periplasmic production of extracellular/catalytic domains of human/fungal proteases in their active soluble format. Purified proteases were analyzed by SDS-PAGE, and their enzymatic kinetics were measured with FRET peptide substrates.

To demonstrate the generality of this functional selection method, we chose four disease-associated targets: MMP-14 (metastasis) (Itoh Y, Seiki M. *J Cell Physiol.* 206, 1-8 (2006)), aspartic protease beta-secretase 1 (BACE1, Alzheimer's disease) (Vassar et al., *J Neurosci.* 29, 12787-12794 (2009)), serine protease Alp2 of Aspergillusfumigatus (aspergillosis) (Abad, et al., *Rev Iberoam Micol.* 27, 155-182 (2010)), and cysteine protease cathepsin B (cancer and neurodegenerative disorders) (Gondi et al., *Expert Opin Ther Targets.* 17, 281-291 (2013)). The extracellular/catalytic domains (cd) of these targets without their propeptide sequences were cloned downstream of a pLac promoter and a pelB leader for periplasmic expression. Enzymatic assays showed that produced proteases were functional with expected activities (FIG. 5). Yields of 0.5-2.0 mg active soluble proteases per liter of culture were typically achieved (except BACE1 which was yielded 0.1 μg per liter culture), suggesting the feasibility of their inhibition by co-expressed Fabs, which are usually produced at similar level in periplasm (Nam D H, Ge X. *Biotechnol. Bioeng.* 113, 717-723 (2016)).

Distinct Selection Windows for Protease Inhibitors.

Figure 6:
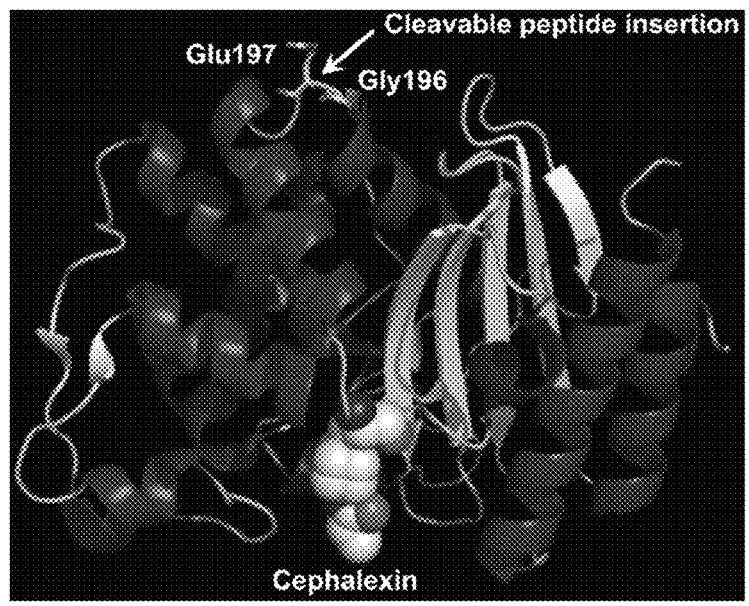
FIG. 6. Design of β-lactamase TEM1 sensor for protease inhibition. Structure (PBD, 4ZJ3) showing that the location of cleavage peptide insertion (between Gly196 and Glu197) is on a loop far away from the active site where substrates, e.g. cephalexin, bind. Images were generated by using PyMol (PDB=4ZJ2).

To select inhibitory mAbs with high potencies, protease specific substrates with relatively fast kinetics ($k_{cat}/K_m$s) were used for TEM-1 insertion sequence design. Synthetic peptide substrates SGRIGFLRTA (SEQ ID NO:133) and KLHFSKQ (SEQ ID NO:137) were chosen for cdMMP-14 and cathepsin B respectively. For BACE1, a peptide sequence EISEVKMDAEY (SEQ ID NO:135) was derived from its physiological substrate amyloid precursor protein (APP). A generic serine protease substrate KLRSSKQ (SEQ ID NO:136) was applied for Alp2, as its physiological substrate is unknown. Flanked by flexible serine-glycine linkers at both ends, i.e. GSG-peptide-SGG, these cleavable peptide sequences were introduced between Gly196 and Glu197 of TEM-1 (FIG. 6). This site is located on an exposed surface loop away from the β-lactamase active center and has been exploited for the construction of cellular sensors (Galarneau et al., *Nat Biotechnol.* 20, 619-622 (2002); Porter et al., (2007) *Anal Chem.* 79:6702-6708).

Survival rates of E. coli cells transformed with modified TEM-1 were measured on agar plates supplemented with 0-1000 μg/mL ampicillin. Results showed that the minimal inhibitory concentrations (MICs) were 500 μg/mL or higher (FIG. 1B, and FIG. 7), suggesting that peptide insertion did not disrupt TEM-1 catalytic function nor was cleaved by endogenous proteases of E. coli periplasm. However, when the associated proteases were periplasmically co-expressed, MICs dramatically decreased to 200 μg/mL or lower, indicating that proteolytic cleavages of modified TEM-1s resulted in loss of their β-lactamase activity. Overall, the significant disparity between the survival curves with (dashed lines in FIG. 1B and FIG. 7) and without co-expressed proteases (solid lines in FIG. 1B and FIG. 7) provided distinct windows for effective selection of inhibitors. Protease expression level was also up- or down-regulated by adding IPTG or glucose respectively to optimize selection conditions (Table 2). Specifically, 200 μg/mL ampicillin with 2% glucose for cdMMP-14 and 300 μg/mL ampicillin with 0.1 mM IPTG for the other tested proteases were determined. These conditions yielded a 100% survival rate in the absence of protease while nearly complete cell death (survival rates <$10^{-6}$) in the presence of protease.

Isolation of Multiple Potent mAb Inhibitors for Each Protease.

To promote generation of inhibitory mAbs targeting protease reaction clefts (Nam et al., *Proc Natl Acad Sci USA* 113, 14970-14975 (2016)), a human Fab synthetic library encoding CDR-H3s with 23-27 amino acids was constructed downstream of a phoA promoter and a STII leader (FIG. 1A). In the absence of ampicillin, transformation of obtained Fab library plasmids (1.1×$10^9$ diversity) to E. coli competent cells carrying genes of modified TEM-1 and associated protease generated 1.5-8.6×10⁸ clones. Fab libraries were subjected to functional selection for each protease inhibition under pre-determined conditions (Table 2). Surviving colonies were then individually screened by culturing in liquid media under more stringent conditions, i.e. by increasing ampicillin concentration 100 µg/mL. Taking anti-cdMMP-14 as example, 190 clones survived after the initial selection, and the secondary screening narrowed them down to 161. Among them, 40 were randomly picked for DNA sequencing, and 38 unique Fabs were identified. Applying similar procedures, monoclonal Fabs were successfully discovered for each of the other tested proteases (Table 2).

Figure 8:
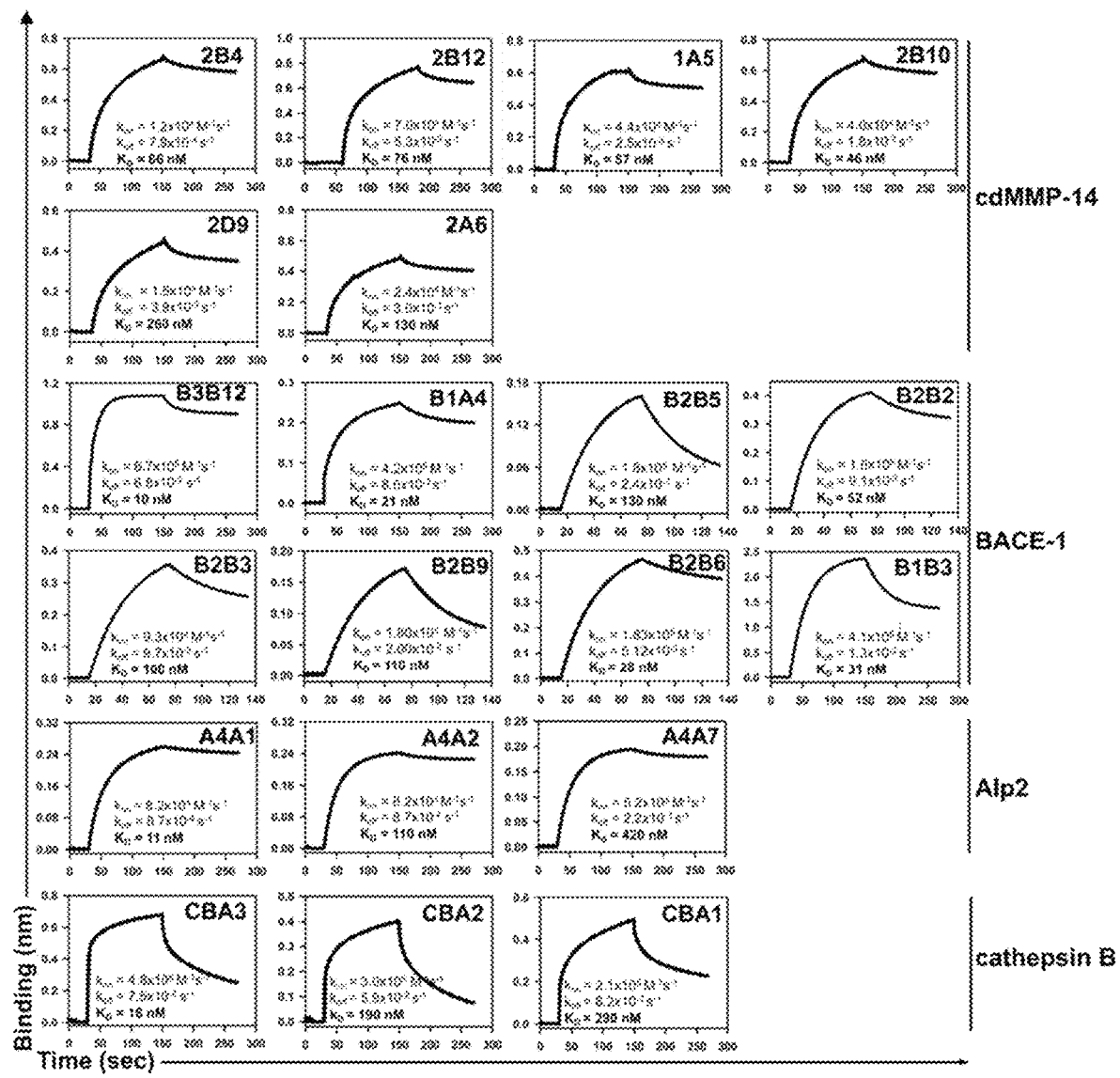
FIG. 8. Binding kinetics of isolated Fabs to protease targets. $k_{on}$ and $k_{off}$ values were measured by bio-layer interferometry and used for $K_D$ calculation. Only Fab clones with $K_f$<500 nM are shown in the same order as in Table 1.
Figure 9:
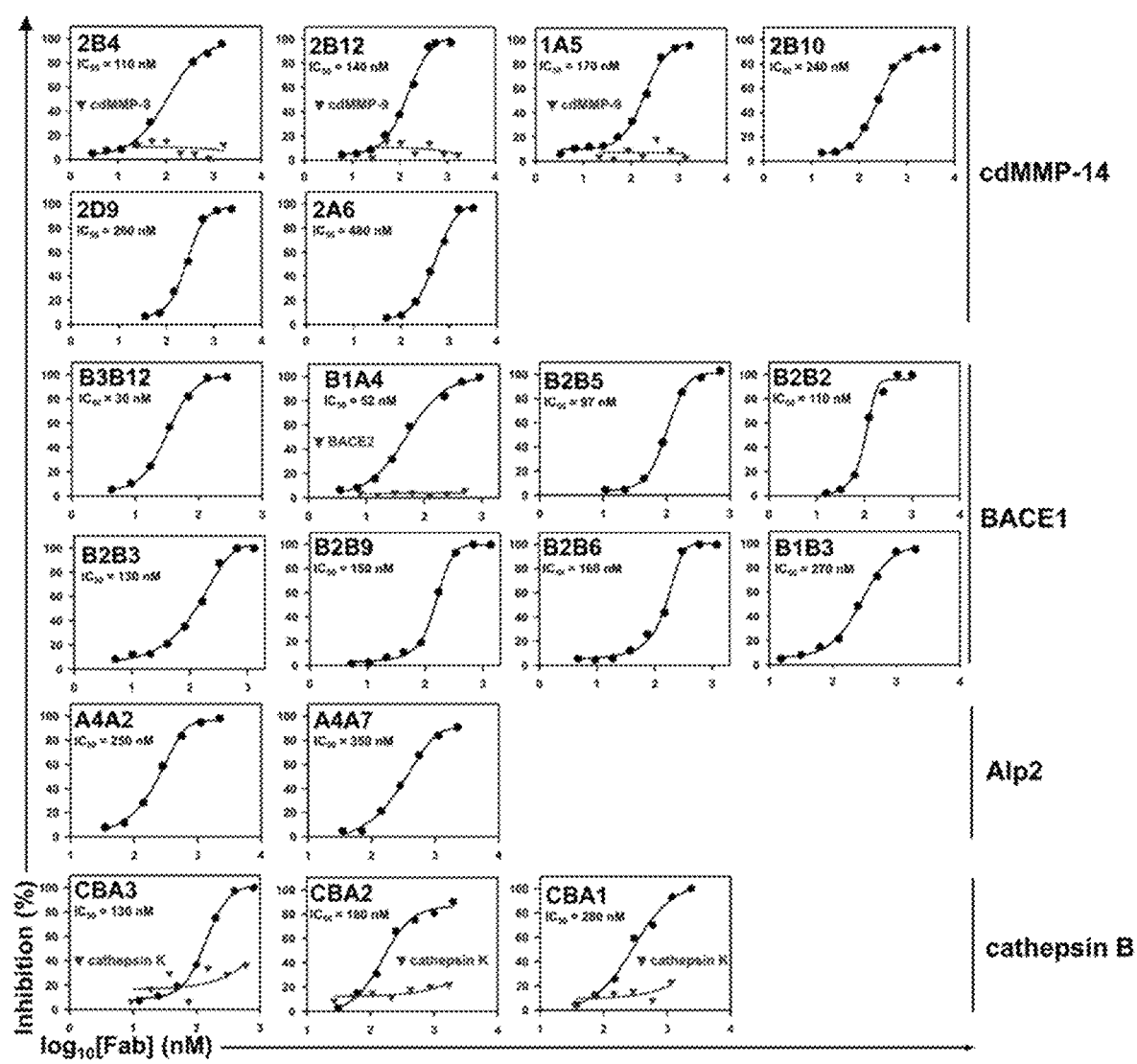
FIG. 9. Inhibition potencies of isolated Fabs. Inhibition $IC_{50}$s were measured by using FRET peptide substrates. Only Fab clones with $K_f$<500 nM are shown in the same order as in Table 1. Inhibition selectivity of representative Fabs was also tested. For anti-cdMMP9 clone H3, its IgG instead of Fab is shown.

Three to eight Fabs from each selection experiment were produced for biochemical characterizations (Table 1). Binding affinity measurements by biolayer interferometry and ELISA confirmed that all the tested Fabs bound to their protease targets with dissociation constants ($K_D$s) ranging from 10 nM to more than 1 µM (FIG. 8). Among the tested Fabs, many had $K_D$ values <250 nM. Particularly, anti-BACE1 Fab B3B12, anti-Alp2 Fab A4A1, and anti-cathepsin B Fab CBA3 exhibited a $K_D$ of 10, 11, and 16 nM respectively. Inhibitory function of purified Fabs were assayed with associated proteases and their FRET peptide substrates. Results indicated that most of the tested Fabs were inhibitors (FIG. 9). Among isolated inhibitory Fabs, numerous Fabs showed potent inhibition with calculated inhibition constant ($K_I$) values <250 nM (Table 1). Particularly, Fabs B3B12, A4A1, and CBA3 had a $K_I$ of 23, 13, and 91 nM respectively. Converting two anti-BACE1 inhibitory Fabs of nanomolar potencies into their IgG format increased the affinities and potencies as expected, e.g. B3B12 IgG exhibited $K_D$ of 7 nM and $K_I$ of 13 nM (Table 1). Rapid isolation of multiple potent inhibitory mAbs targeting all four tested proteases from >10⁸ library clones demonstrated the effectiveness and robustness of this selection system.

Inhibitory mAbs are Highly Selective, Functional on Physiological Substrates, and Proteolytically Stable.

Figures 2A, 2B:
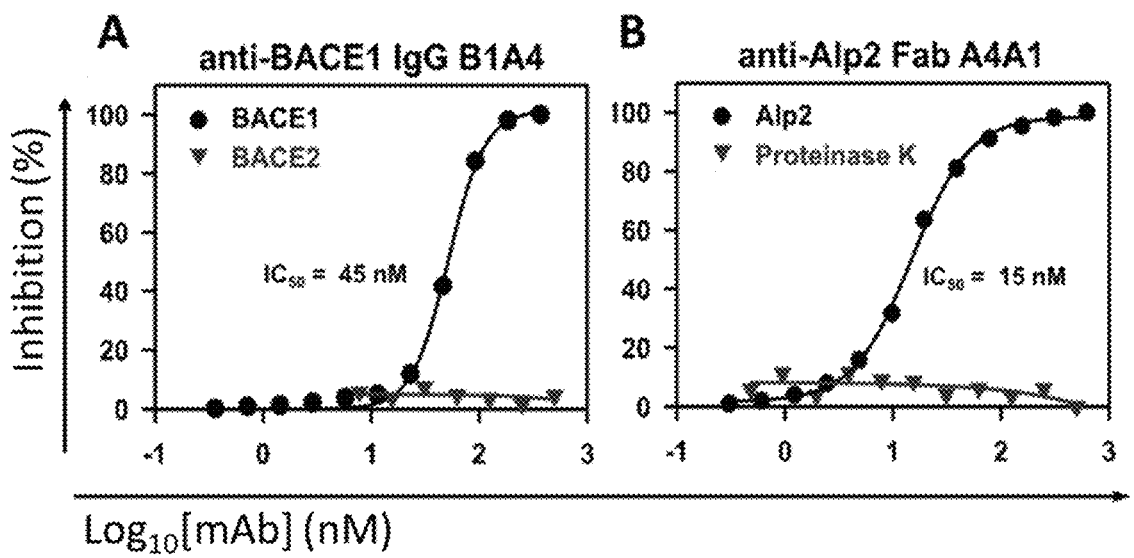
FIGS. 2A-2B. Inhibition potency and selectivity for (FIG. 2A) anti-BACE1 IgG B1B4 (FIG. 2B) anti-Alp2 Fab A4A1. Inhibition assays were measured using FRET peptide substrates.
Figure 3:
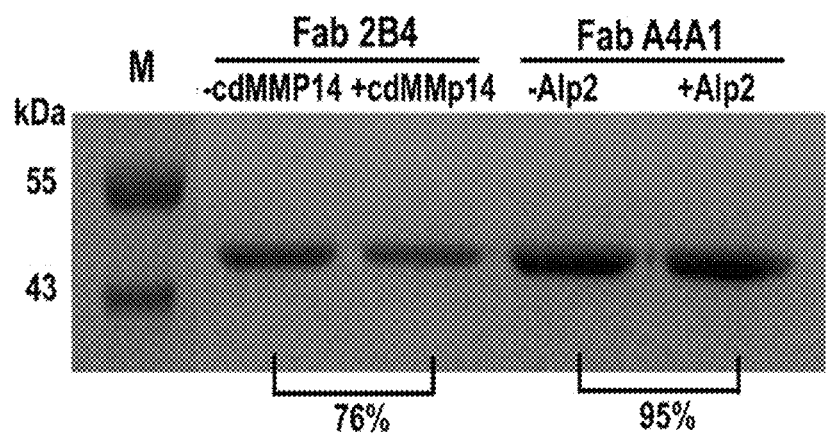
FIG. 3. In vitro proteolytic stability. SDS-PAGE of 1 µM Fabs after incubation with 1 µM of the target protease for 12 hours. Densitometric analysis was performed to determine the relative amounts of remained Fabs.
Figures 4A, 4B:
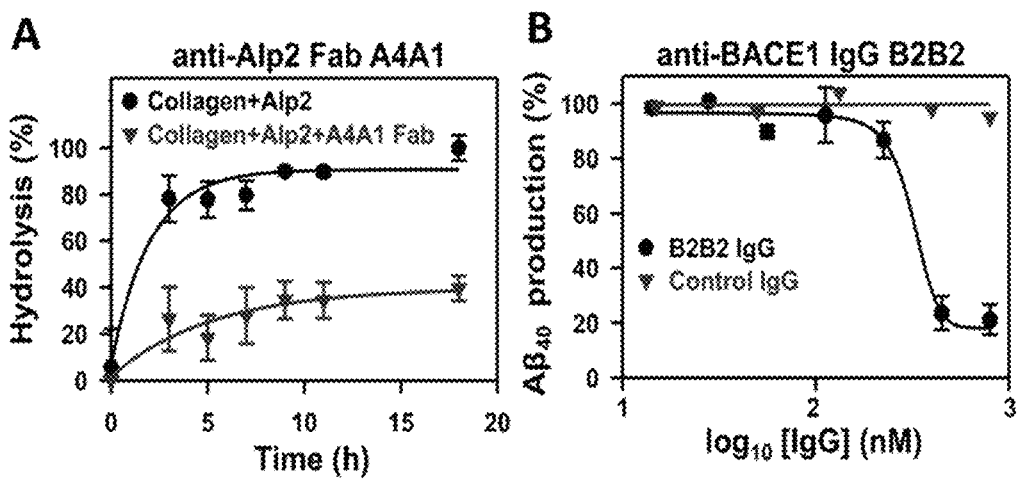
FIGS. 4A-4B. Inhibitory functions of isolated mAbs on proteolysis of physiological/macromolecular substrates.
Figure 10:
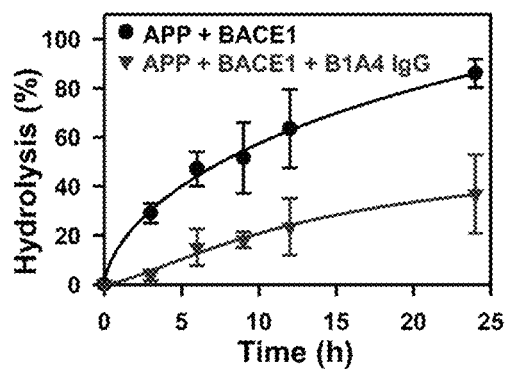
FIG. 10. Inhibitory functions of anti-BACE1 IgG B1A4 on proteolysis of amyloid precursor protein (APP). 5 µM MBP-APP was incubated with 1 µM BACE1 in the absence or presence of 1 µM IgG B1B4 at 37° C. for 24 h. Samples were taken and analyzed by SDS-PAGE to quantify amounts of remaining APP.

Inhibition selectivity of representative mAbs was tested. As results shown in FIG. 9, Fabs 2B4, 2B12 and 1A5 inhibited cdMMP-14 with $K_I$s of 96-150 nM but did not inhibit cdMMP-9 at 500 nM (FIG. 9). Similarly, IgGs B3B12 and B1A4 inhibited BACE1 with nanomolar potency ($K_I$=13 and 35 nM respectively) but not BACE2 (FIG. 2A & FIG. 9); Fab A4A1 inhibited Alp2 ($K_I$=13 nM) but not proteinase K, a broad-spectrum serine protease (FIG. 2B); and Fabs CBA3, CBA2, and CBA1 inhibited cathepsin B completely but not cathepsin K at the same Fab concentrations (FIG. 9). Next, anti-Alp2 and anti-BACE1 mAbs were examined for their inhibitory functions on the associated physiological/macromolecular substrates. Fab A4A1 reduced the hydrolysis of FITC-conjugated collagen by Alp2 from 90% to 38% (FIG. 4A); and IgG B1A4 reduced cleavage of $APP_{571-696}$ by BACE1 from 86% to 37% (FIG. 10). Furthermore, in in vitro assays by using HEK293 cells expressing APP, IgG B2B2 reduced amyloid beta (Aβ₄₀) production 80% in a dose-dependent manner with an apparent $IC_{50}$ of 330 nM (FIG. 4B). To test proteolytic stability of inhibitory antibodies in vitro, 1 µM purified Fabs were incubated with 1 µM respective protease at 37° C. SDS-PAGE revealed that after exposed to equal molar of the protease for 24 hours, Fabs 2B4 and A4A1 remained 76% and 95% intact (FIG. 3).

To understand the inhibition mechanism, we also measured the protease kinetics in the presence of various concentrations of inhibitory mAbs.

Discussion

Figure 11:
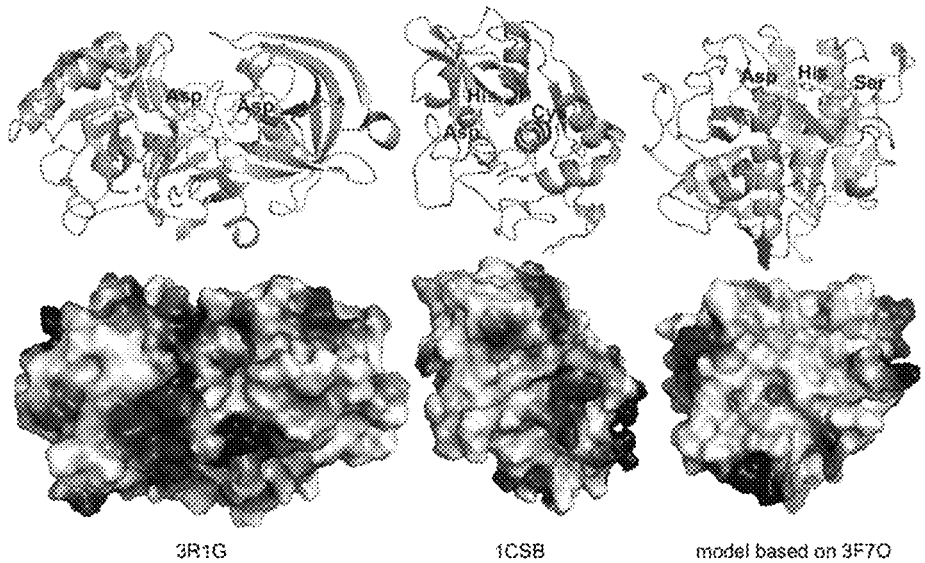
FIG. 11. Active sites and electrostatic surface potentials of representative proteases. Side chains of the catalytic residues are highlighted. Surface topologies display the reactive clefts or cavities of diverse conformation. Images were generated with indicated PDB files by using PyMol.

In this study, we chose four disease-associated proteases having diverse catalytic chemistries and surface topologies. More specifically, while MMPs and cathepsins display well pronounced catalytic clefts and BACE1 shows a large reaction cavity, the active site of Alp2 is relatively small and shallow (FIG. 11). Interestingly, when two synthetic Fab libraries carrying CDR-H3s of 23-27 or 5-21 amino acids were separately applied for BACE1 (Table 2), we were able to isolate inhibitory mAbs from both libraries. Among eight potent anti-BACE1 inhibitors, five of them carry long CDR-H3s (>20 aa), and the remaining three have short CDR-H3s (7-12 aa) (Table 1). However, when these two synthetic Fab libraries were combined and jointly applied for Alp2, the most potent Fab isolated (A4A1 with a $K_I$ of 13 nM) was derived from the short CDR-H3 library. These results suggest that, at least for active site inhibitors, appropriate CDR-H3 length distribution is important to accommodate desired paratope conformations that are compatible with targeted protease topology.

Figure 7:
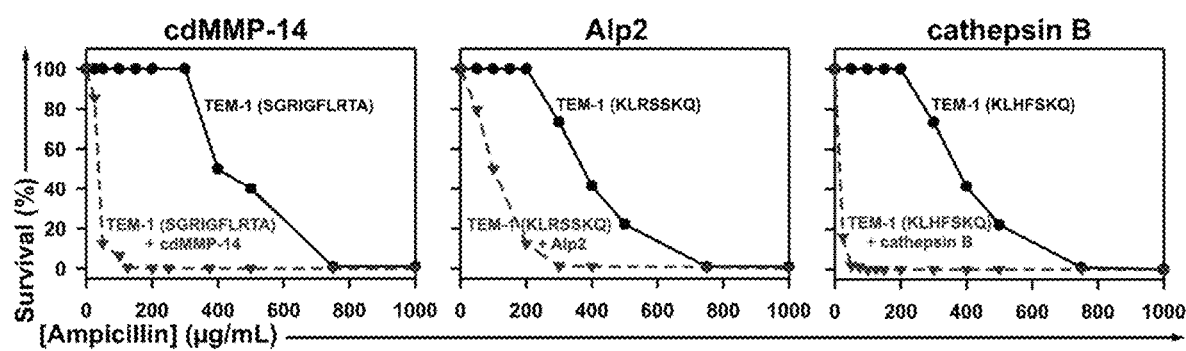
FIG. 7. Selection windows for cdMMP-14, Alp2 and cathepsin B inhibitors. β-lactamase TEM-1 was modified by insertion of the protease specific cleavage peptide sequences (shown in parentheses) between Gly196 and Glu197 of TEM-1. At 0-1000 µg/mL ampicillin, survival curves of $E.$ $coli$ cells transformed with modified TEM-1 were measured (solid), and compared to these for cells co-expressing associated proteases (dashed). For cdMMP-14, the 2×YT agar plates contained 2% glucose. For Alp2 and cathepsin B, the 2×YT agar plates contained 0.1 mM IPTG. Figure discloses "cdMMP-14" sequences as SEQ ID NO: 133, "Alp2" sequences as SEQ ID NO: 136, and "cathepsin B" sequences as SEQ ID NO: 137.

Our functional selection achieved an exceptionally high success rate; however, some "false positive" clones were also identified. We further analyzed these 'false positive' clones, aiming to understand how they could survive during this live or die selection. For example, Two non-inhibitory anti-Alp2 Fabs were isolated with a peptide insertion KLRSSKQ (SEQ ID NO:136), which was derived from a generic substrate of serine proteases. Notably, the survival rates of E. coli cells co-expressing Alp2 and KLRSSKQ (SEQ ID NO:136) inserted TEM-1 only gradually but not sharply decreases when ampicillin concentration increases (FIG. 7 middle panel). This suboptimal survival curve implies the chances for non-inhibitory clones able to escape from the ampicillin selection. Indeed, choosing peptide inserts with fast cleavage kinetics is important for efficient selection of protease inhibitory mAbs.

Other than antibody library and peptide insertion sequence designs, the selection conditions, such as concentrations of ampicillin and inducer, culture media, and temperature, can also be customized for each protease target, allowing rapid downsizing of libraries. Our selection resulted in potent mAbs—more than half of identified inhibitors showed a $K_I$<250 nM. Some isolated inhibitors however had weak potency ($K_I$>1 µM), presumably caused by a high expression level of certain Fabs which compensates their low potency. In addition, our approach of periplasmic co-expression facilitates the disulfide formation required for activities of many human proteases, e.g. catalytic domains of BACE1 and cathepsin B have 3 and 6 disulfide bonds respectively. Furthermore, proteases were produced in their propeptide-free form, thus isolated mAbs can directly inhibit the activated proteases. Certain macromolecular inhibitors of proteases, especially the canonical mechanism inhibitors including endogenous inhibitors and inhibitory mAbs, tend to be slowly cleaved by the targeted protease (Farady C J, Craik C S. (2010) Chembiochem. 11:2341-2346). However, the mAbs isolated in this study exhibited excellent proteolytic stability (FIG. 3). Likely it was benefited from the nature of in vivo selection, because inhibitory function and thus the integrity of Fabs must be maintained over the entire course for cell survival.

In summary, this study described a high-throughput method for selecting protease inhibitory mAbs. Compared to recent technology developments such as epitope synthetic mimicry (Sela-Passwell, et al., Nat Med. 18, 143-147 (2012)), convex paratope design (Nam et al., Proc Natl Acad Sci USA 113, 14970-14975 (2016)), competitive phage elution (Devy et al., *Cancer Res.* 69, 1517-1526 (2009)), cytoplasmic genetic selection (Gal-Tanamy et al., *J Mol Biol.* 347, 991-1003 (2005)), and epitope-specific FACS (Lopez et al., *Biotechnol Bioeng.* 115, 2673-2682 (2018)), this method directly relies on functional inhibition and offers the following advantages: (i) an exceptionally high successful rate as ratio of inhibitors over binders (Table 2); (ii) exclusive selectivity against proteases of the same family (FIG. 2 & FIG. 9); (iii) isolated mAbs are proteolytic stable and cannot be cleaved by targeted proteases (FIG. 3); and (iv) both active-site and allosteric inhibitors can be identified. Overall, the method demonstrated here can be readily applied for the development of inhibitory mAbs targeting a large variety of biomedically important proteases. In addition, since natural inhibitors of proteases are often characterized by broad selectivity, our study can also be used for engineering endogenous inhibitors with improved specificity.

Materials and Methods
Development of Protease Cleavage Reporters

Plasmid carrying β-lactamase TEM-1 gene was PCR amplified to introduce unique XbaI and NcoI recognition sites between G196 and E197 of TEM-1. The PCR product was ligated with 5' phosphorylated oligonucleotide assembled adapters encoding protease specific cleavable peptide sequences (Table 2) flanked by serine-glycine linkers (GSG[peptide]SGG) to obtain modified TEM-1s. Genes encoding extracellular or catalytic domains of human human MMP-14 (residue 114-320), human β-secretase 1 (BACE1, residue 46-457), *Aspergillus fumigatus* autophagic serine protease 2 (Alp2, residue 136-495), and human cathepsin B (residue 66-339) without their associated propeptide sequences were PCR assembled and cloned into SfiI sites on pMopac16 carrying a p15A origin and a pelB leader peptide to obtain their periplasmic expression plasmids (Nam D H, Ge X. *Biotechnol. Bioeng.* 113, 717-723 (2016)). The modified TEM-1 genes were then sub-cloned into these protease expression plasmids using NsiI and NheI sites to generate reporter plasmids (FIG. 1A). All cloned plasmids were confirmed by DNA sequencing. β-lactam ring hydrolysis activities of modified TEM-1s in the absence or presence of associated proteases were assayed by culturing transformed *E. coli* BL21 cells at serial dilutions on 2×YT agar plates containing 34 µg/mL chloramphenicol, 50 µg/mL kanamycin, 0-0.1 mM IPTG, 0-2% glucose, and 0-1000 µg/mL ampicillin at 30° C. for 16 hours. The ratios of colony numbers on ampicillin plates over colony numbers on ampicillin-free plates were calculated as survival rates, which were used to identify the optimal conditions of inhibitor selection for each protease target.

Selection of Protease Inhibitory Antibodies

Fab library genes containing regular length (Persson et al., *J Mol Biol.* 425, 803-811 (2013)) or ultra-long CDR-H3s (Nam D H, Ge X. et al., *Methods Mol Biol.* 1731, 307-324 (2018)) were PCR amplified and cloned into pHPK (kanR, pBR322, phoA promoter, and STII leader peptide). Constructed library plasmids pHPK-Fab were transformed into *E. coli* Jude-I electrocompetent cells for amplification. Randomly picked colonies were sequenced for library quality and diversity tests. Electrocompetent cells of BL21 harboring the reporter plasmid for individual protease were transformed with 100 µg library pHPK-Fab. Transformed cells were cultured on 2×YT agar plates of pre-determined selection conditions specific for each protease (Table 2). Small aliquots of transformed cells were also serially diluted and cultured on 2×YT agar plates supplemented with 34 µg/mL chloramphenicol and 50 µg/mL kanamycin for library size determination. Colonies surviving the initial selection were individually inoculated in the 2×YT selection media with a higher ampicillin concentration for secondary screening. Well-grown clones were selected for Fab plasmid extraction and VH and VL DNA sequencing.

Production of Antibodies and Proteases

Fab expression plasmids of isolated antibodies were transformed into BL21 cells for periplasmic production by culturing in 2×YT media at 30° C. for 12 hours. Fabs with a hexahistidine tag (SEQ ID NO: 140) at the C-terminal of VH were purified using Ni-NTA agarose (Qiagen) from periplasmic fractions prepared by lysozyme and osmotic shock (Rodriguez et al., *Appl Biochem Biotechnol.* 183, 520-529 (2017)). Associated IgGs were produced in HEK293F (ThermoFisher Scientific) as previously described (Chen et al., *Oncotarget.* 9, 29431-29444 (2018)). Purified Fabs and IgGs were dialyzed at 4° C. against the following assay buffers: 50 mM Tris-HCl pH 7.5, 150 mM NaCl, 5 mM $CaCl_2$, 0.1 mM $ZnCl_2$ for cdMMP-14; PBS pH 7.5 for Alp2 and cathepsin B; and 20 mM HEPES, 125 mM NaCl pH 5.0 for BACE1. Dialyzed antibody samples were concentrated by 10 kDa MWCO ultrafiltration (Amicon), and their purity and concentration were determined by SDS-PAGE and UV spectrophotometer (BioTek). C-terminal hexahistidine tagged (SEQ ID NO: 140) cdMMP-9, cdMMP-12, cdMMP-14, Alp2, cathepsin B, and cathepsin K were produced in their active format in the periplasmic space of *E. coli* without refolding or activation (Nam D H, Ge X. *Biotechnol. Bioeng.* 113, 717-723 (2016)) and purified using Ni-NTA agarose (Qiagen). MMP-2 was purchased from AnaSpec Inc. BACE1-Fc fusion was produced by HEK293F using pcDNA-intron-SPL-BACE-Fc-WPRE containing human IgG1 heavy chain with the associated signal peptides and Woodchuck hepatitis virus posttranscriptional regulatory elements to enhance the expression. Cultured media was clarified by centrifugation and 0.45 µm filtration, and BACE1-Fc was purified by protein A affinity chromatography (GenScript).

Biochemical Characterizations of Isolated Antibodies

Binding kinetics of produced antibodies towards associated protease targets were analyzed by using biolayer interferometry (ForteBio). For Fabs, biotinylated proteases were immobilized on streptavidin biosensors, and Fab binding to the sensors in absence of protease was monitored as backgrounds. For IgGs, protein A sensors were used and protease bindings without IgG were checked as backgrounds. $k_{on}$ and $k_{off}$ were determined for $K_D$ calculations. Competitive ELISA of Fabs on immobilized cdMMP-14 in the presence of 1 nM-1 µM nTIMP-2 was also tested. Fab in vitro stability was tested by incubating 1 µM Fab with 1 µM of the respective protease in the assay buffer for 12 hours and the samples were analyzed by SDS-PAGE.

For inhibition tests, 1 µM Fabs were 2-fold serially diluted into protease specific assay buffer and incubated with 1-10 nM proteases for 30 min at room temperature. The kinetic measurements were started with the addition of 1 µM following FRET peptide substrates: M-2350 (Bachem) for MMP-14, M-2420 (Mca-SEVNLDAEFK(Dnp)-OH (SEQ ID NO:141), Bachem) for BACE1, Mca-KLRSSKQK(Dnp) (SEQ ID NO:142) (Biomatik) for Alp2, and M-2595 (Abz-GIVRAK(Dnp)-OH (SEQ ID NO:143), Bachem) for cathepsin B. The generated fluorescence signals were monitored with excitation and emission wavelengths at 325 and 392 nm (except M-2595 at 320/420 nm) using a fluorescence plate reader (BioTek). Inhibition percentages at given concentrations were calculated by comparing the initial reaction rates in the presence or absence of inhibitor. $IC_{50}$ was determined as the concentration that achieved 50% inhibition, and $K_I$ values were calculated using $K_I=IC_{50}/(S/K_m+1)$. $V_{max}$ and $K_m$ at various Fab concentrations were measured to determine the inhibition type. FRET inhibition assays were also used for selectivity tests of isolated Fabs with the relevant proteases.

For amyloid precursor protein (APP) degradation studies, $APP_{571-696}$ was cloned to the C-terminal of maltose binding protein (MBP) for *E. coli* expression and purified using amylose resin (NEB). 5 μM purified MBP-APP was incubated with 1 μM BACE1-Fc in the absence or presence of 1 μM IgG in BACE1 assay buffer at 37° C. for 24 h. In addition, $APP_{571-696}$ was cloned to a pcDNA plasmid carrying a SPE leader for secretion expression. Transfected HEK293F cells were cultured in Expi293 media for 72 hrs with the presence of 14-800 nM purified IgG. The supernatants were clarified by centrifugation and 0.45 μm filtration, and produced $A\beta_{1-40}$ was quantified by ELISA (Abcam). For Alp2, 10 μg/mL FITC-conjugated type I collagen (AnaSpec) was incubated with 2 μM Alp2 in PBS at room temperature in the presence or absence of 10 μM Fab for 18 h. The reaction solution was centrifuged at 3,000 g for 10 min and the fluorescence of the supernatant was measured at Ex/Em=490/520 nm.

Tables

TABLE 1

Isolated inhibitory antibodies toward four classes of proteases.

| Protease Type | Target (indication) | Cleavable Peptide on TEM-1 | Fab | *CDR-H3 (length) | Binding Affinity $K_D$ (nM) | Inhibition Potency $K_I$ (nM)† |
|---|---|---|---|---|---|---|
| Metallo- | MMP-14 (cancer) | SGRIGFLRTA (SEQ ID NO: 133) | 2B4 | SDSAVYSVRRMGSSGLAAYAMDY (23) (SEQ ID NO: 4) | 66 | 98 |
| | | | 2B12 | DCCSCVFSQSAGITLACVYVMDY (23) (SEQ ID NO: 8) | 76 | 120 |
| | | | 1A5 | LDFLMRDIYYDLGGGALGWLIKYAMDY (27) (SEQ ID NO: 12) | 57 | 150 |
| | | | 2B10 | QLFACWRQSILTPPLLSAMMMGYAMDY (27) (SEQ ID NO: 16) | 46 | 210 |
| | | | 2D9 | GVTRFTNDASVGQVWAGAYGMDY (23) (SEQ ID NO: 20) | 260 | 230 |
| | | | 2A6 | VVRMLPVRCIPRCIKTTLPLYGMDY (25) (SEQ ID NO: 24) | 130 | 430 |
| Aspartic | BACE-1 (Alzheimer's) | EISEVKMDAEY (SEQ ID NO: 135) | B3B12 | YICGHRWRDFDMWRARTGVNYAMDY (25) (SEQ ID NO: 32) | 10 (7)‡ | 23 (13)‡ |
| | | | B1A4 | HYYVSVGSGIDY (12) (SEQ ID NO: 40) | 21 (16)‡ | 41 (35)‡ |
| | | | B2B5 | WHGYPPGYSYYSSFSSSGFDY (21) (SEQ ID NO: 43) | 130 | 77 |
| | | | B2B2 | YWGYYAWFGSHPWAYGAFDY (20) (SEQ ID NO: 49) | 52 | 87 |
| | | | B2B3 | SASGIDY (7) (SEQ ID NO: 52) | 100 | 100 |
| | | | B2B9 | SSSSYYYGMDY (11) (SEQ ID NO: 56) | 110 | 120 |
| | | | B2B6 | DNSICVLTQKEVDTKFLVGQHSYVMDY (27) (SEQ ID NO: 60) | 28 | 130 |
| | | | B1B3 | ERSSCPVGWRDSRFGADGYGLEY (23) (SEQ ID NO: 64) | 31 | 210 |
| Serine | Alp2 (aspergillosis) | KLRSSKQ (SEQ ID NO: 136) | A4A1 | FGSWSYAIDY (10) (SEQ ID NO: 68) | 11 | 13 |
| | | | A4A2 | KTSDQYLLVGGSFFKLRDCCYVMDY (25) (SEQ ID NO: 72) | 110 | 220 |
| | | | A4A7 | GRSPGPYAVCGNLFRSVSYGMDY (23) (SEQ ID NO: 76) | 420 | 300 |
| Cysteine | cathepsin B (cancer) | KLHFSKQ (SEQ ID NO: 137) | CBA3 | GFAWSPGLDY (10) (SEQ ID NO: 80) | 16 | 91 |
| | | | CBA2 | YGYPGGYHFWGWWSSPYAFDY (21) (SEQ ID NO: 84) | 190 | 130 |
| | | | CBA1 | GGGSWSAMDY (10) (SEQ ID NO: 87) | 290 | 200 |

Note:
*Only Fabs (with inhibition constants $K_I$s) <500 nM are shown.
†For each protease target, clones are ranked by their $K_I$ values.
‡Data of associated IgGs are shown in parentheses.

TABLE 2

Conditions and statistics of selections for protease inhibitory antibodies

| Protease | cdMMP-14 | BACE1 | Alp2 | cathepsin B |
|---|---|---|---|---|
| Peptide insert | SGRIGFLRTA (SEQ ID NO: 133) | EISEVKMDAEY (SEQ ID NO: 135) | KLRSSKQ (SEQ ID NO: 136) | KLHFSKQ (SEQ ID NO: 137) |

TABLE 2 -continued

Conditions and statistics of selections for protease inhibitory antibodies

| Protease | cdMMP-14 | BACE1 | | Alp2 | cathepsin B |
|---|---|---|---|---|---|
| Library | | | | | |
| CDR-H3 length (aa) | 23, 25, 27 | 23, 25, 27 | 5-21 | 5-21, 23, 25, 27 | 5-21 |
| Size | 8.6 x 10$^8$ | 7.1 x 10$^8$ | 1.8 x 10$^8$ | 2.9 x 10$^8$* | 1.5 x 10$^8$ |
| Initial selection | | | | | |
| [Amp] (µg/mL) | 200 | 300 | 300 | 300 | 300 |
| [IPTG] (mM) | 0 | 0.1 | 0.1 | 0.1 | 0.1 |
| [glucose] (%) | 2 | 0 | 0 | 0 | 0 |
| Temp (° C.) | 30 | 30 | 30 | 30 | 30 |
| #of clones remaining | 190 | 24 | 87 | 43 | 122 |
| Secondary screening | | | | | |
| [Amp] (µg/mL) | 300 | 400 | 400 | 500 | 400 |
| [IPTG] (mM) | 0 | 0.1 | 0.1 | 0.1 | 0.1 |
| [glucose] (%) | 0 | 0 | 0 | 0 | 0 |
| Temp (° C.) | 30 | 30 | 30 | 30 | 30 |
| # of clones remaining | 161 | 21 | 52 | 29 | 7† |
| Sequenced | 40 | 8 | 5 | 10 | 7 |
| Unique correct sequences | 38 | 6 | 5 | 8 | 5 |
| Fabs produced | 6 | 6 | 5 | 8 | 3 |
| Binders | 6 | 6 | 5 | 8 | 3 |
| Inhibitors | 6 | 6 | 5 | 6 | 3 |

Note:
*Long CDR library (CDR-H3 length = 23, 25 or 27) and normal CDR library (CDR-H3 length = 5-21) were combined for selection.
†Only 10 clones were randomly picked for secondary screening.

Example 2. Generation of Highly Selective Monoclonal Antibodies Inhibiting a Recalcitrant Protease Using Decoy Designs Matrix metalloproteinase-12 (MMP-12), also known as macrophage elastase, is a potent inflammatory mediator and therefore an important pharmacological target. Clinical trial failures of broad-spectrum compound MMP inhibitors suggested that specificity is the key for a successful therapy. To provide the required selectivity, monoclonal antibody (mAb)-based inhibitors are on the rise. However, poor production of active recombinant human MMP-12 catalytic domain (cdMM4P-12) presented a technical hurdle for its inhibitory mAb development. We hypothesized that this problem could be solved by designing an expression optimized cdMMP-12 mutant without structural disruptions at its reaction cleft and the surrounding vicinity, and thus isolated active-site inhibitory mAbs could maintain their binding and inhibition functions toward wild type MMP-12. We combined three advances in the field—PROSS algorithm for cdMMP-12 mutant design, convex paratope antibody library construction, and functional selection for inhibitory mAbs. As the results, isolated Fab inhibitors showed nanomolar affinity and potency toward cdMMP-12 with high selectivity and decent proteolytic stability. Particularly, Fab LH11 targeted the reaction cleft of wild type cdMMP-12 with 75 nM binding K$_D$ and 23 nM inhibition IC$_{50}$. We expect that our methods can promote the development of mAbs inhibiting important proteases, many of whom are recalcitrant to functional production.

Introduction

As key cellular proteinases, matrix metalloproteinases (MMPs) are zinc-dependent endopeptidases that hydrolyze parts of the extracellular matrix (Visse, R., & Nagase, H. (2003). Circ Res, 92(8), 827-839). MMPs play a key role in a variety of biological processes (Amar, S., Smith, L., & Fields, G. B. (2017). Biochim Biophys Acta Mol Cell Res, 1864(11 Pt A), 1940-1951; Malemud, C. J. (2006). Front Biosci, 11, 1696-1701), and thus are promising therapeutic targets in many-sided pathologies (Deu, et al., (2012). Nat Struct Mol Biol, 19(1), 9-16; Drag, M., & Salvesen, G. S. (2010). Nat Rev Drug Discov, 9(9), 690-701; Li, et al., (2020). Pharmacol Ther, 207, 107465). Among MMPs, MMP-12 is mainly expressed in macrophages (Visse, R., & Nagase, H. (2003). Circ Res, 92(8), 827-839) and is required for macrophage-mediated extracellular matrix proteolysis and tissue invasion (Shipley, et al., (1996). Proc Natl Acad Sci USA, 93(9), 3942-3946). MMP-12 is different from other MMPs in its ability to cleave hydrolysis resistant fibrils such as elastin and collagen within its catalytic domain (Nagase, H. (2001). In N. J. Clendeninn & K. Appelt (Eds.), Matrix Metalloproteinase Inhibitors in Cancer Therapy (pp. 39-66). Totowa, N.J.: Humana Press; Van Doren, S. R. (2015). Matrix Biol, 44-46, 224-231). Furthermore, MMP-12 is secreted by macrophages at sites of inflammation (Lagente, et al., (2009). Expert Opin Ther Targets, 13(3), 287-295), and the abnormal expression of MMP-12 leads to tissue damage that contributes to coronary artery and cerebral vascular disease (Liu, et al., (2015). Sci Rep, 5, 17189), metastatic cancer (Shipley, et al., (1996). *Proc Natl Acad Sci US A,* 93(9), 3942-3946), and a variety of other diseases such as pulmonary disease (Molet, et al., (2005). *Inflamm Res,* 54(1), 31-36), psoriatic disease (Mezentsev, et al., (2014). *Gene,* 540(1), 1-10), and inflammatory and rheumatoid arthritis (Liu, et al., (2004). *Arthritis Rheum,* 50(10), 3112-3117), making MMP-12 a key regulatory enzyme for disease progression. Therefore, there is a considerable interest in the development of MMP-12 inhibitors for the treatment of MMP-12 related diseases.

Numerous studies have been conducted to identify the roles of MMP-12, especially to focus on development of inhibitors (Chelluboina, et al., (2018). *Mol Neurobiol,* 55(2), 1405-1409). Broad-spectrum MMP small molecule inhibitors (most frequently, active-site zinc-chelating hydroxamates) have been tested in clinical trials in the past but all have failed due to their low overall efficacy and side effects caused by poor selectivity (Turk, B. (2006). *Nat Rev Drug Discov,* 5(9), 785-799). This is mainly due to the active site and catalytic mechanism are highly conserved among MMPs. Developing MMPs inhibitors requires selective inhibition of the target MMP without cross reactivity toward other MMPs (Decock, et al., (2011). *J Cell Mol Med,* 15(6), 1254-1265). Because monoclonal antibodies (mAbs) usually render exquisite specificity, long half-life in serum, and low immunogenicity, mAbs have emerged as a promising alternative for selective MMP inhibition (Devy, et al., (2009). *Cancer Res,* 69(4), 1517-1526; Ling, et al., (2017). *Oncotarget,* 8(35), 58372-58385; Lopez, et al., (2019). *Proc Natl Acad Sci USA,* 116(33), 16314-16319; Naito, et al., (2012). *Biochemistry,* 51(44), 8877-8884; Razai, et al., (2020). *J Biol Chem,* 295(8), 2464-2472; Sandborn, et al., (2016). *Aliment Pharmacol Ther,* 44(2), 157-169; Sela-Passwell, et al., (2011). *Nat Med,* 18(1), 143-147). So far, few small molecule inhibitors highly selective for MMP-12 have been described (Devel, et al., (2006). *J Biol Chem,* 281(16), 11152-11160; Nuti, et al., (2018). *J Med Chem,* 61(10), 4421-4435), and thus developing its inhibitory mAbs is important for fundamental research and therapeutic development.

Figure 12:
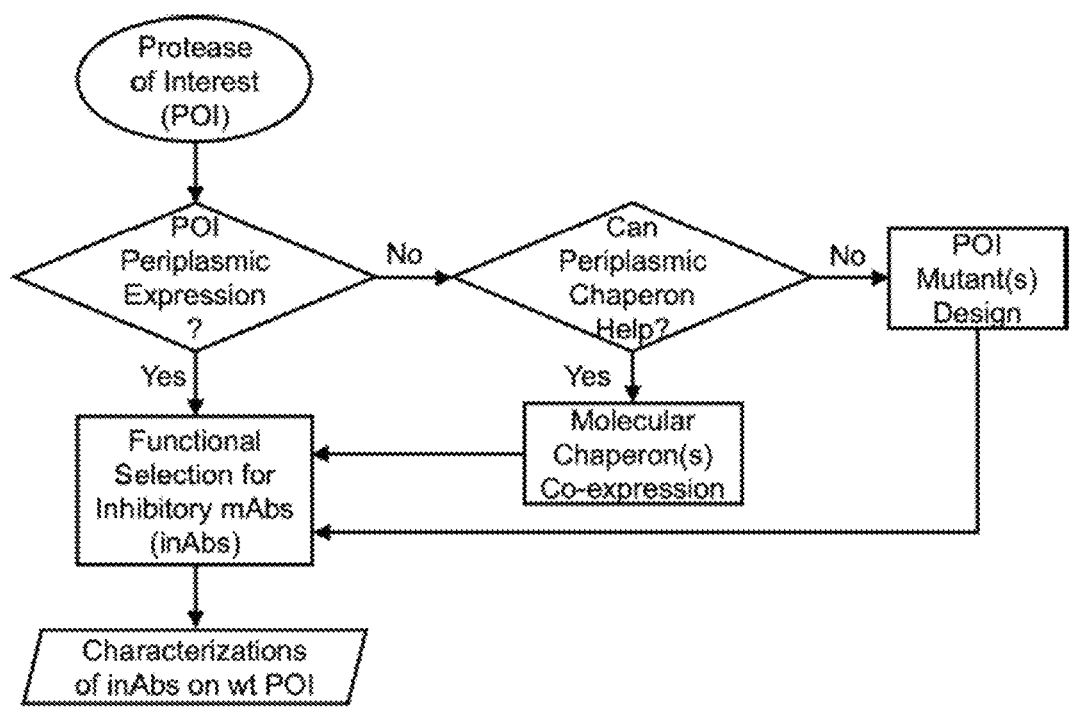
FIG. 12. Strategy for inhibitory mAbs targeting difficult proteases.

To facilitate protease inhibitory mAb discovery, our previous works developed convex paratope antibody libraries and a functional selection method (Lopez, et al., (2019). *Proc Natl Acad Sci USA,* 116(33), 16314-16319; Nam, et al., (2016). *Proc Natl Acad Sci USA,* 113(52), 14970-14975, which are incorporated by reference herein in their entirety). In this selection, a protease of interest, an antibody Fab library, and a modified β-lactamase as a reporter are co-expressed in the periplasm of *Escherichia coli*. Initial attempts to directly apply this method for the development of mAbs inhibiting MMP-12, however, indicated that periplasmically produced MMP-12 catalytic domain (cdMMP-12) was inactive (Table 5 and FIG. 20). To solve this issue, we hypothesized that (a) an active cdMMP-12 mutant with no configuration change at its reaction cleft and surrounding vicinity could serve as a decoy for the discovery of active-site mAb inhibitors, and (b) thus isolated inhibitory mAbs could maintain their binding affinity and inhibition potency toward cdMMP-12 wild type (FIG. 12). We expected that cdMMP-12 mutants with improved functional expression can be designed by using PROSS, an automated algorithm successfully predicted mutations of numerous proteins with enhanced stability and/or higher yields in *E. coli* (Campeotto, et al., (2017). *Proc Natl Acad Sci USA,* 114(5), 998-1002; Goldenzweig, et al., (2016). *Mol Cell,* 63(2), 337-346). In this study, PROSS designs of cdMMP-12 variants were structure-validated, and their periplasmic expression was optimized. Applying the functional selection (Lopez, et al., (2019). *Proc Natl Acad Sci USA,* 116(33), 16314-16319), inhibitory mAb clones were then isolated from human Fab synthetic libraries carrying convex paratopes (Nam, et al., (2016). *Proc Natl Acad Sci USA,* 113(52), 14970-14975). Finally, discovered Fabs were produced and characterized toward both the mutant design and wild type of cdMMP-12.

Materials and Methods

Cloning, expression and periplasmic FRET assays of cdMMP-12 wt and mutants Structure of human MMP-12 catalytic domain 2OXU was used in PROSS algorithm with default settings for mutation design (Goldenzweig, et al., (2016). *Mol Cell,* 63(2), 337-346). The genes encoding cdMMP-12 wt and mutants D1/D4/D7 (FIG. 12) were chemically synthesized with codons optimized for *E. coli* expression. After PCR amplification, the fragments were cloned into SfiI sites on pMoPac16, a periplasmic expression vector carrying Plac promoter and pelB leader. Obtained plasmids were transformed to *E. coli* BL21 competent cells, and cells were cultured in 2×YT/Chlor media supplemented with or without 0.1 mM IPTG. After overnight culture at 30° C. or room temperature, 0.8 $OD_{600}$ cells were harvested by centrifugation and resuspended in 50 μL 200 mM Tris-HCl pH 7.5, 20% sucrose, and 30 U/L lysozyme for 10 min incubation at room temperature. The samples were then treated by osmotic shock with 50 μL ice-cold $ddH_2O$ and incubated on ice for 10 min. After centrifugation at 15,000×g for 2 min, cleared periplasmic fractions were transferred to 96-well assay plates (Corning). In FRET assays, 1 μM MMP substrate M-2350 (Bachem) was added to periplasmic preparations to start the reactions at 37° C. The fluorescent signals (RFU) with excitation at 328 nm and emission at 393 nm were monitored using a Synergy H4 microplate reader (BioTek).

Construction of reporter plasmid and Fab selection Oligonucleotides encoding cleavable peptide sequence PLGLEEAK (SEQ ID NO:134) and its flanking linkers were synthesized and inserted between Gly196 and Glu197 of β-lactamase TEM-1 gene by overlap extension PCR. Obtained expression cassette of modified TEM-1 was cloned into NsiI/NheI sites on pMoPac16 to give pm12TEM. The gene of cdMMP-12 mutant D4 was then cloned into SfiI sites on pm12TEM to give pm12TEM-cd12D4. *E. coli* BL21 cells transformed with pm12TEM or pm12TEM-cd12D4 were serially diluted and cultured at 30° C. for 16 h on 2×YT agar plates containing 34 μg/mL chloramphenicol and 0, 31, 63, 100, 125, 250, 450, 500, 750 or 1000 μg/mL ampicillin to determine the selection window. BL21 harboring unmodified TEM-1 was used as control. 10 g Fab library plasmids pHPK-Fab carrying long CDR-H3s (Lopez, et al., (2019). *Proc Natl Acad Sci USA,* 116(33), 16314-16319) were transformed to 500 $OD_{600}$ electrocompetent cells of *E. coli* BL21 harboring the reporter plasmid pm12TEM-cd12D4. Library size was determined by growing serially diluted transforms on 2×YT/Kan agar plates. In initial selection, the Fab library cells were grown at 30° C. for 16 h on 2×YT agar plates supplemented with 34 μg/mL chloramphenicol, 50 μg/mL kanamycin, and 500 μg/mL ampicillin. Surviving colonies were then individually screened by culturing in 2×YT media containing 700 μg/mL ampicillin at 30° C. Clones survived the second screening were recovered for plasmid extraction and VH DNA sequencing.

Protein expression and purification Expression plasmids of isolated Fab clones were transformed to BL21 and cells were cultured in 600 mL 2×YT/Kan at 30° C. overnight.

Periplasmic fractions were prepared, and Fabs with a hexahistidine tag (SEQ ID NO:140) at the C-terminal of $C_H1$ were purified using Ni-NTA agarose (Qiagen), and dialyzed in 50 mM HEPES, 150 mM NaCl pH 7.5 overnight to eliminate residual imidazole. After purity was confirmed by SDS-PAGE, Fab concentrations were determined by Nano-Drop (Thermo), and 20% glycerol was used for their storage at −80° C. The genes of cdMMP-12 wt and D4 with a hexahistidine tag (SEQ ID NO:140) at their C-termini were cloned into NdeI/XhoI sites of pET32b and transformed to E. coli BL21. Cells were grown in LB/Amp at 37° C., and 0.1 mM IPTG was added when $OD_{600}$ reached 0.6 for induction at 30° C. for 16 h. Harvested cells were resuspended in 50 mM Tris-HCl (pH 8.0) 100 mg/mL lysozyme and 0.1% Triton X-100 and incubation at room temperature for 15 min. Cell samples were lysed by sonication and centrifuged by 10,000×g for 30 min at 4° C. cdMMP-12 D4 in the recovered supernatant was purified by Ni-NTA agarose and cdMMP-12 wt was refolded and purified from inclusion body (Nam, D. H., & Ge, X. (2016). Biotechnol Bioeng, 113(4), 717-723). The cdMMP-9/-14 and N-terminal domain of tissue inhibitor of metalloproteinases (nTIMPs) were periplasmically expressed and purified as reported (Lee, et al., (2017). Microb Cell Fact, 16(1), 73; Nam, D. H., & Ge, X. (2016). Biotechnol Bioeng, 113(4), 717-723). Concentrations of active MMPs and nTIMPs were titrated with GM6001 (EMD). Gene encoding modified TEM-1 was PCR amplified with N-terminal HA and C-terminal hexahistidine tags (SEQ ID NO:140) and cloned into SfI sites of pMoPac16. The modified TEM-1 was produced and purified from periplasmic expression using E. coli BL21 as mentioned above. Purity of all produced was confirmed by 15% non-reducing SDS-PAGE. Human MMP-1/-7 were purchased from AnaSpec.

ELISA and binding kinetics measurement Purified cdMMP-9, cdMMP-12 D4/wt, and cdMMP-14 were biotinylated by using EZ-Link Sulfo-NHS-LC kit (Thermo Fisher). On streptavidin coated ELISA plates, 5 µg/mL biotinylated cdMMPs were immobilized and incubated with two-fold serially diluted purified Fabs. Bound Fabs were detected with anti-Fab-HRP (Sigma-Aldrich), and signals were developed by TMB substrate (Thermo Scientific) and measured using a microplate reader (BioTek). In competitive ELISA, 500 nM Fabs of interest were mixed with 0.01-10 µM GM6001 or 0.8-200 µM nTIMP-2 for 30 min, then transferred to ELISA plates coated with cdMMP-12 D4/wt for incubation 15 min at room temperature. Bound Fabs were detected using anti-Fab-HRP. For bio-layer interferometry (using ForteBio BLItz), biotinylated cdMMP-12 D4/wt was loaded onto streptavidin biosensors. After washing to establish baselines, 50, 100, or 200 nM of Fabs were associated with immobilized cdMMP-12 D4/wt for 200 sec, then dissociated into 50 mM HEPES, 150 mM NaCl pH 7.5 for 120 sec. Averages of measured $k_{on}$ and $k_{off}$ values were determined for $K_D$ calculations.

FRET peptide inhibition assays In 96-well assay plates (Corning), 60/250/350/10/10/30 nM of (cd)MMP-1/-7/-9/-12 D4/-12 wt/-14 were preincubated with 1 nM-1 µM purified Fabs for 30 min at room temperature then 1 µM substrate M-2350 (Bachem) was added. Generated fluorescent signals ($\lambda_{Ex}$=328 nm, $\lambda_{Em}$=393 nm) were monitored at 37° C. to measure the initial velocities. To calculate inhibition constants ($K_I$s), data were fit with the equations for slow tight-binding inhibitors. The inhibition type of the Fabs was determined using the initial velocities of cdMMP-12 D4 as a function of substrate concentration (250-2000 nM) at various Fab concentrations (31-500 nM). The values of $V_{max}$ and $K_m$ were derived from linearization in accordance with the Lineweaver-Burk equation.

Inhibition tests with macromolecular substrates 10 µg/mL FITC-conjugated elastin (AnaSpec) was incubated with 7 nM cdMMP-12 D4/wt and 2-2000 nM purified Fab in 50 mM Tris-HCl, 150 mM NaCl, 5 mM $CaCl_2$), 100 µM $ZnCl_2$ pH 7.5. Generated fluorescent signals were measured at 12 h with $\lambda Ex$ of 490 nm and $\lambda_{Em}$ of 520 nm. For inhibition assays on fibronectin, 200 nM fibronectin (Corning) was incubated with 200-350 nM cdMMP-12 wt and 2 µM GM6001 or 0.1-6 µM Fabs in 50 mM HEPES, 150 mM NaCl pH 7.5 at 37° C. for 2-4 h. The samples were separated on 5% non-reducing SDS-PAGE and analyzed by western blotting with anti-Fibronectin antibody (Abcam) and chemiluminescent substrate (Thermo Scientific). For inhibition assays on modified TEM-1 carrying cleavable sequence (PLGLEEAK (SEQ ID NO:134)) and a N-terminal HA tag, 250 nM modified TEM-1 was incubated with 700 nM cdMMP-12 wt and 10 µM Fabs in 50 mM HEPES, 150 mM NaCl pH 7.5 at 37° C. for 4 h. The samples were separated on 12% non-reducing SDS-PAGE, and the modified TEM-1 was visualized by western blotting using anti-HA antibody (Invitrogen) and chemiluminescent substrate. Assays without cdMMP-12s or Fabs were performed as controls.

Proteolytic stability tests 2 µM purified Fabs were incubated with 2 µM cdMMP-12 wt/D4 in 50 mM HEPES, 150 mM NaCl pH 7.5 at 37° C. for 4 h. Samples were analyzed by using 12% non-reducing SDS-PAGE and stained with Coomassie blue. Densitometric interpretation was conducted using a ChemiDoc imager (Bio-Rad).

Results cdMMP-12 Mutants Design

Figures 13A, 13B:
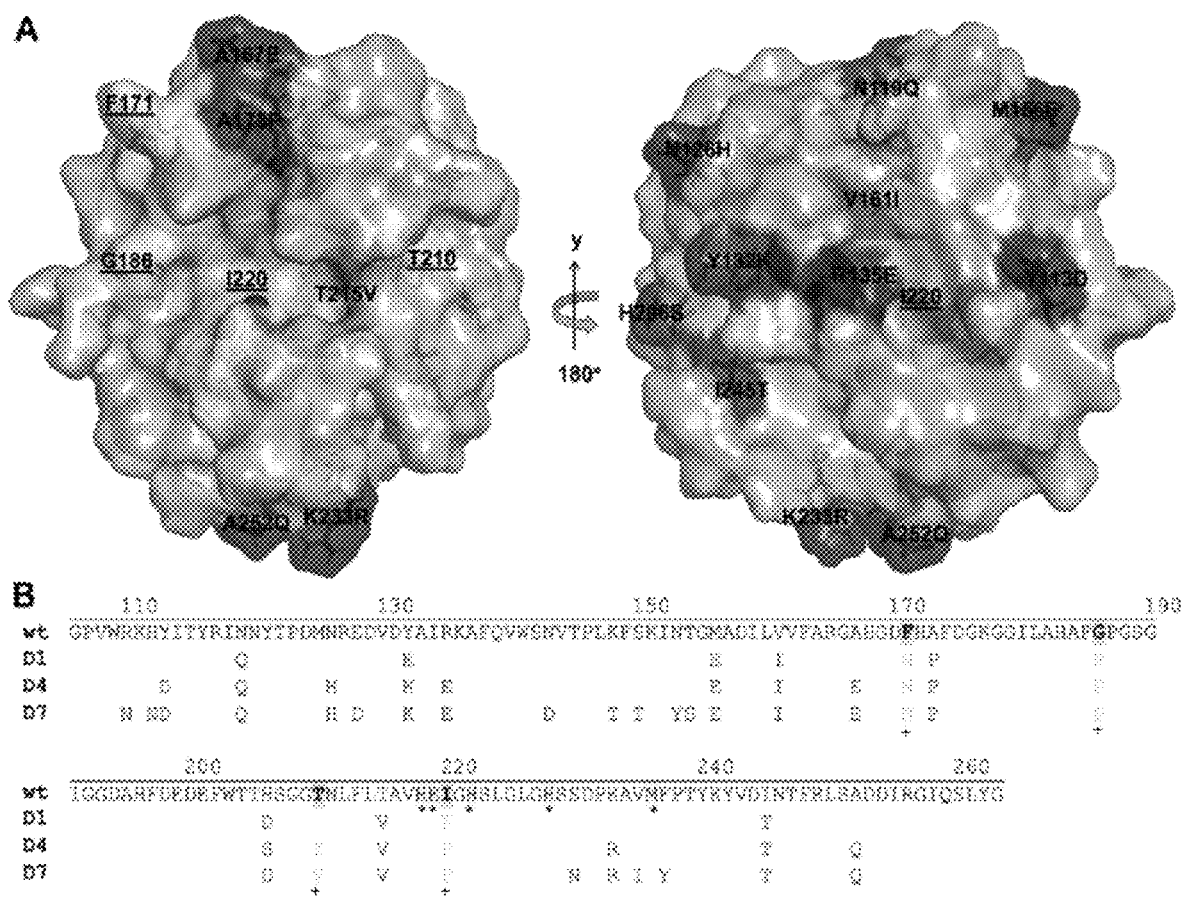
FIGS. 13A-13B. cdMMP-12 mutant design.

To enhance periplasmic expression of soluble and active cdMMP-12, PROSS algorithm was utilized for cdMMP-12 mutant design (Goldenzweig, et al., (2016). Mol Cell, 63(2), 337-346). Applying the default computational settings and X-ray crystallographic structure of human cdMMP-12 as input (PDB=2OXU, resolution=1.24 Å) (Bertini, et al. (2006). Angew Chem Int Ed Engl, 45(47), 7952-7955), the seven obtained variant designs carried 11-29 mutations, representing a mutation rate of 7-18%. In addition to the most constrained and the most permissive designs (D1 and D7), we also chose D4 with 18 mutations (11%) for investigation (FIGS. 13A-13B). PyMOL visualization indicated that majority of these mutations were on surface (e.g. 15 mutations in D4 are solvent exposing), leading to increased surface polarity (e.g. Y113D, Y132K, M156E, A167E, and A252Q in D4), while a small fraction of mutants were buried (e.g. V161I, T215V, and I220F in D4), likely to improve the core packing. In addition, mutations to proline on loops for improving the backbone rigidity were also observed (e.g. A173P and G186P in D4) (FIG. 13A).

As our purpose of designing expression-optimized cdMMP-12 mutants was to facilitate the isolation of mAbs able to inhibit wild type cdMMP-12, any epitope conformational changes at or around the reaction cleft should be minimized. Furthermore, MMP-12 characteristic subsites should remain unaltered. The crystal structure of cdMMP-12 revealed that its reaction cleft, like those of other MMPs, was centered on the active-site helix hB (Lang, et al., (2001) *J Mol Biol,* 312(4), 731-742), which harbored the catalytic Glu219 and the first (His 218) and the second His (His222) to coordinate the catalytic zinc. In the original PROSS designs, Ile220, located in the middle of hB, was mutated to Phe. Although its side chain faced inside, such substitution may introduce undesired conformational changes to the backbone of the reaction cleft. Therefore, Ile220 was kept as the wild type. Docking MMP-12 inhibitor/substrate to its active-site cleft suggested that the subsites of MMP-12 and thus its substrate specificity was partially shaped by the side chains of Phe171 (Lang, et al., (2001) *J Mol Biol*, 312(4), 731-742). Because Phe171 formed a protruded and MMP-12 specific molecular surface, mutations at this position should be avoided. PROSS designs also included mutations at G186 and T210, which sit on the bottom of active cleft at the left (non-primed) and the right (primed) side of the catalytic zinc respectively (FIG. 13A). To minimize the disruption of MMP-12 subsites, mutations on G186 and T210 were rejected from design as well. Collectively, the modified D1/D4/D7 designs had 8/14/25 mutations respectively, all located distally to the active-site cleft.

Periplasmic Production of Active cdMMP-12 Mutant

Figure 20:
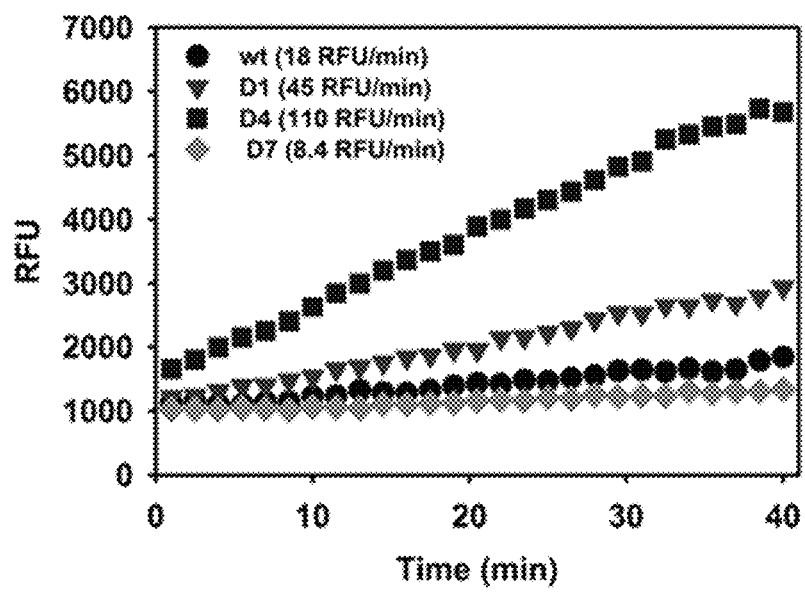
FIG. 20. Enzymatic activities of cdMMP-12 wt and mutants. cdMMP12s were expressed at their optimized expression conditions as shown in Table 5. 0.8 $OD_{600}$ cells were used for periplasmic preparation and MMP-12 activities were measured without purification by using 1 µM FRET peptide. Periplasmic preparation of host cells without carrying cdMM-12 gene had no detectable signals (data not shown).

Structure-validated D1/D4/D7 designs were cloned downstream of a pLac promoter and a pelB leader for expression optimization in *E. coli* BL21. Periplasmic FRET assays indicated that under all tested conditions (RT/30° C., +/−0.1 mM IPTG), neither cdMMP-12 wt nor D7 exhibited significant catalytic functions (Table 5). In contrast, periplasmically expressed D1 and D4 efficiently hydrolyzed an MMP broad-spectrum FRET substrate (M-2350). Furthermore, cultured at 30° C. without IPTG, D4 showed the highest specific activity (110 ΔRFU/min) which was 2.4- to 13-fold faster than the best results of cdMMP-12 wt/D1/D7 (FIG. 20). Therefore, modified D4 was chosen as the cdMMP-12 decoy for mAb selection. D4 was also cytoplasmically expressed and purified with a typical yield of 1.5 mg per liter culture. Enzymatic kinetics assays of purified D4 with M-2350 indicated a $k_{cat}$ of 4.1/sec and a $K_m$ of 8.8 µM.

Feasibility of Functional Selection for cdMMP-12 D4 Inhibitors

Figures 14A, 14B:
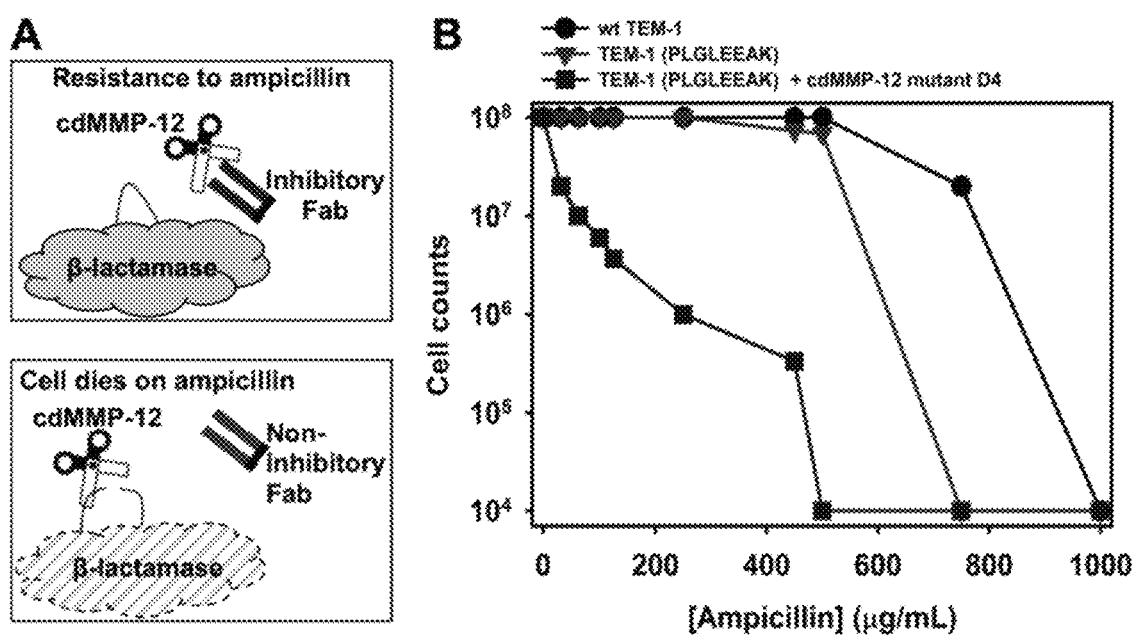
FIGS. 14A-14B. Functional selection for Fabs inhibiting cdMMP-12 D4.

In the selection (Lopez, et al., (2019). *Proc Natl Acad Sci USA*, 116(33), 16314-16319), β-lactamase TEM-1 is modified by insertion of a MMP-12 substrate sequence. In the presence of a D4 inhibitor, TEM-1 will not be cleaved by D4 and thus the cell can survive in ampicillin media. However, in the absence of a D4 inhibitor, modified TEM-1 will be cleaved and leads cell death with ampicillin (FIG. 14A). To utilize this live-or-die selection approach, a peptide substrate PLGLEEAK (SEQ ID NO:134) of fast kinetics ($k_{cat}/K_m$=10 mM$^{-1}$s$^{-1}$, (Lamort, et al., (2016). *Biol Chem*, 397(5), 469-484)) was chosen for TEM-1 modification. DNA fragment encoding this peptide sequence together with its flanking linkers (GSG-PLGLEEAK-SGG (SEQ ID NO:139)) was synthesized and cloned between Gly196 and Glu197 of TEM-1, a site successfully applied for construction of TEM-1 based probes (Galarneau, et al., (2002). *Nat Biotechnol*, 20(6), 619-622; Porter, et al., (2007). *Anal Chem*, 79(17), 6702-6708; Saunders, et al., (2016). *Nat Chem Biol*, 12(2), 94-101). Under the optimized condition for D4 periplasmic expression, $10^8$ CFU of *E. coli* cells transformed with wt TEM-1 or TEM-1 (PLGLEEAK (SEQ ID NO:134)) were cultured on agar plates supplemented with 0-1000 µg/mL ampicillin. Results indicated that below 500 µg/mL ampicillin, survival rates had no significant difference between cells carrying wt TEM-1 and TEM-1 (PLGLEEAK (SEQ ID NO:134)) (FIG. 14B), suggesting that the modified TEM-1 maintained its catalytic function in periplasm. However, when D4 was periplasmically co-expressed with TEM-1 (PLGLEEAK (SEQ ID NO:134)), cell counts dramatically dropped with increasing ampicillin concentration, e.g. $3.7 \times 10^6$ at 125 nM, $1.0 \times 10^6$ at 250 nM, and $1.0 \times 10^4$ at 500 nM. The vast disparity of survival rates with or without D4 co-expression implied that TEM-1 (PLGLEEAK (SEQ ID NO:134)) was indeed cleaved by D4 and thus lost its antibiotic resistance activity. And 500 µg/mL was decided as the ampicillin concentration to be used in the functional selection.

Isolation of Fabs Inhibiting cdMMP-12 D4

Our study (Nam, et al., (2016). *Proc Natl Acad Sci USA*, 113(52), 14970-14975), among others (De Genst, et al., (2006). *Proc Natl Acad Sci USA*, 103(12), 4586-4591; Desmyter, et al., (1996). *Nat Struct Biol*, 3(9), 803-811; Farady, et al., (2008). *J Mol Biol*, 380(2), 351-360; Lauwereys, et al., (1998). *Embo j*, 17(13), 3512-3520; Schneider, et al., (2012). *J Mol Biol*, 415(4), 699-715), suggested that convex paratopes, often formed by extended CDR loops, could favor enzyme inhibition by direct recognition of the reactive cavity. Aiming to generate inhibitory mAbs binding to the reaction cleft conformation shared between D4 and wt cdMMP-14, a synthetic human Fab library ($1.1 \times 10^9$ diversity) carrying CDR-H3s of 23-27 residues was utilized in this study (Lopez, et al., (2019). *Proc Natl Acad Sci USA*, 116(33), 16314-16319). Transformation of the Fab library plasmids to *E. coli* BL12 competent cells harboring both D4 and TEM-1 (PLGLEEAK (SEQ ID NO:134)) resulted in $3.3 \times 10^8$ colonies. After initial selection with 500 µg/mL ampicillin at 30° C. on 2×YT/Kan/Cm agar without IPTG for 16 h, ~1500 clones survived (Table 6). Among them, 700 clones were randomly picked for the secondary screening in 2×YT/Kan/Cm liquid media supplemented with 700 µg/mL ampicillin at 30° C. for 16 h. Among the 100 clones that survived, 16 were picked for DNA sequencing and 13 unique Fab clones were identified. These Fabs were produced in periplasmic fractions of *E. coli* with yields of 0.5-2 mg purified Fabs per liter of culture. Initial inhibition assays with D4 and FRET peptide M-2350 showed a broad range of potency from 75 nM to >1 µM. Out of the seven identified nanomolar range inhibitors (Table 3), Fabs LH11, LG4 and LH6 exhibited the strongest potency and thus were chosen for further characterizations.

Isolated Fabs Bind at Reaction Cleft of cdMMP-12

Figures 15A, 15B:
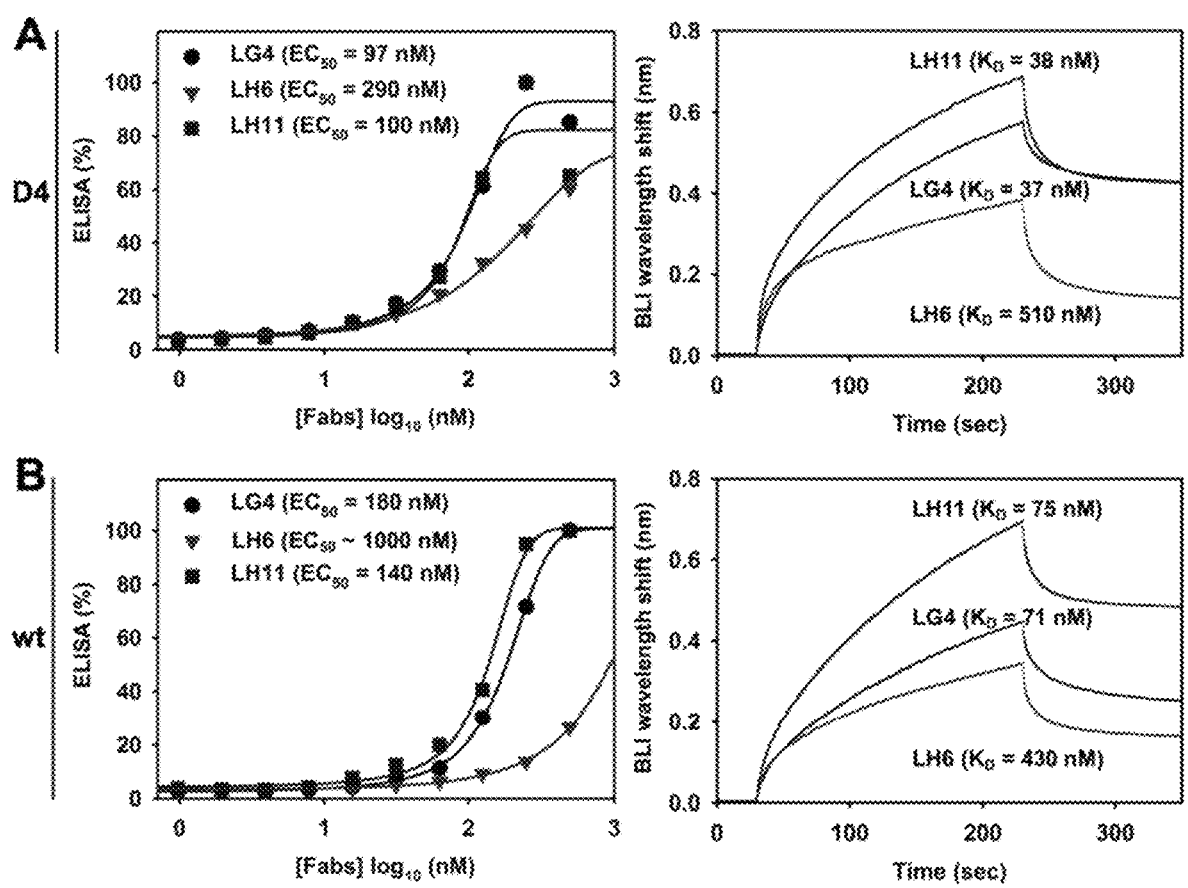
FIGS. 15A-15B. Binding affinities of Fabs LG4, LH6, and LH11 towards (FIG. 15A) cdMMP-12 D4 and (FIG. 15B) cdMMP-12 wt. (Left) Binding $EC_{50}$s and (right) binding kinetics were measured by ELISA and bio-layer interferometry (BLI) respectively. Dissociation constants (KDS) were calculated with BLI data collected using 50, 100, and 200 nM Fabs. Representative BLI results of 100 nM Fabs are shown and full data sets are available in FIGS. 21A-21B.
Figures 21A, 21B:
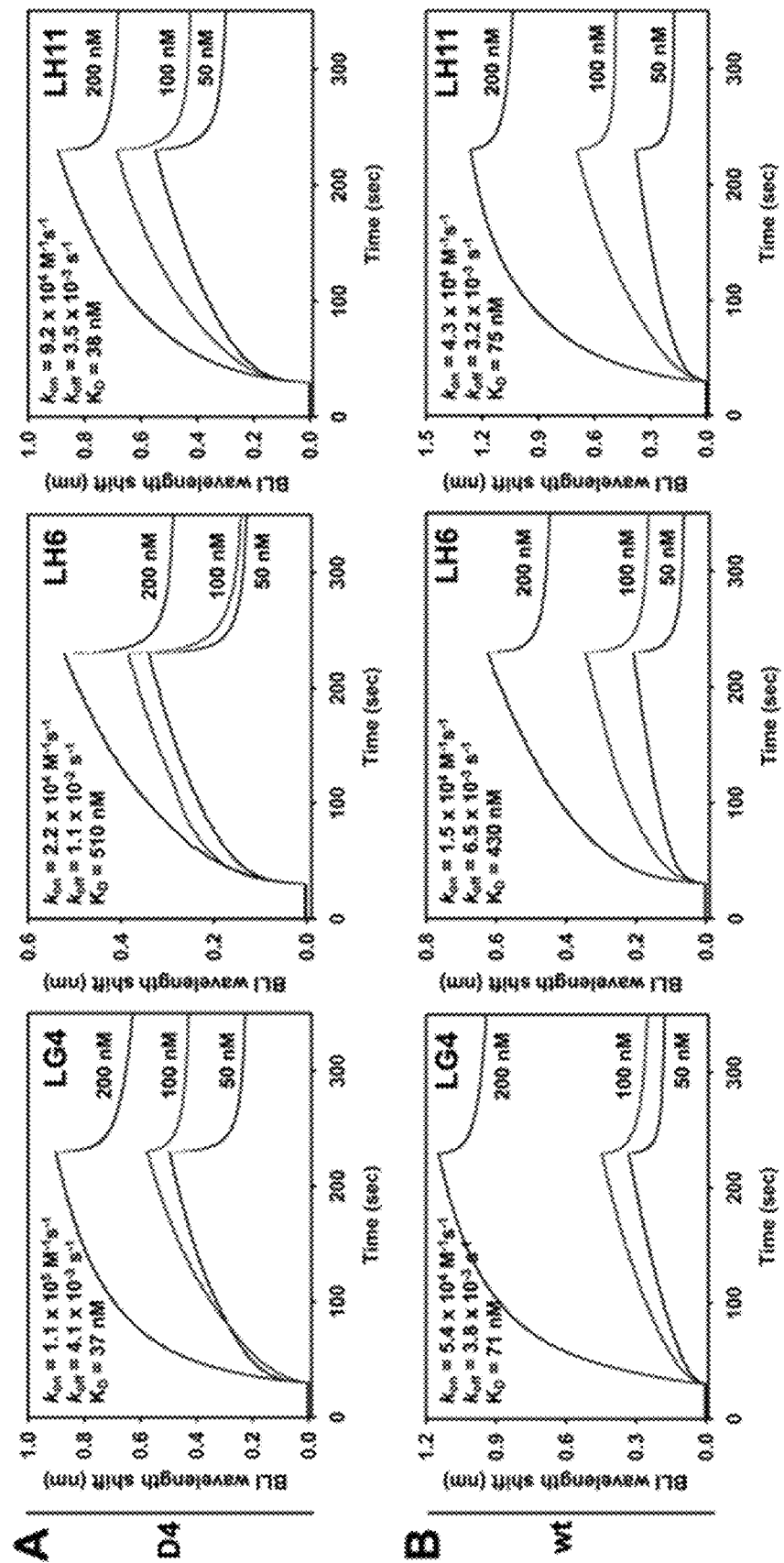
FIGS. 21A-21B. Binding kinetics of Fabs LG4, L116, and LH11 towards (FIG. 21A) cdMMP-12 D4 and (FIG. 21B) cdMMP-12 wt. Dissociation constants ($K_D$)s were determined at three Fab concentrations (50, 100, and 200 nM). $K_D$ values are presented in Table 3 and FIGS. 15A-15B.

In direct ELISA, Fabs LH11 and LG4 showed Sigmoidal dose-response curves with $EC_{50}$ values of 100 and 97 nM toward D4 (FIG. 15A), and 140 and 180 nM toward cdMMP-12 wt (FIG. 15B). These moderate decreases in affinities were consistent with binding kinetics measurements using bio-layer interferometry (e.g. Fab LH11 had a $K_D$ of 38 nM for D4 and a $K_D$ of 75 nM for cdMMP-12 wt) (FIGS. 21A-21B) and were unsurprising as D4 was used in Fab selection. For Fab LH6, both ELISA and kinetics results indicated a weaker interaction toward D4 and cdMMP-12 wt (FIGS. 15A-15B). Fab LH6 also exhibited relatively flat Sigmoidal curves and slow association rates ($k_{on}$s), presumably implying an induced fit between LH6 and cdMMP-12 D4/wt (Gakamsky, et al., (2007). *Proc Natl Acad Sci USA*, 104(42), 16639-16644).

Figures 22A, 22B:
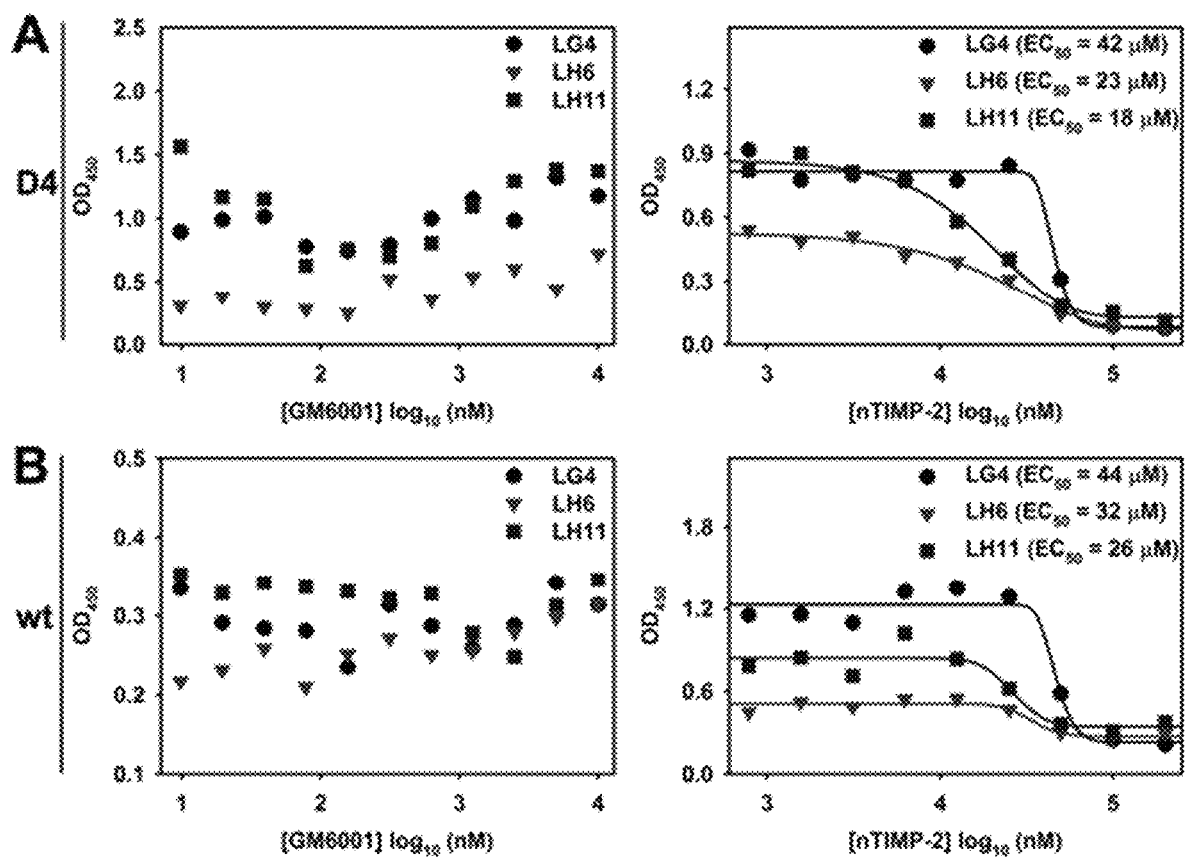
FIGS. 22A-22B. Competitive ELISA of Fabs LG4, L116, and LH11 toward (FIG. 22A) cdMMP-12 D4 and (FIG. 22B) cdMMP-12 wt. (Left) 10-10000 nM GM6001 and (right) 0.8-200 µM nTIMP-2 were used.

To further understand the possible binding epitopes of isolated Fabs on D4/wt cdMMP-12, we conducted competitive ELISA using N-terminal domains of tissue inhibitor of metalloproteinases (nTIMPs). As principal endogenous inhibitors of MMPs, TIMPs achieve their functions by direct binding at MMP reactive clefts and vicinity (Fernandez-Catalan, et al., (1998). *Embo j*, 17(17), 5238-5248), and thus have been used to provide insights on epitopes of mAbs that bind to MMPs. Initial BLItz tests suggested that both nTIMP-1 and -2 had relative weak affinities (e.g. 500 nM and 290 nM on D4) with cdMMP-12 compared to other MMPs (Table 7) (Lee, et al., (2017). *Microb Cell Fact*, 16(1), 73). With Fabs LH11/LG4/LH6 at their fixed sub-saturating concentrations, competitive ELISA was performed on immobilized cdMMP-12 D4/wt in the presence of increasing amounts of nTIMP-2. Results indicated that high concentrations of nTIMP-2 competed and replaced LH11/LG4/LH6 on their binding to D4/wt cdMMP-12 (FIGS. 22A-22B), suggesting that overlaps existed between the binding sites of the tested Fabs and that of nTIMP-2. Overall, isolated Fabs bound both D4 and wt cdMMP-12, likely at their reactive cleft and the surrounding vicinity.

Inhibitory Fabs are Functional on Physiological Substrates

Figures 16A, 16B:
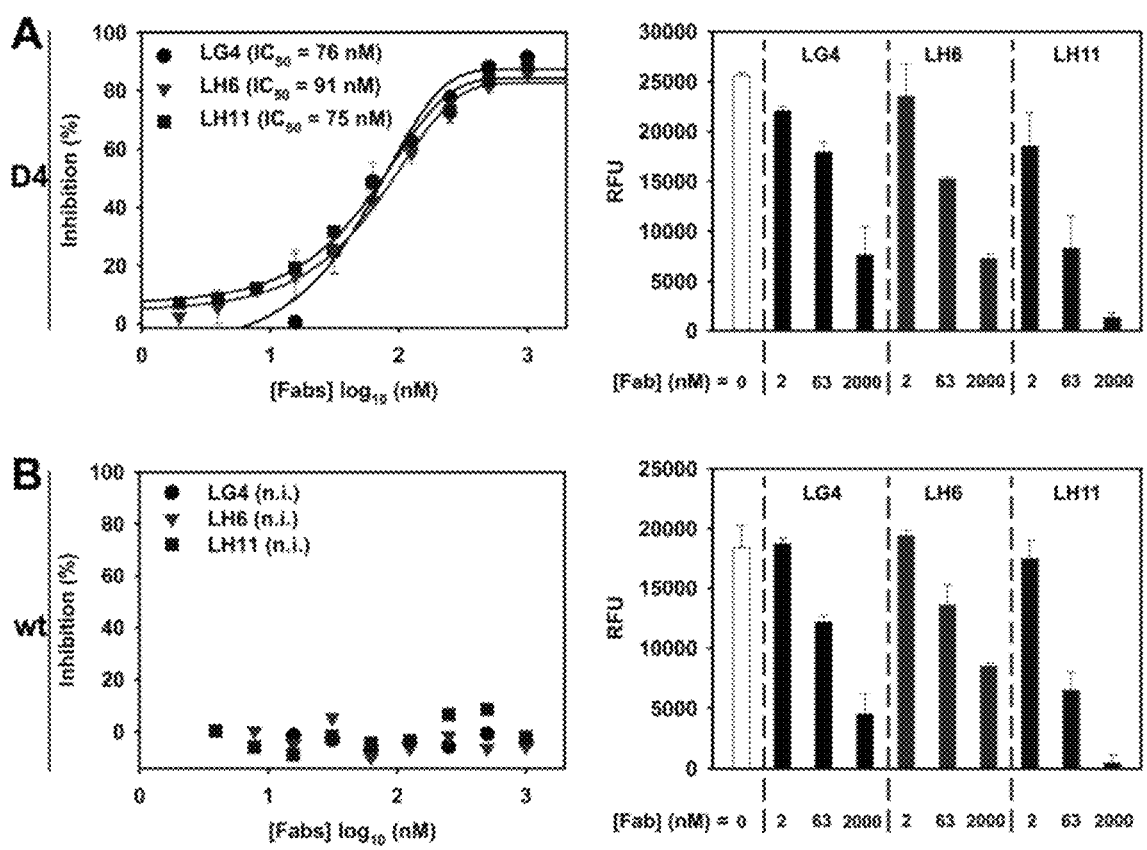
FIGS. 16A-16B. Inhibitory function of Fabs LG4, LH6, and LH11 towards (FIG. 16A) cdMMP-12 D4 and (FIG. 16B) cdMMP-12 wt. (Left) 1 µM FRET peptide or (right) 10 µg/mL elastin-FITC was used as the substrate and incubated with 7 nM cdMMP-12 D4/wt in the presence of 2 nM-2 µM purified Fabs. Assays were conducted in 50 mM Tris-HCl, 150 mM NaCl, 5 mM $CaCl_2$, 100 µM $ZnCl_2$ pH 7.5 at 37° C. for 20 min (with FRET peptide) or 12 h (with elastin-FITC). n.i., not inhibitory. RFU, relative fluorescent units.
Figures 17A, 17B:
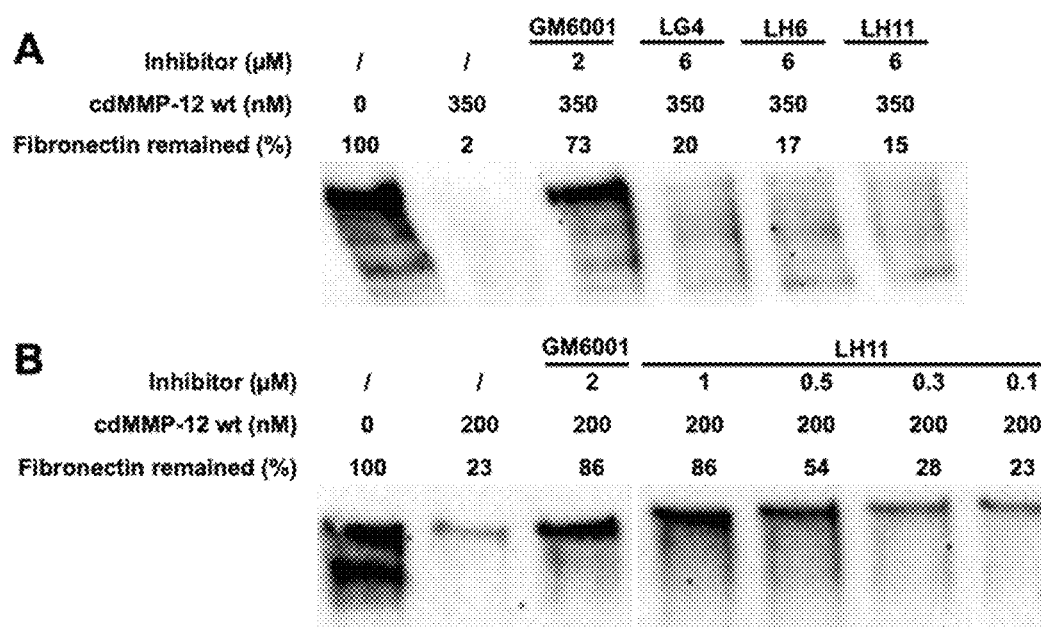
FIGS. 17A-17B. Inhibitory functions of Fabs on fibronectin proteolysis.

In inhibition assays using a quenched fluorescent peptide substrate, enzymatic activities of D4 were measured with 1 nM-1 µM Fabs LH11/LG4/LH6. Results revealed that these Fabs efficiently inhibited D4 on cleaving the FRET peptide substrate in a sigmoidal mode with $IC_{50}$ values ranging from 75 to 91 nM (FIG. 16A). Intriguingly, parallel assays with wt cdMMP-12 showed that these Fabs failed to inhibit wt cdMMP-12 on cleaving the peptide substrate (FIG. 16B). As it is not uncommon that protease inhibitory mAbs could behave differently toward various substrates (Shiryaev, et al., (2013). *Oncogenesis*, 2, e80; Wang, et al., (2013). *Curr Opin Struct Biol*, 23(6), 797-805), we further tested inhibitory functions of isolated Fabs with MMP-12 physiological substrates. Generally known as a potent elastase, MMP-12 also degrades fibronectin (Nagase, H. (2001). In N. J. Clendeninn & K. Appelt (Eds.), *Matrix Metalloproteinase Inhibitors in Cancer Therapy* (pp. 39-66). Totowa, N.J.: Humana Press; Van Doren, S. R. (2015). *Matrix Biol*, 44-46, 224-231), therefore we chose elastin conjugated with FITC and fibronectin for inhibition assays. Results indicated that under tested conditions, Fabs LH11/LG4/LH6 effectively reduced the hydrolysis of elastin-FITC mediated by cdMMP-12 D4/wt in a dose-dependent manner (FIGS. 16a-16B), and LH11 exhibited the highest potency among three tested Fabs. Particularly, after incubation with 7 nM wt cdMMP-12 and 10 µg/mL elastin-FITC at 37° C. for 12 h, 2/16/63/500/2000 nM Fab LH11 inhibited elastin-FITC hydrolysis 0/49/62/86/100%, giving an apparent inhibition $IC_{50}$ of 23 nM, which was slightly weaker than its potency on D4 ($IC_{50}$=18 nM) (Table 3). In fibronectin hydrolysis assays, incubation with 350 nM wt cdMMP-12 at 37° C. for 4 h completely hydrolyzed 200 nM fibronectin. In contrast, in the presence of either 2 µM GM6001 or 6 µM Fab LH11/LG4/LH6, significant amounts of fibronectin remained (FIG. 17A). Dose responses of 0.1-1 µM Fab LH11 on 200 nM wt cdMMP-12 with 200 nM fibronectin was further measured, and quantitative analysis estimated an $IC_{50}$ of 510 nM (FIG. 17B). Collectively, these results strongly supported that isolated Fabs efficiently inhibited cdMMP-12 from degrading macromolecular targets including elastin and fibronectin.

Inhibitory Fabs are Highly Selective

Selectivity of isolated Fabs toward cdMMP-12 over other MMPs was tested by measuring inhibition potency $K_I$s and binding dissociation constant $K_D$s (Table 4). Fabs LH11 and LH6 did not inhibit MMP-1 or MMP-7 in any detectable manner, and only weakly inhibited cdMMP-9 and cdMMP-14 with potencies at µM scale. For instance, Fab LH11 exhibited $K_I$s of 6.2 and 9.6 µM toward cdMMP-9 and cdMMP-14, which were 83-fold and 130-fold weaker compared to its potency on cdMMP-12 D4. In addition, Fabs LH11 and LG4 weakly bound cdMMP-9 and -14 with $K_D$ values of ~700 nM, representing a 9-10 fold drop of affinity over their binding with cdMMP-12 wt. Collectively, FRET inhibition assays and bio-layer interferometry results suggested that inhibitory Fabs were highly selective toward cdMMP12 over tested (cd)MMP-1/-7/-9/-14.

Isolated Fabs are Competitive Inhibitors and Proteolytically Stable

Figures 18A, 18B:
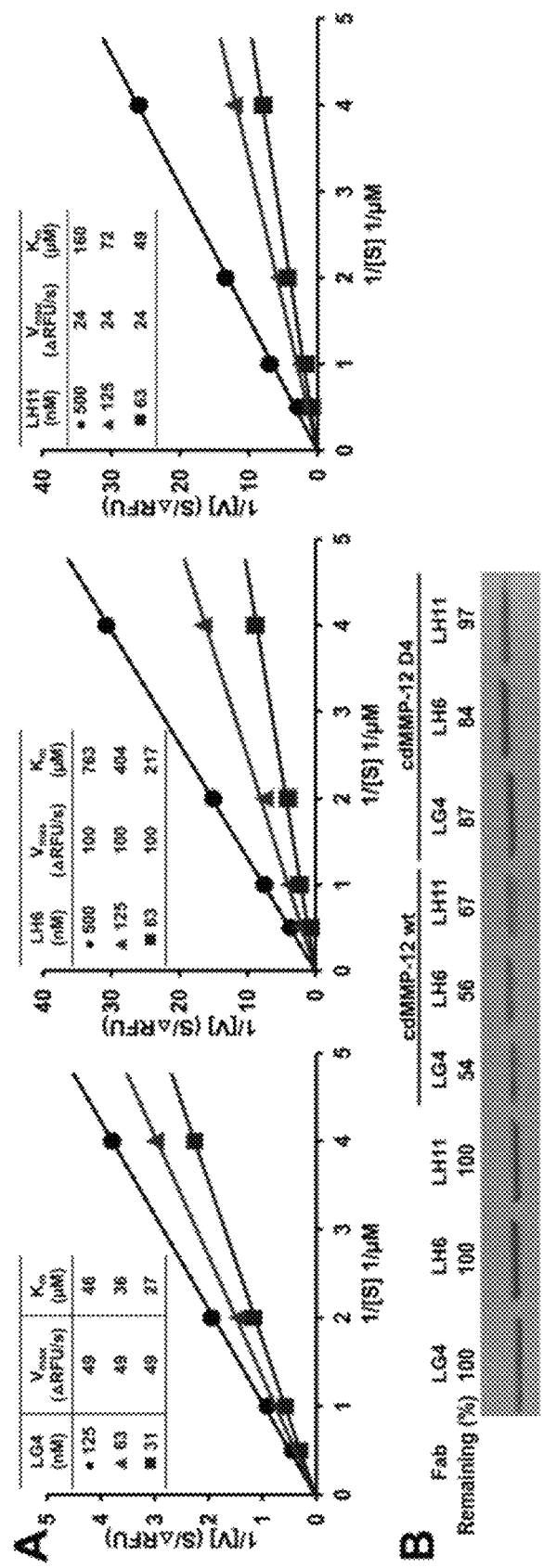
FIGS. 18A-18B. Inhibition type and stability of Fabs LG4, LH6, and LH11.
Figure 19:
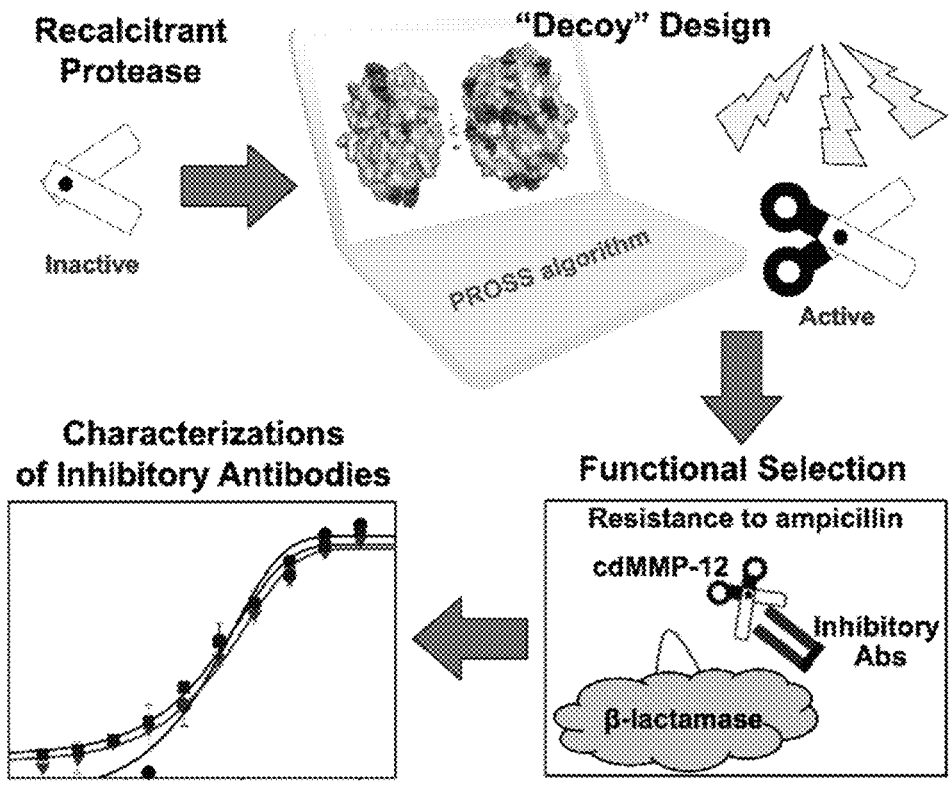
FIG. 19. By designing an expression-optimized protease mutant without disruption its reactive cleft and the vicinity, active-site mAbs raised against the "decoy" can maintain their inhibitory function toward the wild type protease.

Type of inhibition was determined by measuring cdMMP-12 D4 kinetics with the FRET peptide substrate in the presence of various concentrations of Fabs. Results showed that with increasing concentration of Fab LG4/LH6/LH11, cdMMP-12 D4 exhibited an unaltered maximum velocity ($V_{max}$) and an elevated Michaelis constant ($K_m$), indicating that these Fabs inhibited cdMMP-12 D4 proteolytic activity in a substrate competitive manner (FIG. 18A). To assess proteolytic stability of the inhibitory Fabs, 2 µM Fab LG4/LH6/LH11 were incubated with 2 µM cdMMP-12 D4/wt for 4 h at 37° C. and then analyzed by non-reducing SDS-PAGE. Densitometric analysis of the bands associated with full-length Fabs represented that no significant degradation of the Fabs by cdMMP-12 D4 was observed under tested condition (FIG. 18B). After exposure to cdMMP-12 wt for 4 h, Fabs LG4, LH6, and LH11 remained 54, 56, and 67% intact, respectively. These data agreed with our previous observations (Lopez, et al., (2019). *Proc Natl Acad Sci USA*, 116(33), 16314-16319) that isolated inhibitory mAbs by periplasmic genetic selection exhibited satisfactory proteolytic stability from the target protease.

Discussion

The human genome encodes more than 500 proteases, which act as processing enzymes influencing a wide variety of cell behaviors in health and disease (Lopez-Otin, (2007). *Nat Rev Cancer*, 7(10), 800-808; Turk, B. (2006). *Nat Rev Drug Discov*, 5(9), 785-799). In consequence, proteases represent an important group of pharmaceutical targets. However, to date only a small fraction of all therapeutically relevant proteases can be targeted by effective and safe inhibitors (Drag, M., & Salvesen, G. S. (2010). *Nat Rev Drug Discov*, 9(9), 690-701; Kenniston, et al., (2014). *J Biol Chem*, 289(34), 23596-23608). In addition to the general challenges faced by protease inhibition drug discovery, i.e. required high specificity and appropriate pharmacokinetic properties, heterologous expression of human proteases, which often results in insoluble/inactive products, can also present as a technical hurdle. In this study, we used macrophage metalloelastase (MMP-12) as an example and demonstrated that its mutants with improved expression could be applied for inhibitory mAb discovery. The underlying principle of this approach is that without disruption at the protease reactive cleft and the surrounding area, an orthosteric inhibitor raised against the mutant can maintain its function toward the wild type protease (FIGS. 13A-13B). Incorporating an expression-optimized "decoy" design with convex antibody library construction and functional selection (Lopez, et al., (2019). *Proc Natl Acad Sci USA*, 116(33), 16314-16319; Nam, et al., (2016). *Proc Natl Acad Sci USA*, 113(52), 14970-14975), Fabs inhibiting wild type cdMMP-12 were successfully isolated (Table 3). We expect that our novel methods can be applied for other proteases of biomedical importance.

The PROSS algorithm applies phylogenetic sequence information and atomistic Rosetta modeling to predict mutations that improve core packing, surface polarity, and folding rigidity (Goldenzweig, et al., (2016). *Mol Cell*, 63(2), 337-346). Through PROSS, the effects of individual mutations on energy difference (ΔΔGcaic) are calculated independently and a negative ΔΔGcaic cutoff rather than 0 is used to select potentially stabilizing mutations. All these approaches minimize false-positive predictions and the selected beneficial mutations are highly accumulative. Our result supports the robustness of the algorithm as omitting 4 out of 18 mutations in D4 still led a cdMMP-12 variant showing 6.1-fold activity improvement in the periplasm (Table 5).

Figure 23:
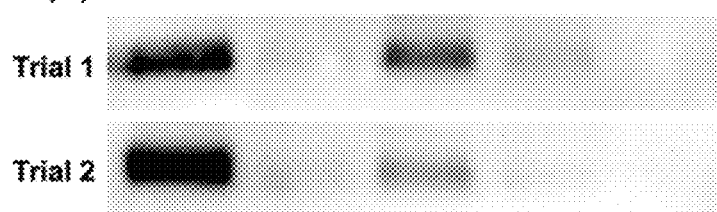
FIG. 23. Inhibitory functions of Fabs on proteolysis of modified TEM-1. 250 nM modified TEM-1 (carrying a N-terminal HA tag and cleavable sequence PLGLEEAK (SEQ ID NO:134)) was incubated with 700 nM cdMMP-12 wt in absence or presence of 10 µM Fab LG4, LH6, or LH11. Assays were conducted in 50 mM HEPES, 150 mM NaCl pH 7.5 at 37° C. for 4 h. Western blotting was developed with anti-HA-HRP. Relative quantities were analyzed by densitometric analysis from two independent measurements.

Isolated cdMMP-12 Fabs were active-site competitive inhibitors exhibiting nM range affinity, decent proteolytic stability, and high selectivity over other tested (cd)MMPs (FIG. 15A-15C, FIGS. 16A-16B, FIGS. 18A-18B, FIGS. 22A-22B, Table 4). Importantly, they also efficiently inhibited wt cdMMP-12 on hydrolyzing physiological substrates elastin and fibronectin (FIGS. 16A-16B, FIGS. 17A-17B). One intriguing observation was that isolated Fabs could inhibit mutant D4 but not cdMMP-12 wt on cleaving a FRET peptide substrate (FIGS. 16A-16B). To explain this disparity, we reasoned that the active-site of D4 could be effectively blocked by the raised Fabs via a tight binding, however the weaker interaction between the Fabs and wt cdMMP-12 (FIGS. 15A-15B, FIGS. 21A-21B) could make its active-site accessible for the short peptide substrate. Results of competitive ELISA with GM6001, a highly potent hydroxamate MMP inhibitor, indicated that high concentration of GM6001 could not replace Fabs on binding with wt cdMMP-12 (FIGS. 22A-22B), suggesting that Fab-cdMMP12 wt complex was accessible for GM6001 and presumably for the peptide substrate. When modified TEM-1 (PLGLEEAK (SEQ ID NO:134)) was used as the substrate, Fab LG4 but not LH11 showed significant inhibition (FIG. 23), though LH11 was more potent than LG4 on elastin and fibronectin. Such substrate-dependent potencies have also been reported for BACE-1 inhibitory mAbs (Wang, et al., (2013). *Curr Opin Struct Biol*, 23(6), 797-805), which had a higher potency with a 27-mer synthetic APP substrate than with a 9-mer peptide substrate. Further structural study suggested that the anti-BACE1 was an allosteric inhibitor and its binding induced BACE1 conformation changes along the substrate-binding cleft and thus affected its catalytic efficiency. Similarly, anti-MMP-14 mAb 9E8 exhibited its inhibitory function on pro-MMP-2 activation alone rather than the typical proteolytic and pro-migratory activities of MMP-14 (Shiryaev, et al., (2013). Oncogenesis, 2, e80). Taken together, these results support the notion that it is possible to develop mAbs inhibiting the target protease in a substrate-dependent manner, a unique and desirable feature for certain therapeutic application.

CONCLUSION

This study validated the feasibility of developing inhibitory mAbs by using target protease mutant as a decoy. Combining three advances in the field—PROSS algorithm for cdMMP-12 mutant design, convex paratope antibody library construction, and functional selection for inhibitory mAbs—potent mAb inhibitors with high selectivity targeting MMP-12 were successfully isolated. In addition to potential pharmaceutical application, isolated mAbs can also be used as research tools to identify MMP-12 functionality in normal and pathophysiological conditions ranging from several inflammatory and neurological diseases (Chelluboina, et al., (2018). *Mol Neurobiol*, 55(2), 1405-1409). Overall, we expect that this method could be significantly reused to develop inhibitory mAbs targeting recalcitrant proteases of biomedical importance.

TABLE 3

Characterizations of isolated inhibitory antibodies

| | | Toward cdMMP-12 mutant D4 | | | |
|---|---|---|---|---|---|
| | | Binding | | Inhibition | |
| Fab | CDR-H3 sequence (length) | ELISABlitz $EC_{50}$ (nM) | $K_D$ (nM) | FRET peptide $K_I$ (nM) | Elastin-FITC $IC_{50}$ (nM) |
| LH11 | FLLSIGKLFVGDGSILHVWLYGMDY (25) (SEQ ID NO: 129) | 100 | 38 | 75 | 18 |
| LG4 | SPIVYYELFIVIFIDMGAQGWKYGMDY (25) (SEQ ID NO: 117) | 97 | 37 | 76 | 210 |
| LH6 | DLEESLPKRARTAVSKELESVPYVMDY (27) (SEQ ID NO: 123) | 290 | 510 | 91 | 61 |
| LG6 | VFKWRRSAGTVKFYVHEAYGMDY (23) (SEQ ID NO: 144) | | | | 110 |
| LH5 | VTSDRVGVGREALRAHATLGYAMDY (25) (SEQ ID NO: 145) | | | | 360 |
| 12F6-7 | ALLSSTIFQSHTPLPTLEQRYAMDY (25) (SEQ ID NO: 146) | | | | 580 |
| 12E4-6 | GKLENPYWIDLKDLSQPTRMYGMDY (25) (SEQ ID NO: 147) | | | | 660 |

TABLE 3 -continued

Toward cdMMP-12 wide-type

| Fab | CDR-H3 sequence (length) | Binding ELISABlitz $EC_{50}$ (nM) | Binding $K_D$ (nM) | FRET peptide | Inhibition Elastin-FITC $IC_{50}$ (nM) | Fibronectin $IC_{50}$ (nM) |
|---|---|---|---|---|---|---|
| LH11 | FLLSIGKLFVGDGSILHVWLYGMDY (25) (SEQ ID NO: 129) | 140 | 75 | non-inhib | 23 | 510 |
| LG4 | SPIVYYELFIVIFIDMGAQGWKYGMDY (25) (SEQ ID NO: 117) | 180 | 71 | non-inhib | 350 | Inhib. |
| LH6 | DLEESLPKRARTAVSKELESVPYVMDY (27) (SEQ ID NO: 123) | ~1000 | 430 | non-inhib | 1700 | Inhib. |
| LG6 | VFKWRRSAGTVKFYVHEAYGMDY (23) (SEQ ID NO: 144) | | | | | |
| LH5 | VTSDRVGVGREALRAHATLGYAMDY (25) (SEQ ID NO: 145) | | | | | |
| 12F6-7 | ALLSSTIFQSHTPLPTLEQRYAMDY (25) (SEQ ID NO: 146) | | | | | |
| 12E4-6 | GKLENPYWIDLKDLSQPTRMYGMDY (25) (SEQ ID NO: 147) | | | | | |

TABLE 4

Selectivity of isolated inhibitory antibodies

| Fab | MMP-1 | MMP-7 | cdMMP-9 | cdMMP-14 |
|---|---|---|---|---|
| LH11 | non-inhib. | non-inhib. | $K_D$ = 740 nM (9.9-fold), $K_I$ = 6.2 µM (83-fold) | $K_D$ = 780 nM (10-fold), $K_I$ = 9.6 µM (130-fold) |
| LG4 | — | — | $K_D$ = 720 nM (10-fold) | $K_D$ = 640 nM (9.0-fold) |
| LH6 | non-inhib. | non-inhib. | $K_D$ = 950 nM (2.2-fold), $K_I$ = 1.5 µM (16-fold) | $K_D$ = 480 nM (1.1-fold), $K_I$ = 4.7 µM (52-fold) |

Note:
$K_D$ values are compared with cdMMP-12 wt.
$K_I$ values are compared with cdMMP-12 mutant D4.
—, not determined.

TABLE 5

Activities of periplasmic cdMMP-12 (ΔRFU/min) and culture condition optimization

| cdMMP-12 | Temperature/IPTG | | | |
|---|---|---|---|---|
| | RT/– | RT/+ | 30° C./– | 30° C./+ |
| wt | 11 ± 1.1 | 18 ± 0.4 | 12 ± 1.7 | 14 ± 0.3 |
| D1 | 19 ± 1.8 | 42 ± 0.6 | 9.6 ± 2.0 | 45 ± 0.2 |
| D4 | 50 ± 1.4 | 55 ± 7.5 | 110 ± 2.1 | 9.8 ± 0.4 |
| D7 | 6.4 ± 0.5 | 8.4 ± 0.4 | 7.4 ± 0.7 | 7.4 ± 0.3 |

Note:
1. 0.8 $OD_{600}$ of cells were used for periplasmic fraction preparations
2. Activities of unpurified cdMMP-12 were assayed with FRET peptide substrate
3. The best tested culture conditions for each cdMMP-12 variant are in bold

TABLE 6

Inhibitory mAb isolation conditions and selection results

| Cleavable peptide on TEM-1 | PLGLEEAK (SEQ ID NO: 134) |
|---|---|
| Library size | 3.3 × 10⁸ |
| Initial selection | |
| [Amp] (µg/mL) | 500 |
| [IPTG] (mM) | 0 |
| Temp (° C.) | 30 |
| # of clones remaining | 1500 |
| Secondary screening | |
| [Amp] (µg/mL) | 700 |
| [IPTG] (mM) | 0 |
| Temp (° C.) | 30 |
| # of clones remaining | 100 |
| Sequenced | 16 |
| Unique correct sequences | 13 |
| Inhibitors | 13 |
| nM range inhibitors | 7 |

TABLE 7

Affinity of nTIMP-1 and nTIMP-2 on cdMMP-12 D4/wt (nM)

| cdMMP12 | nTIMP-1 | nTIMP-2 |
|---|---|---|
| D4 | 500 | 290 |
| wt | 480 | 150 |

TABLE 8

Sequences

| SEQ ID NO: | Sequence | Description |
|---|---|---|
| 88 | DIQMTQSPSSLSASVGDRVTITCRASQSVSSAVAWYQQKPGKAPKLLIYSA SSLYSGVPSRFSGSRSGTDFTLTISSLQPEDFATYYCQQYSYGYSSLITFG QGTKVEIKR | Clone 2B4: light chain variable region; CDRs bolded. |
| 34 | RASQSVSSAVA | Clone 2B4: CDR-L1 |
| 35 | SASSLYS | Clone 2B4: CDR-L2 |
| 89 | QQYSYGYSSLIT | Clone 2B4: CDR-L3 |
| 1 | EVQLVESGGGLVQPGGSLRLSCAASGFNLYSSYIHWVRQAPGKGLEWVASI YSSYSSTYYADSVKGRFTISADTSKNTAYLQMNSLRAEDTAVYYCARSDSA VYSVRRMGSSGLAAYAMDYWGQGTLVTVSSAS | Clone 2B4: heavy chain variable region; CDRs bolded. |
| 2 | GFNLYSSYIH | Clone 2B4: CDR-H1 |
| 3 | SIYSSYSSTYYADSVK | Clone 2B4: CDR-H2 |
| 4 | SDSAVYSVRRMGSSGLAAYAMDY | Clone 2B4: CDR-H3 |
| 90 | DIQMTQSPSSLSASVGDRVTITCRASQSVSSAVAWYQQKPGKAPKLLIYSA SSLYSGVPSRFSGSRSGTDFTLTISSLQPEDFATYYCQQWGPHYAPITFGQ GTKVEIKR | Clone 2B12: light chain variable region; CDRs bolded. |
| 34 | RASQSVSSAVA | Clone 2B12: CDR-L1 |
| 35 | SASSLYS | Clone 2B12: CDR-L2 |
| 91 | QQWGPHYAPIT | Clone 2B12: CDR-L3 |
| 5 | EVQLVESGGGLVQPGGSLRLSCAASGFNIYYSSMHWVRQAPGKGLEWVAYI YSSSSYTYYADSVKGRFTISADTSKNTAYLQMNSLRAEDTAVYYCARDCCS CVFSQSAGITLACVYVMDYWGQGTLVTVSSAS | Clone 2B12: heavy chain variable region; CDRs bolded. |
| 6 | GFNIYYSSMH | Clone 2B12: CDR-H1 |
| 7 | YIYSSSSYTYYADSVK | Clone 2B12: CDR-H2 |
| 8 | DCCSCVFSQSAGITLACVYVMDY | Clone 2B12: CDR-H3 |
| 92 | DIQMTQSPSSLSASVGDRVTITCRASQSVSSAVAWYQQKPGKAPKLLIYSA SSLYSGVPSRFSGSRSGTDFTLTISSLQPEDFATYYCQQYSGPYPITFGQG TKVEIKR | Clone 1A5: light chain variable region; CDRs bolded. |
| 34 | RASQSVSSAVA | Clone 1A5: CDR-L1 |
| 35 | SASSLYS | Clone 1A5: CDR-L2 |
| 93 | QQYSGPYPIT | Clone 1A5: CDR-L3 |
| 9 | EVQLVESGGGLVQPGGSLRLSCAASGFNLYYYYMHWVRQAPGKGLEWVAYI YPYSGSTYYADSVKGRFTISADTSKNTAYLQMNSLRAEDTAVYYCARLDFL MRDIYYDLGGGALGWLIKYAMDYWGQGTLVTVSSAS | Clone 1A5: heavy chain variable region; CDRs bolded. |
| 10 | GFNLYYYYMH | Clone 1A5: CDR-H1 |
| 11 | YIYPYSGSTYYADSVK | Clone 1A5: CDR-H2 |
| 12 | LDFLMRDIYYDLGGGALGWLIKYAMDY | Clone 1A5: CDR-H3 |
| 94 | DIQMTQSPSSLSASVGDRVTITCRASQSVSSAVAWYQQKPGKAPKLLIYSA SSLYSGVPSRFSGSRSGTDFTLTISSLQPEDFATYYCQQYSVAYVWLITFG QGTKVEIKR | Clone 2B10: light chain variable region; CDRs bolded. |
| 34 | RASQSVSSAVA | Clone 2B10: CDR-L1 |
| 35 | SASSLYS | Clone 2B10: CDR-L2 |
| 95 | QQYSVAYVWLIT | Clone 2B10: CDR-L3 |
| 13 | EVQLVESGGGLVQPGGSLRLSCAASGFNIYYSYMHWVRQAPGKGLEWVASI YPSYGYTYYADSVKGRFTISADTSKNTAYLQMNSLRAEDTAVYYCARQLFA CWRQSILTPPLLSAMMMGYAMDYWGQGTLVTVSSAS | Clone 2B10: heavy chain variable region; CDRs bolded. |
| 14 | GFNIYYSYMH | Clone 2B10: CDR-H1 |

TABLE 8 -continued

Sequences

| SEQ ID NO: | Sequence | Description |
|---|---|---|
| 15 | SIYPSYGYTYYADSVK | Clone 2B10: CDR-H2 |
| 16 | QLFACWRQSILTPPLLSAMMMGYAMDY | Clone 2B10: CDR-H3 |
| 96 | DIQMTQSPSSLSASVGDRVTITCRASQSVSSAVAWYQQKPGKAPKLLIYSASSLYSGVPSRFSGSRSGTDFTLTISSLQPEDFATYYCQQSSYSLITFGQGTKVEIKR | Clone 2D9: light chain variable region; CDRs bolded. |
| 34 | RASQSVSSAVA | Clone 2D9: CDR-L1 |
| 35 | SASSLYS | Clone 2D9: CDR-L2 |
| 97 | QQSSYSLIT | Clone 2D9: CDR-L3 |
| 17 | EVQLVESGGGLVQPGGSLRLSCAASGFNISSSSMHWVRQAPGKGLEWVASIYPYYGYTYYADSVKGRFTISADTSKNTAYLQMNSLRAEDTAVYYCARGVTRFTNDASVGQVWAGAYGMDYWGQGTLVTVSSAS | Clone 2D9: heavy chain variable region; CDRs bolded. |
| 18 | GFNISSSSMH | Clone 2D9: CDR-H1 |
| 19 | SIYPYYGYTYYADSVK | Clone 2D9: CDR-H2 |
| 20 | GVTRFTNDASVGQVWAGAYGMDY | Clone 2D9: CDR-H3 |
| 98 | DIQMTQSPSSLSASVGDRVTITCRASQSVSSAVAWYQQKPGKAPKLLIYSASSLYSGVPSRFSGSRSGTDFTLTISSLQPEDFATYYCQQSSFPFTFGQGTKVEIKR | Clone 2A6: light chain variable region; CDRs bolded. |
| 34 | RASQSVSSAVA | Clone 2A6: CDR-L1 |
| 35 | SASSLYS | Clone 2A6: CDR-L2 |
| 99 | QQSSFPFT | Clone 2A6: CDR-L3 |
| 21 | EVQLVESGGGLVQPGGSLRLSCAASGFNFSSSSIHWVRQAPGKGLEWVASISSSYGYTYYADSVKGRFTISADTSKNTAYLQQNSLRAEDTAVYYCARVVRMLPVRCIPRCIKTTLPLYGMDYWGQGTLVTVSSAS | Clone 2A6: heavy chain variable region; CDRs bolded. |
| 22 | GFNFSSSSIH | Clone 2A6: CDR-H1 |
| 23 | SISSSYGYTYYADSVK | Clone 2A6: CDR-H2 |
| 24 | VVRMLPVRCIPRCIKTTLPLYGMDY | Clone 2A6: CDR-H3 |
| 25 | DIQMTQSPSSLSASVGDRVTITCRASQSVGTYLNWYQQKPGKAPKLLIYATSNLRSGVPSRFSGSGSGTDFTLTISSLQPEDFATYYCQQSYSIPRFTFGPGTKLEIKR | Clone B3B12: light chain variable region; CDRs bolded. |
| 26 | RASQSVGTYLN | Clone B3B12: CDR-L1 |
| 27 | ATSNLRS | Clone B3B12: CDR-L2 |
| 28 | QQSYSIPRFT | Clone B3B12: CDR-L3 |
| 29 | EVQLVESGGGLVQPGGSLRLSCAASGFNIPYSSMHWVRQAPGKGLEWVASISSYSSSTSYADSVKGRFTISADTSKNTAYLQMNSLRAEDTAVYYCARYICGHRWRDFDMWRARTGVNYAMDYWGQGTLVTVSSAS | Clone B3B12: heavy chain variable region; CDRs bolded. |
| 30 | GFNIPYSSMH | Clone B3B12: CDR-H1 |
| 31 | SISSYSSSTSYADSVK | Clone B3B12: CDR-H2 |
| 32 | YICGHRWRDFDMWRARTGVNYAMDY | Clone B3B12: CDR-H3 |
| 33 | DIQMTQSPSSLSASVGDRVTITCRASQSVSSAVAWYQQKPGKAPKLLIYSASSLYSGVPSRFSGSRSGTDFTPTISSLQPEDFATYYCQQASASPYALITFGQGTKVEIKR | Clone B 1A4: light chain variable region; CDRs bolded. |
| 34 | RASQSVSSAVA | Clone B1A4: CDR-L1 |
| 35 | SASSLYS | Clone B1A4: CDR-L2 |
| 36 | QQASASPYALIT | Clone B1A4: CDR-L3 |

TABLE 8 -continued

Sequences

| SEQ ID NO: | Sequence | Description |
|---|---|---|
| 37 | EVQLVESGGGLVQPGGSLRLSCAASGFNISYSSIHWVRQAPGKGLEWVAYISPSSSYTSYADSVKGRFTISADTSKNTAYLQMNSLRAEDTAVYYCARHYYVSVGSGIDYWGQGTLVTVSSAS | Clone B1A4: heavy chain variable region; CDRs bolded. |
| 38 | GFNISYSSIH | Clone B1A4: CDR-H1 |
| 39 | YISPSSSYTSYADSVK | Clone B1A4: CDR-H2 |
| 40 | HYYVSVGSGIDY | Clone B1A4: CDR-H3 |
| 100 | DIQMTQSPSSLSASVGDRVTITCRASQSVSSAVAWYQQKPGKAPKLLIYSASSLYSGVPSRFSGSRSGTDFTPTISSLQPEDFATYYCQQSYFSYPITFGQGTKVEIKR | Clone B2B5: light chain variable region; CDRs bolded. |
| 34 | RASQSVSSAVA | Clone B2B5: CDR-L1 |
| 35 | SASSLYS | Clone B2B5: CDR-L2 |
| 101 | QQSYFSYPIT | Clone B2B5: CDR-L3 |
| 41 | EVQLVESGGGLVQPGGSLRLSCAASGFNIYYSYMHWVRQAPGKGLEWVASIYPYYGSTYYADSVKGRFTISADTSKNTAYLQMNSLRAEDTAVYYCARWHGYPPGYSYYSSFSSSGFDYWGQGTLVTVSSAS | Clone B2B5: heavy chain variable region; CDRs bolded. |
| 14 | GFNIYYSYMH | Clone B2B5: CDR-H1 |
| 42 | SIYPYYGSTYYADSVK | Clone B2B5: CDR-H2 |
| 43 | WHGYPPGYSYYSSFSSSGFDY | Clone B2B5: CDR-H3 |
| 44 | DIQMTQSPSSLSASVGDRVTITCRASQSVSSAVAWYQQKPGKAPKLLIYSASSLYSGVPSRFSGSRSGTDFTLTISSLQPEDFATYYCQQYGYYLITFGQGTKVEIKR | Clone B2B2: light chain variable region; CDRs bolded. |
| 34 | RASQSVSSAVA | Clone B2B2: CDR-L1 |
| 35 | SASSLYS | Clone B2B2: CDR-L2 |
| 45 | QQYGYYLIT | Clone B2B2: CDR-L3 |
| 46 | EVQLVESGGGLVQPGGSLRLSCAASGFNISSYYMHWVRQAPGKGLEWVASIYSSYGYTYYADSVKGRFTISADTSKNTAYLQMNSLRAEDTAVYYCARYWGYYAWFGSHPWAYGAFDYWGQGTLVTVSSAS | Clone B2B2: heavy chain variable region; CDRs bolded. |
| 47 | GFNISSYYMH | Clone B2B2: CDR-H1 |
| 48 | SIYSSYGYTYYADSVK | Clone B2B2: CDR-H2 |
| 49 | YWGYYAWFGSHPWAYGAFDY | Clone B2B2: CDR-H3 |
| 102 | DIQMTQSPSSLSASVGDRVTITCRASQSVSSAVAWYQQKPGKAPKLLIYSASSLYSGVPSRFSGSRSGTDFTLTISSLQPEDFATYYCQQSGYAPFTFGQGTKVEIKR | Clone B2B3: light chain variable region; CDRs bolded. |
| 34 | RASQSVSSAVA | Clone B2B3: CDR-L1 |
| 35 | SASSLYS | Clone B2B3: CDR-L2 |
| 103 | QQSGYAPFT | Clone B2B3: CDR-L3 |
| 50 | EVQLVESGGGLVQPGGSLRLSCAASGFNISYSSIHWVRQAPGKGLEWVAYISSYSSSTYYADSVKGRFTISADTSKNTAYLQMNSLRAEDTAVYYCARSASGIDYWGQGTLVTVSSAS | Clone B2B3: heavy chain variable region; CDRs bolded. |
| 38 | GFNISYSSIH | Clone B2B3: CDR-H1 |
| 51 | YISSYSSSTYYADSVK | Clone B2B3: CDR-H2 |
| 52 | SASGIDY | Clone B2B3: CDR-H3 |
| 96 | DIQMTQSPSSLSASVGDRVTITCRASQSVSSAVAWYQQKPGKAPKLLIYSASSLYSGVPSRFSGSRSGTDFTLTISSLQPEDFATYYCQQSSYSLITFGQGTKVEIKR | Clone B2B9: light chain variable region; CDRs bolded. |
| 34 | RASQSVSSAVA | Clone B2B9: CDR-L1 |

TABLE 8-continued

Sequences

| SEQ ID NO: | Sequence | Description |
| --- | --- | --- |
| 35 | SASSLYS | Clone B2B9: CDR-L2 |
| 97 | QQSSYSLIT | Clone B2B9: CDR-L3 |
| 53 | EVQLVESGGGLVQPGGSLRLSCAASGFNISYSSMHWVRQAPGKGLEWVASI YPSYSYTSYADSVKGRFTISADTSKNTAYLQMNSLRAEDTAVYYCARSSSS YYYGMDYWGQGTLVTVSSAS | Clone B2B9: heavy chain variable region; CDRs bolded. |
| 54 | GFNISYSSMH | Clone B2B9: CDR-H1 |
| 55 | SIYPSYSYTSYADSVK | Clone B2B9: CDR-H2 |
| 56 | SSSSYYYGMDY | Clone B2B9: CDR-H3 |
| 57 | EVQLVESGGGLVQPGGSLRLSCAASGFNIYSSSMHWVRQAPGKGLEWVAYI YSSYGYTYYADSVKGRFTISADTSKNTAYLQMNSLRAEDTAVYYCARDNSI CVLTQKEVDTKFLVGQHSYVMDYWGQGTLVTVSSAS | Clone B2B6: heavy chain variable region; CDRs bolded. |
| 58 | GFNIYSSSMH | Clone B2B6: CDR-H1 |
| 59 | YIYSSYGYTYYADSVK | Clone B2B6: CDR-H2 |
| 60 | DNSICVLTQKEVDTKFLVGQHSYVMDY | Clone B2B6: CDR-H3 |
| 104 | DIQMTQSPSSLSASVGDRVTITCRASQSVSSAVAWYQQKPGKAPKLLIYSA SSLYSGVPSRFSGSRSGTDFTLTISSLQPEDFA-TYYCQQSGHYHSLITFGQ GTKVEIKR | Clone B1B3: light chain variable region; CDRs bolded. |
| 34 | RASQSVSSAVA | Clone B1B3: CDR-L1 |
| 35 | SASSLYS | Clone B1B3: CDR-L2 |
| 105 | QQSGHYHSLIT | Clone B1B3: CDR-L3 |
| 61 | EVQLVESGGGLVQPGGSLRLSCAASGFNISYYSMHWVRQAPGKGLEWVASI SPYYGSTYYADSVKGRFTISADTSKNTAYLQMNSLRAEDTAVYYCARERSS CPVGWRDSRFGADGYGLEYWGQGTLVTVSSAS | Clone B1B3: heavy chain variable region; CDRs bolded. |
| 62 | GFNISYYSMH | Clone B1B3: CDR-H1 |
| 63 | SISPYYGSTYYADSVK | Clone B1B3: CDR-H2 |
| 64 | ERSSCPVGWRDSRFGADGYGLEY | Clone B1B3: CDR-H3 |
| 106 | DIQMTQSPSSLSASVGDRVTITCRASQSVSSAVAWYQQKPGKAPKLLIYSA SSLYSGVPSRFSGSRSGTDFTLTISSLQPEDFATYYCQQASHLITFGQGTK VEIKR | Clone A4A1: light chain variable region; CDRs bolded. |
| 34 | RASQSVSSAVA | Clone A4A1: CDR-L1 |
| 35 | SASSLYS | Clone A4A1: CDR-L2 |
| 107 | QQASHLIT | Clone A4A1: CDR-L3 |
| 65 | EVQLVESGGGLVQPGGSLRLSCAASGFNISSYYIHWVRQAPGKGLEWVASI YSYSSYTYYADSVKGRFTISADTSKNTAYLQMNSLRAGDTAVYYCARFGSW SYAIDYWGQGTLVTVSSAS | Clone A4A1: heavy chain variable region; CDRs bolded. |
| 66 | GFNISSYYIH | Clone A4A1: CDR-H1 |
| 67 | SIYSYSSYTYYADSVK | Clone A4A1: CDR-H2 |
| 68 | FGSWSYAIDY | Clone A4A1: CDR-H3 |
| 106 | DIQMTQSPSSLSASVGDRVTITCRASQSVSSAVAWYQQKPGKAPKLLIYSA SSLYSGVPSRFSGSRSGTDFTLTISSLQPEDFATYYCQQASHLITFGQGTK VEIKR | Clone A4A2: light chain variable region; CDRs bolded. |
| 34 | RASQSVSSAVA | Clone A4A2: CDR-L1 |
| 35 | SASSLYS | Clone A4A2: CDR-L2 |
| 107 | QQASHLIT | Clone A4A2: CDR-L3 |

TABLE 8 -continued

Sequences

| SEQ ID NO: | Sequence | Description |
|---|---|---|
| 69 | EVQLVESGGGLVQPGGSLRLSCAASGFNLSSSSMHWVRQAPGKGLEWVASIYPSYSYTYYADSVKGRFTISADTSKNTAYLQMNSLRAEDTAVYYCARKTSDQYLLVGGSFFKLRDCCYVMDYWGQGTLVTVSSAS | Clone A4A2: heavy chain variable region; CDRs bolded. |
| 70 | GFNLSSSSMH | Clone A4A2: CDR-H1 |
| 71 | SIYPSYSYTYYADSVK | Clone A4A2: CDR-H2 |
| 72 | KTSDQYLLVGGSFFKLRDCCYVMDY | Clone A4A2: CDR-H3 |
| 73 | EVQLVESGGGLVQPGGSLRLSCAASGFNIYYSYIHWVRQAPGKGLEWVASIYSYYGYTYYADSVKGRFTISADTSKNTAYLQMNSLRAEDTAVYYCAR-GRSPGPYAVCGNLFRSVSYGMDYWGQGTLVTVSSAS | Clone A4A7: heavy chain variable region; CDRs bolded. |
| 74 | GFNIYYSYIH | Clone A4A7: CDR-H1 |
| 75 | SIYSYYGYTYYADSVK | Clone A4A7: CDR-H2 |
| 76 | GRSPGPYAVCGNLFRSVSYGMDY | Clone A4A7: CDR-H3 |
| 77 | EVQLVESGGGLVQPGGSLRLSCAASGFNISYYYMHWVRQAPGKGLEWVASIYPSSGSTYYADSVKGRFTISADTSKNTAYLQMNSLRAEDTAVYYCARGFAWSPGLDYWGQGTLVTVSSAS | Clone CBA3: heavy chain variable region; CDRs bolded. |
| 78 | GFNISYYYMH | Clone CBA3: CDR-H1 |
| 79 | SIYPSSGSTYYADSVK | Clone CBA3: CDR-H2 |
| 80 | GFAWSPGLDY | Clone CBA3: CDR-H3 |
| 108 | DIQMTQSPSSLSASVGDRVTITCRASQSVSSAVAWYQQKPGKAPKLLIYSASSLYSGVPSRFSGSRSGTDFTLTISSLQPEDFATYYCQQWSSSWGYLITFGQGTKVEIKR | Clone CBA2: light chain variable region; CDRs bolded. |
| 34 | RASQSVSSAVA | Clone CBA2: CDR-L1 |
| 35 | SASSLYS | Clone CBA2: CDR-L2 |
| 109 | QQWSSSWGYLIT | Clone CBA2: CDR-L3 |
| 81 | EVQLVESGGGLVQPGGSLRLSCAASGFNIYYYSIHWVRQAPGKGLEWVAYIYSYYGSTYYADSVKGRFTISADTSKNTAYLQMNSLRAEDTAVYY-CARYGYPGGYHFWGWWSSPYAFDYWGQGTLVTVSSAS | Clone CBA2: heavy chain variable region; CDRs bolded. |
| 82 | GFNIYYYSIH | Clone CBA2: CDR-H1 |
| 83 | YIYSYYGSTYYADSVK | Clone CBA2: CDR-H2 |
| 84 | YGYPGGYHFWGWWSSPYAFDY | Clone CBA2: CDR-H3 |
| 110 | DIQMTQSPSSLSASVGDRVTITCRASQSVSSAVAWYQQKPGKAPKLLIYSASSLYSGVPSRFSGSRSGTDFTLTISSLQPEDFATYYCQQHYSLITFGQGTKVEIKR | Clone CBA1 light chain variable region; CDRs bolded. |
| 34 | RASQSVSSAVA | Clone CBA1: CDR-L1 |
| 35 | SASSLYS | Clone CBA1: CDR-L2 |
| 111 | QQHYSLIT | Clone CBA1: CDR-L3 |
| 85 | EVQLVESGGGLVQPGGSLRLSCAASGFNLYSSYIHWVRQAPGKGLEWVASIYPYSSSTSYADSVKGRFTISADTSKNTAYLQMNSLRAEDTAVYYCARGGGSWSAMDYWGQGTLVTVSSAS | Clone CBA1: heavy chain variable region; CDRs bolded. |
| 2 | GFNLYSSYIH | Clone CBA1: CDR-H1 |
| 86 | SIYPYSSSTSYADSVK | Clone CBA1: CDR-H2 |
| 87 | GGGSWSAMDY | Clone CBA1: CDR-H3 |

TABLE 8 -continued

Sequences

| SEQ ID NO: | Sequence | Description |
|---|---|---|
| 112 | DIQMTQSPSSLSASVGDRVTITCRASQSVSSAVAWYQQKPGKAPKLLIYSA SSLYSGVPSRFSGSRSGTDFTLTISSLQPEDFA-TYYCQQTFYPFTFGQGTK VEIKR | Clone LG4: light chain variable region; CDRs bolded. |
| 34 | RASQSVSSAVA | Clone LG4: CDR-L1 |
| 35 | SASSLYS | Clone LG4: CDR-L2 |
| 113 | QQTFYPFT | Clone LG4: CDR-L3 |
| 114 | EVQLVESGGGLVQPGGSLRLSCAASGFNLYYSYMHWVRQAPGKGLEWVASI SSYYGYTSYADSVKGRFTISADTSKNTAYLQMNSLRAEDTAVYYCARSPIV YYELFMFIDMGAQGWKYGMDYWGQGTLVTVSSAS | Clone LG4: heavy chain variable region; CDRs bolded. |
| 115 | GFNLYYSYMH | Clone LG4: CDR-H1 |
| 116 | SISSYYGYTSYADSVK | Clone LG4: CDR-H2 |
| 117 | SPIVYYELFMFIDMGAQGWKYGMDY | Clone LG4: CDR-H3 |
| 118 | DIQMTQSPSSLSASVGDRVTITCRASQSVSSAVAWYQQKPGKAPKLLIYSA SSLYSGVPSRFSGSRSGTDFTLTISSLQPEDFATYYCQQSSHYASPPITFG QGTKVEIKR | Clone LH6: light chain variable region; CDRs bolded. |
| 34 | RASQSVSSAVA | Clone LH6: CDR-L1 |
| 35 | SASSLYS | Clone LH6: CDR-L2 |
| 119 | QQSSHYASPPIT | Clone LH6: CDR-L3 |
| 120 | EVQLVESGGGLVQPGGSLRLSCAASGFNLSYSYMHWVRQAPGKGLEWVASI YPSYGSTYYADSVKGRFTISADTSKNTAYLQMNSLRAEDTAVYYCARDLEE SLPKRARTAVSKELESVPYVMDYWGQGTLVTVSSAS | Clone LH6: heavy chain variable region; CDRs bolded. |
| 121 | GFNLSYSYMH | Clone LH6: CDR-H1 |
| 122 | SIYPSYGSTYYADSVK | Clone LH6: CDR-H2 |
| 123 | DLEESLPKRARTAVSKELESVPYVMDY | Clone LH6: CDR-H3 |
| 124 | DIQMTQSPSSLSASVGDRVTITCRASQSVSSAVAWYQQKPGKAPKLLIYSA SSLYSGVPSRFSGSRSGTDFTLTISSLQPEDFATYYCQQAYYGYLFTFGQG TKVEIKR | Clone LH11: light chain variable region; CDRs bolded. |
| 34 | RASQSVSSAVA | Clone LH11: CDR-L1 |
| 35 | SASSLYS | Clone LH11: CDR-L2 |
| 125 | QQAYYGYLFT | Clone LH11: CDR-L3 |
| 126 | EVQLVESGGGLVQPGGSLRLSCAASGFNLSYYSMHWVRQAPGKGLEWVAYI YPYYGSTYYADSVKGRFTISADTSKNTAYLQMNSLRAEDTAVYYCARFLLS IGKLFVGDGSILHVWLYGMDYWGQGTLVTVSSAS | Clone LH11: heavy chain variable region; CDRs bolded. |
| 127 | GFNLSYYSMH | Clone LH11: CDR-H1 |
| 128 | YIYPYYGSTYYADSVK | Clone LH11: CDR-H2 |
| 129 | FLLSIGKLFVGDGSILHVWLYGMDY | Clone LH11: CDR-H3 |
| 130 | MSIQHFRVALIPFFAAFCLPVFAHPETLVKVKDAEDQLGARVGYIELDLNS GKILESFRPEERFPMKSTFKVLLCGAVLSRVDAGQEQLGRRIHYSQNDLVE YSPVTEKHLTDGMTVRELCSAAITMSDNTAANLLLTTIGGPKELTAFLHNM GDHVTRLDRWEPELNEAIPNDERDTTMPAAMATTLRKLLTGELLTLASRQQ LIDWMEADKVAGPLLRSALPAGWFIADKSGAGERGSRGITAALGPDGKPSR IVVIYTTGSQATMDERNRQIAEIGASLIKHW | TEM-1 Sequence |
| 131 and 153 | MSIQHFRVALIPFFAAFCLPVFAHPETLVKVKDAEDQLGARVGYIELDLNS GKILESFRPEERFPMMSTFKVLLCGAVLSRIDAGQEQLGRRIHYSQNDLVE YSPVTEKHLTDGMTVRELCSAAITMSDNTAANLLLTTIGGPKELTAFLHNM GDHVTRLDRWEPELNEAIPNDERDTTMPVAMATTLRKLLTGSRGSGXSGGP WELLTLASRQQLIDWMEADKVAGPLLRSALPAGWFIADKSGAGERGSRGII AALGPDGKPSRIVVIYTTGSQATMDERNRQIAEIGASLIKHW | Modified TEM-1 Sequence. "X" represents the cleavable peptide insert. |

TABLE 8 -continued

Sequences

| SEQ ID NO: | Sequence | Description |
|---|---|---|
| 132 and 152 | SRGSGXSGGPW | Cleavable Peptide Insert with linking groups at the N' and C' terminal ends; "X" represents the cleavable peptide insert |
| 133 | SGRIGFLRTA | Cleavable Peptide Insert (e.g., MMP-14) |
| 134 | PLGLEEAK | Cleavable Peptide Insert (e.g., MMP-12) |
| 135 | EISEVKMDAEY | Cleavable Peptide Insert (e.g., BACE-1) |
| 136 | KLRSSKQ | Cleavable Peptide Insert (e.g., Alp2) |
| 137 | KLHFSKQ | Cleavable Peptide Insert (e.g., Cathepsin B) |
| 138 | RLPLGI | Cleavable Peptide Insert (e.g., MMP-9) |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated anti-MMP-12 antibody, or an antigen-binding fragment thereof, comprising a light chain complementarity determining region 1 (CDR1) comprising an amino acid sequence of SEQ ID NO:34, a light chain CDR2 comprising an amino acid sequence of SEQ ID NO:35, a light chain CDR3 comprising an amino acid sequence of SEQ ID NO:125, a heavy chain CDR1 comprising an amino acid sequence of SEQ ID NO:127, a heavy chain CDR2 comprising an amino acid sequence of SEQ ID NO:128, and a heavy chain CDR3 comprising an amino acid sequence of SEQ ID NO:129.

2. The isolated anti-MMP-12 antibody of claim 1, or an antigen-binding fragment thereof, comprising a light chain variable region comprising an amino acid sequence that has at least 80% sequence identity to:

(a) (SEQ ID NO: 112)
DIQMTQSPSSLSASVGDRVTITCRASQSVSSAVAWYQQKPGKAPKLL

IYSASSLYSGVPSRFSGSRSGTDFTLTISSLQPEDFATYYCQQTFYPFTFG

QGTKVEIKR;

(b) (SEQ ID NO: 118)
DIQMTQSPSSLSASVGDRVTITCRASQSVSSAVAWYQQKPGKAPKLL

IYSASSLYSGVPSRFSGSRSGTDFTLTISSLQPEDFATYYCQQSSHYASPP

ITFGQGTKVEIKR;
and (c) (SEQ ID NO: 124)
DIQMTQSPSSLSASVGDRVTITCRASQSVSSAVAWYQQKPGKAPKLL

IYSASSLYSGVPSRFSGSRSGTDFTLTISSLQPEDFATYYCQQAYYGYLFT

FGQGTKVEIKR.

3. The isolated anti-MMP-12 antibody of claim 1, or an antigen-binding fragment thereof, comprising a heavy chain variable region comprising an amino acid sequence that has at least 80% sequence identity to:

(a) (SEQ ID NO: 114)
EVQLVESGGGLVQPGGSLRLSCAASGFNLYYSYMHWVRQAPGKGLEW

VASISSYYGYTSYADSVKGRFTISADTSKNTAYLQMNSLRAEDTAVYYCAR

SPIVYYELFMFIDMGAQGWKYGMDYWGQGTLVTVSSAS;

(b) (SEQ ID NO: 120)
EVQLVESGGGLVQPGGSLRLSCAASGFNLSYSYMHWVRQAPGKGLEW

VASIYPSYGSTYYADSVKGRFTISADTSKNTAYLQMNSLRAEDTAVYYCAR

DLEESLPKRARTAVSKELESVPYVMDYWGQGTLVTVSSAS;
and (c) (SEQ ID NO: 126)
EVQLVESGGGLVQPGGSLRLSCAASGFNLSYSYMHWVRQAPGKGLEW

VAYIYPYYGSTYYADSVKGRFTISADTSKNTAYLQMNSLRAEDTAVYYCAR

FLLSIGKLFVGDGSILHVWLYGMDYWGQGTLVTVSSAS.

4. The isolated anti-MMP-12 antibody of claim 1, or an antigen-binding fragment thereof, comprising:

a light chain variable region comprising an amino acid sequence that has at least 90% sequence identity to SEQ ID NO:124 and a heavy chain variable region comprising an amino acid sequence that has at least 90% sequence identity to SEQ ID NO:126.

5. The isolated anti-MMP-12 antibody of claim 1, or an antigen-binding fragment thereof, which is an inhibitor of MMP-12.

6. A composition comprising an isolated anti-MMP-12 antibody, or an antigen-binding fragment thereof, as described in claim 1 and a carrier.

7. An isolated polynucleotide comprising a nucleotide sequence encoding an isolated anti-MMP-12 antibody, or an antigen-binding fragment thereof, of claim 1.

8. A cell comprising the polynucleotide of claim 7.

9. A method of inhibiting the activity of MMP-12, comprising contacting an MMP-12 molecule with an isolated anti-MMP-12 antibody, or an antigen-binding fragment thereof, as described in claim 1.

10. The isolated anti-MMP-12 antibody of claim 1, or an antigen-binding fragment thereof, comprising a light chain CDR1 consisting of the amino acid sequence of SEQ ID NO:34, a light chain CDR2 consisting of the amino acid sequence of SEQ ID NO:35, a light chain CDR3 consisting of the amino acid sequence of SEQ ID NO:125, a heavy chain CDR1 consisting of the amino acid sequence of SEQ ID NO:127, a heavy chain CDR2 consisting of the amino acid sequence of SEQ ID NO:128, and a heavy chain CDR3 consisting of the amino acid sequence of SEQ ID NO:129.

11. The isolated anti-MMP-12 antibody of claim 1, or an antigen-binding fragment thereof, comprising a light chain variable region comprising an amino acid sequence that has at least 90% sequence identity to:

(SEQ ID NO: 124)
DIQMTQSPSSLSASVGDRVTITCRASQSVSSAVAWYQQKPGKAPK

LLIYSASSLYSGVPSRFSGSRSGTDFTLTISSLQPEDFATYYCQQ

AYYGYLFTFGQGTKVEIKR.

12. The isolated anti-MMP-12 antibody of claim 1, or an antigen-binding fragment thereof, comprising a heavy chain variable region comprising an amino acid sequence that has at least 90% sequence identity to:

(SEQ ID NO: 126)
EVQLVESGGGLVQPGGSLRLSCAASGFNLSYYSMHWVRQAPGKG

LEWVAYIYPYYGSTYYADSVKGRFTISADTSKNTAYLQMNSLRA

EDTAVYYCARFLLSIGKLFVGDGSILHVWLYGMDYWGQGTLVTV

SSAS.

13. The isolated anti-MMP-12 antibody of claim 1, or an antigen-binding fragment thereof, comprising a light chain variable region comprising an amino acid sequence of:

(SEQ ID NO: 124)
DIQMTQSPSSLSASVGDRVTITCRASQSVSSAVAWYQQKPGKAP

KLLIYSASSLYSGVPSRFSGSRSGTDFTLTISSLQPEDFATYYC

QQAYYGYLFTFGQGTKVEIKR.

14. The isolated anti-MMP-12 antibody of claim 1, or an antigen-binding fragment thereof, comprising a heavy chain variable region comprising an amino acid sequence of:

(SEQ ID NO: 126)
EVQLVESGGGLVQPGGSLRLSCAASGFNLSYYSMHWVRQAPGKG

LEWVAYIYPYYGSTYYADSVKGRFTISADTSKNTAYLQMNSLRA

EDTAVYYCARFLLSIGKLFVGDGSILHVWLYGMDYWGQGTLVTV

SSAS.

15. The isolated anti-MMP-12 antibody of claim 1, or an antigen-binding fragment thereof, comprising a light chain variable region comprising an amino acid sequence that has at least 95% sequence identity to SEQ ID NO:124 and a heavy chain variable region comprising an amino acid sequence that has at least 95% sequence identity to SEQ ID NO:126.

16. The isolated anti-MMP-12 antibody of claim 1, or an antigen-binding fragment thereof, comprising a light chain variable region comprising an amino acid sequence that has at least 99% sequence identity to SEQ ID NO:124 and a heavy chain variable region comprising an amino acid sequence that has at least 99% sequence identity to SEQ ID NO:126.

17. The isolated anti-MMP-12 antibody of claim 1, or an antigen-binding fragment thereof, comprising a light chain variable region comprising an amino acid sequence of SEQ ID NO:124 and a heavy chain variable region comprising an amino acid of SEQ ID NO:126.

18. The isolated anti-MMP-12 antibody of claim 1, or an antigen-binding fragment thereof, comprising a light chain variable region consisting of an amino acid sequence of SEQ ID NO:124 and a heavy chain variable region consisting of an amino acid of SEQ ID NO:126.

* * * * *

UNITED STATES PATENT AND TRADEMARK OFFICE
CERTIFICATE OF CORRECTION

PATENT NO. : 11,332,546 B2
APPLICATION NO. : 16/880747
DATED : May 17, 2022
INVENTOR(S) : Xin Ge and Kibaek Lee It is certified that error appears in the above-identified patent and that said Letters Patent is hereby corrected as shown below:

In the Claims

Column 189, Lines 30-54, please delete the entirety of Claim 2 and insert -- 2. The isolated anti-MMP-12 antibody of claim 1, or an antigen-binding fragment thereof, comprising a light chain variable region comprising an amino acid sequence that has at least 80% sequence identity to:
DIQMTQSPSSLSASVGDRVTITCRASQSVSSAVAWYQQKPGKAPKLLIYSASSLYSGV PSRFSGSRSGTDFTLTISSLQPEDFATYYCQQAYYGYLFTFGQGTKVEIKR (SEQ ID NO:124). -- therefor.

Column 189, Lines 55-65, and Column 190, Lines 18-30, please delete the entirety of Claim 3 and insert -- 3. The isolated anti-MMP-12 antibody of claim 1, or an antigen-binding fragment thereof, comprising a heavy chain variable region comprising an amino acid sequence that has at least 80% sequence identity to:
EVQLVESGGGLVQPGGSLRLSCAASGFNLSYYSMHWVRQAPGKGLEWVAYIYPYYG STYYADSVKGRFTISADTSKNTAYLQMNSLRAEDTAVYYCARFLLSIGKLFVGDGSILHVWL YGMDYWGQGTLVTVSSAS (SEQ ID NO:126). -- therefor.

Signed and Sealed this
Nineteenth Day of July, 2022

Katherine Kelly Vidal
*Director of the United States Patent and Trademark Office*